(12) United States Patent
Wangh et al.

(10) Patent No.: US 10,273,525 B2
(45) Date of Patent: *Apr. 30, 2019

(54) COMPOSITIONS, METHODS, AND KITS FOR DETECTING AND IDENTIFYING MYCOBACTERIA

(75) Inventors: Lawrence J. Wangh, Auburndale, MA (US); John Rice, Quincy, MA (US)

(73) Assignee: Brandeis University, Waltham, MA (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/884,873

(22) PCT Filed: Nov. 10, 2011

(86) PCT No.: PCT/US2011/060224
§ 371 (c)(1),
(2), (4) Date: Jul. 17, 2013

(87) PCT Pub. No.: WO2012/064978
PCT Pub. Date: May 18, 2012

(65) Prior Publication Data
US 2014/0004513 A1    Jan. 2, 2014

Related U.S. Application Data

(60) Provisional application No. 61/412,190, filed on Nov. 10, 2010.

(51) Int. Cl.
*C07H 21/04*     (2006.01)
*C12Q 1/6818*    (2018.01)
*C12Q 1/689*     (2018.01)

(52) U.S. Cl.
CPC .......... *C12Q 1/6818* (2013.01); *C12Q 1/689* (2013.01); *C12Q 2600/106* (2013.01); *C12Q 2600/16* (2013.01)

(58) Field of Classification Search
USPC ........... 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS 5,422,242 A * 6/1995 Young .................. 435/6.15
5,912,148 A * 6/1999 Eggerding ............ 435/91.2
(Continued)

FOREIGN PATENT DOCUMENTS

EP    1468114    5/2008
EP     211614   11/2009
(Continued)

OTHER PUBLICATIONS

Allawi et al., "Thermodynamics and NMR of internal G.T mismatches in DNA," Biochem., 1997, 36:10581-10594.
(Continued)

*Primary Examiner* — Frank W Lu
(74) *Attorney, Agent, or Firm* — Foley Hoag LLP; Brendan T. Jones; Allison Gilder

(57) ABSTRACT

Provided herein are methods for detecting and identifying strains of mycobacteria, and compositions and kits for performing such methods. In particular, nucleic acid amplification and fluorescence detection methods are provided for the detection and differentiation of mycobacteria based on, for example, pathogenicity, species, and antibiotic resistance or sensitivity. Compositions and methods are provided herein to identify and differentiate mycobacteria in mixtures of different mycobacteria and mycobacteria and non-mycobacteria.

26 Claims, 28 Drawing Sheets
Specification includes a Sequence Listing.

(56) References Cited

U.S. PATENT DOCUMENTS

| | | |
|---|---|---|
| 6,329,138 B1 | 12/2001 | De Beenhouwer et al. |
| 6,365,729 B1 | 4/2002 | Tyagi et al. |
| 7,198,897 B2 | 4/2007 | Wangh et al. |
| 7,601,831 B2 | 10/2009 | Chou et al. |
| 7,632,642 B2 | 12/2009 | Wangh et al. |
| 7,838,235 B2 | 11/2010 | Caplin |
| 7,915,014 B2 | 3/2011 | Wangh |
| 8,367,325 B2 | 2/2013 | Wangh et al. |
| 2004/0229253 A1* | 11/2004 | Hyldig-Nielsen et al. ........ 435/6 |
| 2005/0130168 A1 | 6/2005 | Han et al. |
| 2006/0121487 A1 | 6/2006 | Alland et al. |
| 2006/0211014 A1 | 9/2006 | Iwaki |
| 2007/0083945 A1 | 4/2007 | Byrum et al. |
| 2009/0053729 A1 | 2/2009 | Ishikawa |
| 2010/0112549 A1 | 5/2010 | Rey et al. |
| 2010/0196887 A1 | 8/2010 | Hyldig-Nielsen et al. |
| 2010/0261163 A1 | 10/2010 | Zasedatelev et al. |
| 2010/0273146 A1 | 10/2010 | Brown |
| 2012/0040352 A1 | 2/2012 | Wangh et al. |
| 2013/0095479 A1 | 4/2013 | Wangh et al. |
| 2013/0130240 A1* | 5/2013 | Hellyer et al. ............... 435/6.11 |

FOREIGN PATENT DOCUMENTS

| | | |
|---|---|---|
| EP | 1805199 | 1/2011 |
| EP | 1942196 | 5/2012 |
| EP | 2546364 | 1/2013 |
| EP | 2046989 | 3/2013 |
| WO | 01/31062 | 5/2001 |
| WO | 03/008645 | 1/2003 |
| WO | 03/054233 | 7/2003 |
| WO | 2004/074447 | 9/2004 |
| WO | 2010/072366 | 7/2010 |
| WO | 2011/050173 | 4/2011 |

OTHER PUBLICATIONS

Genbank Acession No. AY192026, Mar. 2, 2003, 1 page.

Genbank Accession No. EU835534, Oct. 19, 2008, 2 pages.

Jia et al., "Dilute-'N'-Go dideoxy sequencing of all DNA strands generated in multiplex LATE-PCR assays," Nucleic Acid Res., 2010, 38(11):e119.

Ong et al., "Rapid Detection of Rifampicin- and Isoniazid-Resistant *Mycobacterium tuberculosis* by High-Resolution Melting Analysis," J Clin Microbiol., 2010, 48:1047-1054.

Pierce et al., "Linear-After-The-Exponential (LATE)—PCR: primer design criteria for high yields of specific single-stranded DNA and improved real-time detection," PNAS, 2005, 102I8609-8614.

Sanchez et al., "Linear-after-the-exponential (LATE)—PCR: an advanced method of asymmetric PCR and its uses in quantitative real-time analysis," PNAS, 2004, 101:1933-1938.

Sandgren et al., "Tuberculosis drug resistance mutation database," PLoS Med, 2009, 6(2):e2.

Santalucia, "A unified view of polymer, dumbbell, and oligonucleotide DNA nearest-neighbor thermodynamics," PNAS, 1998, 95:1460-1465.

Extended European Search Report for EP11840497.9, dated Mar. 7, 2014, 7 pages.

International Search Report and Written Opinion for PCT/US2011/060224, dated May 21, 2012, 18 pages.

* cited by examiner

C

A

B

C

D

A

B

C

D

A

B

C

SEQUENCE LISTING

<160> NUMBER OF SEQ ID NOS: 96

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctccagccag gcacgctcac gtgacagacc g                                      31

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccggtggtcg ccgcgatcaa ggag                                              24

<210> SEQ ID NO 3
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ccggtggtcg ccgcgatcaa ggagttcttc ggcaccagcc agctgagcca attcatggac        60
cagaacaacc cgctgtcggg gttgacccac aagcgccgac tgtcggcgct ggggcccggc       120
ggtctgtcac gtgagcgtgc cgggctggag                                        150

<210> SEQ ID NO 4
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccggtggtcg ccgcgatcaa ggagttcttc ggcaccagcc agctgagcca attcatggtc        60
cagaacaacc cgctgtcggg gttgacccac aagcgccgac tgtcggcgct ggggcccggc       120
ggtctgtcac gtgagcgtgc cgggctggag                                        150

<210> SEQ ID NO 5
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ccggtggtcg ccgcgatcaa ggagttcttc ggcaccagcc agctgagcca attcatggac        60
cagaacaacc cgctgtcggg gttgacccac aagcgccgac tgttggcgct ggggcccggc       120
ggtctgtcac gtgagcgtgc cgggctggag                                        150

```
<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ctggttggtg cagaag                                                        16

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tcaggtccat gaattggctc aga                                                23

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cagcgggttg tt                                                            12

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
atgcgcttgt ggatcaaccc cgat                                               24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
aagccccagc gccgacagtc gtt                                                23

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
acagaccgcc gg                                                            12
```

```
<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
accagggctg ggccatgcgc acca                                            24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaccgcagc cacgccaagt c                                               21

<210> SEQ ID NO 14
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ggaccgcagc cacgccaagt cggcccggtc ggttgccgag accatgggca actaccaccc     60
gcacggcgac gcgtcgatct acgacagcct ggtgcgcatg gcccagccct ggt           113

<210> SEQ ID NO 15
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ggaccgcagc cacgccaagt cggcccggtc ggttgccgag accatgggca actaccaccc     60
gcacggcgac gtgtcgatct acgacagcct ggtgcgcatg gcccagccct ggt           113

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
cgaccgggcc                                                            10

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 17
aacccatggt ctcggcaact t                                              21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
aatcgccgtg cgggtggtag tt                                             22

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gctgtcgtag atcgacgcg                                                 19

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agcgcccact cgtagccgta caggatctcg aggaaac                             37

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcttgggctg gaagagctcg tatggcac                                       28

<210> SEQ ID NO 22
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gcttgggctg gaagagctcg tatggcaccg gaaccggtaa ggacgcgatc accagcggca    60
tcgaggtcgt atgacgaac accccgacga aatgggacaa cagtttcctc gagatcctgt    120
acggctacga gtgggagct                                                139

<210> SEQ ID NO 23
<211> LENGTH: 139
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 23
gcttgggctg aaagagctcg tatggcaccg gaaccggtaa ggacgcgatc accaccggca      60
tcgaggtcgt atggacgaac accccgacga aatgggacaa cagtttcctc gagatcctgt    120
acggctacga gtgggagct                                                  139

<210> SEQ ID NO 24
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gcttgggctg aaagagctcg tatggcaccg gaaccggtaa ggacgcgatc accaacggca      60
tcgaggtcgt atggacgaac accccgacga aatgggacaa cagtttcctc gagatcctgt    120
acggctacga gtgggagct                                                  139

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
aagtgatcgc gtccttacct t                                               21

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gacctcgatg cagctg                                                     16

<210> SEQ ID NO 27
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
ccggtggtcg ccgcgatcaa ggagttcttc ggcaccagcc agctgagcca attcatggac      60
cagaacaacc cgctgtcggg gttgaccgac aagcgccgac tgtcggcgct ggggcccggc    120
ggtctgtcac gtgagcgtgc cgggctggag                                    150

<210> SEQ ID NO 28
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 28
ctccagccag gcacgctcac gtgacagacc g                                      31

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccggtggtcg ccgcgatcaa ggag                                              24

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ctggttggtg cagaag                                                       16

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tcaggtccat gaattggctc aga                                               23

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
cagcgggttg tt                                                           12

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
atgcgcttgt ggatcaaccc cgat                                              24

<210> SEQ ID NO 34
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 34
aagccccagc gccgacagtc gtt                                              23

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
acagaccgcc gg                                                          12

<210> SEQ ID NO 36
<211> LENGTH: 150
<212> TYPE: DNA
<213> ORGANISM: Mycobacterium tuberculosis

<400> SEQUENCE: 36
ccggtggtcg ccgcgatcaa ggagttcttc ggcaccagcc agctgagcca attcatgggc      60
cagaacaacc cgctgtcggg gttgacccac aagcgccgac tgtcggcgct ggggcccggc     120
ggtctgtcac gtgagcgtgc ctggctggag                                      150

<210> SEQ ID NO 37
<211> LENGTH: 150
<212> TYPE: DNA
<213> ORGANISM: Mycobacterium tuberculosis

<400> SEQUENCE: 37
ccggtggtcg ccgcgatcaa ggagttcttc ggcaccagcc agctgagccc attcatggac      60
cagaacaacc cgctgtcggg gttgacccac aagcgccgac tgtcggcgct ggggcccggc     120
ggtctgtcac gtgagcgtgc ctggctggag                                      150

<210> SEQ ID NO 38
<211> LENGTH: 150
<212> TYPE: DNA
<213> ORGANISM: Mycobacterium africanum

<400> SEQUENCE: 38
ccggtggtcg ccgcgatcaa ggagttcttc ggcaccagcc agctgagcca attcatggac      60
cagaacaacc cgctgtcggg gttgacccac aagcgccgac tgtcggcgct ggggcccggc     120
ggtctgtcac gtgagcgtgc cgggctggag                                      150

<210> SEQ ID NO 39
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agcgcccact cgtagccgta caggatctcg aggaaac                               37
```

```
<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcttgggctg gaagagctcg tatggcac                                        28

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
gtatcgcgtc cttaccggtt ccac                                            24

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
ctcgatgctg ctggtg                                                     16

<210> SEQ ID NO 43
<211> LENGTH: 139
<212> TYPE: DNA
<213> ORGANISM: Mycobacterium tuberculosis

<400> SEQUENCE: 43
gcttgggctg gaagagctcg tatggcaccg gaaccggtaa ggacgcgatc accaccggca     60
tcgaggtcgt atggacgaac accccgacga aatgggacaa cagtttcctc gagatcctgt    120
acggctacga gtgggagct                                                 139

<210> SEQ ID NO 44
<211> LENGTH: 139
<212> TYPE: DNA
<213> ORGANISM: Mycobacterium intracellulare

<400> SEQUENCE: 44
ggctgggctg gaagagctcg tacggcaccg gttcgggcaa ggatgcgatc accagcggcc     60
tcgaggtggt ctggacgccc accccgacga agtgggacaa cagcttcctg gagacgctgt    120
acggctacga atgggagct                                                 139

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttccggtaac caggactgaa cgggatacga atgggggttt gg                        42
```

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tcgcagccac gttacgctcg tggacatac                                        29

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 47
ttacaaccta tcgtctcgcc gcaa                                             24

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic probe

<400> SEQUENCE: 48
gcagtcaccc cg                                                          12

<210> SEQ ID NO 49
<211> LENGTH: 182
<212> TYPE: DNA
<213> ORGANISM: Mycobacterium tuberculosis

<400> SEQUENCE: 49
tcgcagccac gttacgctcg tggacatacc gatttcggcc cggccgcggc gagacgatag      60
gttgtcgggg tgactgccac agccactgaa ggggccaaac ccccattcgt atcccgttca     120
gtcctggtta ccggaggaaa ccgggggatc gggctggcga tcgcacagcg gctggctgcc     180
ga                                                                   182

<210> SEQ ID NO 50
<211> LENGTH: 182
<212> TYPE: DNA
<213> ORGANISM: Mycobacterium tuberculosis

<400> SEQUENCE: 50
tcgcagccac gttacgctcg tggacatacc gatttcggcc cggccgcggc gagatgatag      60
gttgtcgggg tgactgccac agccactgaa ggggccaaac ccccattcgt atcccgttca     120
gtcctggtta ccggaggaaa ccgggggatc gggctggcga tcgcacagcg gctggctgcc     180
ga                                                                   182

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 51
acaccctctc aggccggcta cccgtcg                                              27

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gagtggcgaa cgggtgagta acacg                                               25

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
ttggctcatc ccacaccgct aaagtgcttt aa                                       32

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
ccaccacaag atatgcgtct cgtgttccta t                                        31

<210> SEQ ID NO 55
<211> LENGTH: 211
<212> TYPE: DNA
<213> ORGANISM: Unknown
<220> FEATURE:
<223> OTHER INFORMATION: Description of Unknown:
      Mycobacterium tuberculosis or Mycobacterium africanum

<400> SEQUENCE: 55
gagtggcgaa cgggtgagta acacgtgggt gatctgccct gcacttcggg ataagcctgg         60
gaaactgggt ctaataccgg ataggaccac gggatgcatg tcttgtggtg aaagcgctt         120 tagcggtgtg ggatgagccc gcggcctatc agcttgttgg tggggtgacg gcctaccaag       180
gcgacgacgg gtagccggcc tgagagggtg t                                      211

<210> SEQ ID NO 56
<211> LENGTH: 209
<212> TYPE: DNA
<213> ORGANISM: Mycobacterium intracellulare

<400> SEQUENCE: 56
gagtggcgaa cgggtgagta acacgtgggc aatctgccct gcacttcggg ataagcctgg         60
gaaactgggt ctaataccgg ataggacctt tagacgcatg tcttttggtg aaagcttt         120 gcggtgtggg atgggcccgc ggcctatcag cttgttggtg ggtgacggc ctaccaaggc       180 gacgacgggt agccggcctg agagggtgt                                         209
```

```
<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atacgggctt gcgccgagga cac                                            23

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtcagcgaac cgcagttcga gggccagacc aagacc                              36

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccactggttt gaagccaacc cca                                            23

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
cgtgtaatga atagctgcg                                                 19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
aggacgcgaa agtcgttgct                                                20

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
tgaacaaggc t                                                         11
```

```
<210> SEQ ID NO 63
<211> LENGTH: 170
<212> TYPE: DNA
<213> ORGANISM: Mycobacterium tuberculosis

<400> SEQUENCE: 63
gtcagcgaac cgcagttcga gggccagacc aagaccaagt tgggcaacac cgaggtcaaa      60
tcgtttgtgc agaaggtctg taacgaacag ctgacccact ggtttgaagc caaccccacc     120
gacgcgaaag tcgttgtgaa caaggctgtg tcctcggcgc aagcccgtat                170

<210> SEQ ID NO 64
<211> LENGTH: 170
<212> TYPE: DNA
<213> ORGANISM: Mycobacterium africanum

<400> SEQUENCE: 64
gtcagcgaac cgcagttcga gggccagacc aagaccaagt tgggcaacac cgaggtcaaa      60
tcgtttgtgc agaaggtctg taacgaacag ctgacccact ggtttgaagc caaccccacc     120
gactcgaaag tcgttgtgaa caaggctgtg tcctcggcgc aagcccgtat                170

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggagcagact agcactgagg ta                                               22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tacctcagtg ctagtctgct cc                                               22

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atcctccggg ctgccgaacc agcgga                                           26

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgctctggca tgtcatcggc gcgaattcgt                                       30
```

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
ttctcgggtc atgctcaaa                                                19

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
gggtgtagcc                                                          10

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
gcttgaccgc cggcagcccg tcgatgc                                       27

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
agtcggcgga gaagggttga gtgc                                          24

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
gacaggtcgc cgccgatgag agcggtgagc                                    30

<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
cgatatggtg tgatatatca cctttgcctg acagc                              35

```
<210> SEQ ID NO 75
<211> LENGTH: 170
<212> TYPE: DNA
<213> ORGANISM: Mycobacterium microti

<400> SEQUENCE: 75
gtcagcgaac cgcagttcga gggccagacc aagaccaagt tgggcaacac cgaggtcaaa      60
tcgtttgtgc agaaggtctg taacgaacag ctgacccact ggtttgaagc caaccccacc     120
gactcgaaag tcgttgtgaa caaggctgtg tcctcggcgc aagcccgtat                170

<210> SEQ ID NO 76
<211> LENGTH: 170
<212> TYPE: DNA
<213> ORGANISM: Mycobacterium bovis

<400> SEQUENCE: 76
gtcagcgaac cgcagttcga gggccagacc aagaccaagt tgggcaacac cgaggtcaaa      60
tcgtttgtgc agaaggtctg taatgaacag ctgacccact ggtttgaagc caaccccacc     120
gactcgaaag tcgttgtgaa caaggctgtg tcctcggcgc aagcccgtat                170

<210> SEQ ID NO 77
<211> LENGTH: 122
<212> TYPE: DNA
<213> ORGANISM: Mycobacterium chelonae

<400> SEQUENCE: 77
gtcggcgaac ctcagttcga gggtcaaacc aagaccaagc tgggcaacac cgaggtcaag      60
tcgtttgtgc agaaggtgtg caacgagcag ctgcagcact ggttcgactc gaaccccgcc     120
ga                                                                    122

<210> SEQ ID NO 78
<211> LENGTH: 122
<212> TYPE: DNA
<213> ORGANISM: Mycobacterium intracellulare

<400> SEQUENCE: 78
gtcagcgaac cgcagttcga gggtcagacc aagaccaagc tgggcaacac cgaagtgaag      60
tcgttcgtgc agaaggtctg caacgaacag ctcacccact ggttcgaggc caaccccgcg     120
ga                                                                    122

<210> SEQ ID NO 79
<211> LENGTH: 122
<212> TYPE: DNA
<213> ORGANISM: Mycobacterium asiaticum

<400> SEQUENCE: 79
gtcgccgaac cccagttcga gggccagaca aagaccaagc tgggcaacac cgaggtcaag      60
tcgttcgtgc agaaggtgtg caacgaacag ctcacccact ggttcgaggc caatccgtcg     120
ga                                                                    122

<210> SEQ ID NO 80
<211> LENGTH: 121
<212> TYPE: DNA
<213> ORGANISM: Mycobacterium avium
```

```
<400> SEQUENCE: 80
gtgagcgaac cgcagttcga gggccagacc aagaccaaac tgggcaacac cgaggtgaag      60
tcgttcgtgc agaaggtgtg caacgaacag ctcacccact ggttcgaagc caaccccgca     120
g                                                                     121

<210> SEQ ID NO 81
<211> LENGTH: 209
<212> TYPE: DNA
<213> ORGANISM: Mycobacterium chelonae

<400> SEQUENCE: 81
gagtggcgaa cgggtgagta acacgtgggt gatctgccct gcactctggg ataagcctgg      60
gaaactgggt ctaataccgg ataggaccac acacttcatg gtgagtggtg caaagctttt     120
gcggtgtggg atgagcccgc ggcctatcag cttgttggtg ggtaatggcc caccaaggc     180 gacgacgggt agccggcctg agagggtga                                       209

<210> SEQ ID NO 82
<211> LENGTH: 209
<212> TYPE: DNA
<213> ORGANISM: Mycobacterium asiaticum

<400> SEQUENCE: 82
gagtggcgaa cgggtgagta acacgtgggt gatctgccct gcacttcggg ataagcctgg      60
gaaactgggt ctaataccgg ataggaccac gggatgcatg tcctgtggtg gaaagctttt     120
gcggtgtggg atgggcccgc ggcctatcag cttgttggtg ggtgacggc ctaccaaggc     180 gacgacgggt agccggcctg agagggtgt                                       209

<210> SEQ ID NO 83
<211> LENGTH: 209
<212> TYPE: DNA
<213> ORGANISM: Mycobacterium avium

<400> SEQUENCE: 83
gagtggcgaa cgggtgagta acacgtgggc aatctgccct gcacttcggg ataagcctgg      60
gaaactgggt ctaataccgg ataggacctc aagacgcatg tcttctggtg gaaagctttt     120
gcggtgtggg atgggcccgc ggcctatcag cttgttggtg ggtgacggc ctaccaaggc     180 gacgacgggt agccggcctg agagggtgt                                       209

<210> SEQ ID NO 84
<211> LENGTH: 209
<212> TYPE: DNA
<213> ORGANISM: Mycobacterium fortuitum

<400> SEQUENCE: 84
gagtggcgaa cgggtgagta acacgtgggt gatctgccct gcactctggg ataagcctgg      60
gaaactgggt ctaataccga ataggaccgc gctcttcatg tggggtggtg gaaagctttt     120
gcggtgtggg atgggcccgc ggcctatcag cttgttggtg ggtaatggc ctaccaaggc     180 gacgacgggt agccggcctg agagggtgt                                       209

<210> SEQ ID NO 85
<211> LENGTH: 108
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (12)..(12)
<223> OTHER INFORMATION: a, c, t or g
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (18)..(18)
<223> OTHER INFORMATION: a, c, t or g
<220> FEATURE:
<221> NAME/KEY: modified_base
<222> LOCATION: (24)..(24)
<223> OTHER INFORMATION: a, c, t or g
<220> FEATURE:
<221> NAME/KEY: modified_base
<222> LOCATION: (27)..(27)
<223> OTHER INFORMATION: a, c, t or g
<220> FEATURE:
<221> NAME/KEY: modified_base
<222> LOCATION: (51)..(51)
<223> OTHER INFORMATION: a, c, t or g
<220> FEATURE:
<221> NAME/KEY: modified_base
<222> LOCATION: (54)..(54)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (60)..(60)
<223> OTHER INFORMATION: a, c, t or g
<220> FEATURE:
<221> NAME/KEY: modified_base
<222> LOCATION: (63)..(63)
<223> OTHER INFORMATION: a, c, t or g
<220> FEATURE:
<221> NAME/KEY: modified_base
<222> LOCATION: (66)..(66)
<223> OTHER INFORMATION: a, c, t or g
<220> FEATURE:
<221> NAME/KEY: modified_base
<222> LOCATION: (75)..(75)
<223> OTHER INFORMATION: a, c, t or g
<220> FEATURE:
<221> NAME/KEY: modified_base
<222> LOCATION: (78)..(78)
<223> OTHER INFORMATION: a, c, t or g
<220> FEATURE:
<221> NAME/KEY: modified_base
<222> LOCATION: (81)..(81)
<223> OTHER INFORMATION: a, c, t or g
<220> FEATURE:
<221> NAME/KEY: modified_base
<222> LOCATION: (84)..(84)
<223> OTHER INFORMATION: a, c, t or g
<220> FEATURE:
<221> NAME/KEY: modified_base
<222> LOCATION: (87)..(87)
<223> OTHER INFORMATION: a, c, t or g
<220> FEATURE:
<221> NAME/KEY: modified_base
<222> LOCATION: (90)..(90)
<223> OTHER INFORMATION: a, c, t or g
<220> FEATURE:
<221> NAME/KEY: modified_base
<222> LOCATION: (93)..(93)
<223> OTHER INFORMATION: a, c, t or g
<220> FEATURE:
<221> NAME/KEY: modified_base
<222> LOCATION: (96)..(96)
<223> OTHER INFORMATION: a, c, t or g
```

<220> FEATURE:
<221> NAME/KEY: modified_base
<222> LOCATION: (99)..(99)
<223> OTHER INFORMATION: a, c, t or g
<220> FEATURE:
<221> NAME/KEY: modified_base
<222> LOCATION: (102)..(102)
<223> OTHER INFORMATION: a, c, t or g
<220> FEATURE:
<221> NAME/KEY: modified_base
<222> LOCATION: (105)..(105)
<223> OTHER INFORMATION: a, c, t or g
<220> FEATURE:
<221> NAME/KEY: modified_base
<222> LOCATION: (108)..(108)
<223> OTHER INFORMATION: a, c, t or g

<400> SEQUENCE: 85
garttyttyg gnacnwsnca rytnwsncar ttyatggayc araayaaycc nytnwsnggn    60
ytnacncaya armgnmgnyt nwsngcnytn rgnccnggng gnytnwsn                108

<210> SEQ ID NO 86
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(69)

<400> SEQUENCE: 86 ctg agc caa ttc atg gac cag aac aac ccg ctg tcg ggg ttg acc cac    48
Leu Ser Gln Phe Met Asp Gln Asn Asn Pro Leu Ser Gly Leu Thr His
1               5                   10                  15 aag cgc cga ctg tcg gcg ctg                                        69
Lys Arg Arg Leu Ser Ala Leu
            20

<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Ser Gln Phe Met Asp Gln Asn Asn Pro Leu Ser Gly Leu Thr His
1               5                   10                  15

Lys Arg Arg Leu Ser Ala Leu
            20

<210> SEQ ID NO 88
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(69)
<220> FEATURE:
<221> NAME/KEY: modified_base
<222> LOCATION: (46)..(46)
<223> OTHER INFORMATION: a, c, t, g, unknown or other

<400> SEQUENCE: 88

```
cbg msc mwa ttc atg kds cag aac aac ccg ctg tcg ggg ttg acc ndm    48
Xaa Xaa Xaa Phe Met Xaa Gln Asn Asn Pro Leu Ser Gly Leu Thr Xaa
1               5                   10                  15 aag cgc cga ctg tbk gcg syg                                        69
Lys Arg Arg Leu Xaa Ala Xaa
            20
```

<210> SEQ ID NO 89
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: The 'Xaa' at location 1 stands for Arg, Pro or
      Leu
<220> FEATURE:
<221> NAME/KEY: MOD_RES
<222> LOCATION: (2)..(2)
<223> OTHER INFORMATION: The 'Xaa' at location 2 stands for Ser, Thr or
      Arg
<220> FEATURE:
<221> NAME/KEY: MOD_RES
<222> LOCATION: (3)..(3)
<223> OTHER INFORMATION: The 'Xaa' at location 3 stands for Lys, Gln or
      Leu
<220> FEATURE:
<221> NAME/KEY: MOD_RES
<222> LOCATION: (6)..(6)
<223> OTHER INFORMATION: The 'Xaa' at location 6 stands for Glu, Asp,
      Gly, Val or Tyr
<220> FEATURE:
<221> NAME/KEY: MOD_RES
<222> LOCATION: (16)..(16)
<223> OTHER INFORMATION: The 'Xaa' at location 16 stands for Asn, Arg,
      Glu, Asp, His, Leu or Tyr
<220> FEATURE:
<221> NAME/KEY: MOD_RES
<222> LOCATION: (21)..(21)
<223> OTHER INFORMATION: The 'Xaa' at location 21 stands for Trp, Cys,
      Ser or Leu
<220> FEATURE:
<221> NAME/KEY: MOD_RES
<222> LOCATION: (23)..(23)
<223> OTHER INFORMATION: The 'Xaa' at location 23 stands for Val, Pro or
      Leu

<400> SEQUENCE: 89

```
Xaa Xaa Xaa Phe Met Xaa Gln Asn Asn Pro Leu Ser Gly Leu Thr Xaa
1               5                   10                  15

Lys Arg Arg Leu Xaa Ala Xaa
            20
```

<210> SEQ ID NO 90
<211> LENGTH: 150
<212> TYPE: DNA
<213> ORGANISM: Mycobacterium tuberculosis

<400> SEQUENCE: 90

```
ctccagccag gcacgctcac gtgacagacc gccgggcccc agcgccgaca gtcggcgctt    60
gtgggtcaac cccgacagcg ggttgttctg gtccatgaat tggctcagct ggctggtgcc   120
gaagaactcc ttgatcgcgg cgaccaccgg                                    150
```

```
<210> SEQ ID NO 91
<211> LENGTH: 150
<212> TYPE: DNA
<213> ORGANISM: Mycobacterium avium

<400> SEQUENCE: 91
ctccagcccg gcccgctccc gggacagacc acccgggccc agcgccgaca ggcggcgctt      60
gtgggtgagc cccgacagcg ggttgttctg gtccatgaac tgggacagct ggctggtgcc    120
gaagaactcc ttgatcgccg ccacgactgg                                      150

<210> SEQ ID NO 92
<211> LENGTH: 139
<212> TYPE: DNA
<213> ORGANISM: Mycobacterium tuberculosis

<400> SEQUENCE: 92
agctcccact cgtagccgta caggatctcg aggaaactgt tgtcccattt cgtcggggtg      60
ttcgtccata cgacctcgat gccgctggtg atcgcgtcct taccggttcc ggtgccatac    120
gagctcttcc agcccaagc                                                  139

<210> SEQ ID NO 93
<211> LENGTH: 139
<212> TYPE: DNA
<213> ORGANISM: Mycobacterium avium

<400> SEQUENCE: 93
agctcccact cgtagccgta cagggtctcc aggaaggtgt tgtcccactt ggtcggggtg      60
ggcgtccaga ccacctccag gccgctggtg atggcgtcct tgcccacgcc ggtcccgtac    120
gagctcttcc agcccagac                                                  139

<210> SEQ ID NO 94
<211> LENGTH: 170
<212> TYPE: DNA
<213> ORGANISM: Mycobacterium intracellulare

<400> SEQUENCE: 94
gtcagcgaac cgcagttcga gggtcagacc aagaccaagc tgggcaacac cgaagtgaag      60
tcgttcgtgc agaaggtctg caacgaacag ctcacccact ggttcgaggc caaccccgcg    120
gacgccaagg tggtggtcaa caaggcggtg tcgtcggcgc aggcccggat                170

<210> SEQ ID NO 95
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gcttgggctg gaagagctcg tatggcac                                         28

<210> SEQ ID NO 96
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 96
gagttcttcg gcaccagcca gctgagccaa ttcatggacc agaacaaccc gctgtcgggg        60
ttgacccaca agcgccgact gtcggcgctg gggcccggcg gtctgtca                    108
```

COMPOSITIONS, METHODS, AND KITS FOR DETECTING AND IDENTIFYING MYCOBACTERIA

CROSS-REFERENCE TO RELATED APPLICATION

This present invention is a national phase application under 35 U.S.C. § 371 of PCT International Application No. PCT/US2011/060224, filed Nov. 10, 2011, which published as International Publication No. WO/2012/064978, which claims priority to U.S. Provisional Patent Application Ser. No. 61/412,190 filed Nov. 10, 2010, each of which are hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 7, 2017, is named BUG-053_01 (22247_05301)_SL.txt and is 30,082 bytes in size.

FIELD

Provided herein are methods for detecting and identifying strains of mycobacteria, and compositions and kits for performing such methods. In particular, nucleic acid amplification and fluorescence detection methods are provided for the detection and differentiation of mycobacteria based on, for example, pathogenicity, species, and antibiotic resistance or sensitivity. Compositions and methods are provided herein to identify and differentiate mycobacteria in mixtures of different mycobacteria and non-mycobacteria.

BACKGROUND

*Mycobacterium* is a genus of Actinobacteria, given its own family, the Mycobacteriaceae. The genus includes pathogens known to cause serious diseases in mammals, including tuberculosis (TB) and leprosy (Ryan & Ray (editors) (2004). Sherris Medical Microbiology (4th ed.). McGraw Hill.; herein incorporated by reference in its entirety). Mycobacteria can colonize their hosts without the hosts showing any adverse signs. For example, billions of people around the world have asymptomatic infections of *M. tuberculosis*. Mycobacteria are naturally resistant to a number of antibiotics, such as penicillin, and many other antibiotic-resistant strains have emerged.

Mycobacteria are classified as *M. tuberculosis* complex (MTBC) or non-tuberculosis mycobacteria (NTM) for the purposes of diagnosis and treatment. MTBC comprises species which can cause tuberculosis: *M. tuberculosis, M. bovis, M. africanum, M. canetti*, and *M. microti*. NTM are all the other mycobacteria, which can cause pulmonary disease resembling tuberculosis, lymphadenitis, skin disease, disseminated disease, Hansen's disease, and leprosy. Of the MTBC and NTM, different species are more or less common in different regions of the world, and exhibit different pathogenic and virulence characteristics.

The presence of antibiotic resistant TB, and multidrug-resistant TB (MDR TB) and extensively drug resistant TB (XDR TB) in particular, is of great concern to the medical community. MDR TB is TB that is resistant to two first-line anti-TB drugs, isoniazid and rifampicin, which are typically are used to treat all persons with TB disease. XDR TB is currently a relatively rare type of MDR TB, defined as TB that is resistant to isoniazid and rifampin, plus resistant to any fluoroquinolone and at least one of three injectable second-line drugs (e.g., amikacin, kanamycin, or capreomycin). Because XDR TB is resistant to first-line and second-line drugs, patients are left with treatment options that are much less effective. Resistant forms of TB raise concerns of a future TB epidemic with restricted treatment options, and jeopardize the progress made in worldwide TB treatment and control.

Mycobacteria infection can commonly consist of a mixed infection of: mycobacteria in the presence of other infectious agents, NTM and MTBC, different species of NTM or MTBC, and/or mycobacteria with different antibiotic resistance profiles.

SUMMARY

In some embodiments, provided herein are methods for identifying one or more types of mycobacteria in a sample, comprising (a) providing: (i) a sample suspected of comprising one or more mycobacteria, and (ii) detection reagents comprising at least one pair of primers and at least one detectably distinguishable probe set of two hybridization probes which hybridize to adjacent target nucleic acid sequences in one or more mycobacteria, each probe set comprising: (A) a quencher probe labeled with a non-fluorescent quencher, and (B) a signaling probe labeled with a fluorescence-emitting dye and a non-fluorescent quencher, wherein the signal probe does not emit fluorescence above background when not hybridized to its target sequence, but emits a fluorescence signal above background upon hybridization to its target sequence in the absence of bound quencher probe, wherein, if both signaling and quencher probes are hybridized to their adjacent target nucleic acid sequences, the non-fluorescent quencher of the quencher probe quenches the signal from the signaling probe; (b) amplifying nucleic acid from one or more mycobacteria with the primers; (c) detecting the fluorescence of the fluorescence-emitting dye from each detectably distinguishable probe set at a range of temperatures; (d) generating temperature-dependent fluorescence signatures for each fluorescence-emitting dye; and (e) analyzing the temperature-dependent fluorescence signatures to identify one or more *mycobacterium* in the sample.

In some embodiments, the melting temperature of the signaling probe in a probe set is higher than the melting temperature of the associated quencher probe. In some embodiments, the quencher probe and/or signaling probe are configured to hybridize to a variable region of mycobacteria nucleic acid. In some embodiments, the fluorescence-emitting dye and the non-fluorescent quenchers of each probe set are capable of interacting by FRET. In some embodiments, the detection reagents comprise two or more probe sets. In some embodiments, two or more probe sets comprise different fluorescence-emitting dyes that emit at detectably different wavelengths. In some embodiments, two or more probe sets comprise the same fluorescence-emitting dyes. In some embodiments, the probes sets comprising the same fluorescence-emitting dyes hybridize to their target nucleic acid sequences at detectably different melting temperatures with their target nucleic acid sequences. In some embodiments, the each of the two or more probe sets are detectably distinguishable from all other probe sets in said detection reagents by (1) melting temperature, (2) emission wavelength of said fluorescence-emitting dye, or (3) a combination thereof. In some embodiments, the detection reagents comprise 5 or more probe sets. In some embodiments, the detection reagents comprise 10 or more probe sets. In some embodiments, a probe set is used to differentiate between mycobacteria of different pathogenicity, species, or antibiotic resistance. In some embodiments, one or both probes of said probe set comprise different degrees of complementarity to their target sequences in two or more different mycobacteria. In some embodiments, the different degrees of complementarity result in different temperature-dependent fluorescent signatures generated by a probe set and its target sequences. In some embodiments, the different temperature dependent fluorescent signatures are used to differentiate different mycobacteria in a sample. In some embodiments, the temperature-dependent fluorescence signature comprises a melt curve or an annealing curve. In some embodiments, the analyzing the temperature-dependent fluorescence signature comprises comparison to a previously established melting curve or annealing curve. In some embodiments, analyzing is performed by a computer. In some embodiments, amplification is by a non-symmetric amplification method that includes extension of primers and a mean primer annealing temperature after the first few amplification cycles. In some embodiments, amplification is by LATE-PCR amplification. In some embodiments, the probes in at least one detectably distinguishable probe set have melting temperatures with their target nucleic acid sequences below the annealing temperature of at least one primer of the amplification reaction.

In some embodiments, one or more detectably distinguishable probe sets are configured to hybridize to a region of mycobacteria nucleic acid to differentiate between NTM and MTBC. In some embodiments, the one or more primer pairs are configured to amplify a region of mycobacteria nucleic acid that varies between NTM and MTBC. In some embodiments, the region of mycobacteria nucleic acid comprises 16s rRNA. In some embodiments, the one or more detectably distinguishable probe sets comprise SEQ ID NO.:53 and SEQ ID NO.:54 or have 70% or greater identity therewith (e.g., 75%, 80%, 85%, 90%, 95%). In some embodiments, the one or more primer pairs comprise SEQ ID NO.:51 and SEQ ID NO.:52 or have 70% or greater identity therewith (e.g., 75%, 80%, 85%, 90%, 95%).

In some embodiments, one or more detectably distinguishable probe sets are configured to hybridize to a region of mycobacteria nucleic acid to differentiate between different species of MTBC. In some embodiments, the one or more primer pairs are configured to amplify a region of mycobacteria nucleic acid that varies between different species of MTBC. In some embodiments, the region of mycobacteria nucleic acid comprises the gyrB gene. In some embodiments, one or more detectably distinguishable probe sets comprise SEQ ID NO.:61 and SEQ ID NO.:62 or have 70% or greater identity therewith (e.g., 75%, 80%, 85%, 90%, 95%). In some embodiments, the one or more detectably distinguishable probe sets further comprise SEQ ID NO.:59 or have 70% or greater identity therewith (e.g., 75%, 80%, 85%, 90%, 95%). In some embodiments, the one or more detectably distinguishable probe sets further comprise SEQ ID NO.:60 or have 70% or greater identity therewith (e.g., 75%, 80%, 85%, 90%, 95%). In some embodiments, the one or more primer pairs comprise SEQ ID NO.:57 and SEQ ID NO.:58 or have 70% or greater identity therewith (e.g., 75%, 80%, 85%, 90%, 95%).

In some embodiments, three or more detectably distinguishable probe sets are configured to hybridize to a region of mycobacteria nucleic acid to differentiate between rifampin-resistant and rifampin-sensitive mycobacteria. In some embodiments, one or more primer pairs are configured to amplify a region of mycobacteria nucleic acid that varies between rifampin-resistant and rifampin-sensitive mycobacteria. In some embodiments, the region of mycobacteria nucleic acid comprises the rpoB gene. In some embodiments, the three or more detectably distinguishable probe sets comprise SEQ ID NO.:30, SEQ ID NO.:31, SEQ ID NO.:32, SEQ ID NO.:33, SEQ ID NO.:34, and SEQ ID NO.:35 or have 70% or greater identity therewith (e.g., 75%, 80%, 85%, 90%, 95%). In some embodiments, the one or more primer pairs comprise SEQ ID NO.:28 and SEQ ID NO.:29 or have 70% or greater identity therewith (e.g., 75%, 80%, 85%, 90%, 95%).

In some embodiments, one or more detectably distinguishable probe sets are configured to hybridize to a region of mycobacteria nucleic acid to differentiate between ethambutol-resistant and ethambutol-sensitive mycobacteria. In some embodiments, the one or more primer pairs are configured to amplify a region of mycobacteria nucleic acid that varies between ethambutol-resistant and ethambutol-sensitive mycobacteria. In some embodiments, the region of mycobacteria nucleic acid comprises the embB gene. In some embodiments, the one or more detectably distinguishable probe sets comprise SEQ ID NO.:69 and SEQ ID NO.:70 or have 70% or greater identity therewith (e.g., 75%, 80%, 85%, 90%, 95%). In some embodiments, the one or more primer pairs comprise SEQ ID NO.:67 and SEQ ID NO.:68 or have 70% or greater identity therewith (e.g., 75%, 80%, 85%, 90%, 95%).

In some embodiments, one or more detectably distinguishable probe sets are configured to hybridize to a region of mycobacteria nucleic acid comprising the tlyA gene. In some embodiments, the one or more primer pairs are configured to amplify a region of the mycobacteria tlyA nucleic acid that varies between species of mycobacteria. In some embodiments, the one or more primer pairs comprise SEQ ID NO.:71 and SEQ ID NO.:72 or have 70% or greater identity therewith (e.g., 75%, 80%, 85%, 90%, 95%).

In some embodiments, the one or more detectably distinguishable probe sets are configured to hybridize to a region of mycobacteria nucleic acid to differentiate between isoniazid-resistant and isoniazid-sensitive mycobacteria. In some embodiments, the one or more primer pairs are configured to amplify a region of mycobacteria nucleic acid that varies between isoniazid-resistant and isoniazid-sensitive mycobacteria. In some embodiments, the region of mycobacteria nucleic acid comprises the mabA promoter region. In some embodiments, the one or more detectably distinguishable probe sets comprise SEQ ID NO.:47 and SEQ ID NO.:48 or have 70% or greater identity therewith (e.g., 75%, 80%, 85%, 90%, 95%). In some embodiments, the one or more primer pairs comprise SEQ ID NO.:45 and SEQ ID NO.:46 or have 70% or greater identity therewith (e.g., 75%, 80%, 85%, 90%, 95%).

In some embodiments, one or more detectably distinguishable probe sets are configured to hybridize to a region of mycobacteria nucleic acid comprising the ahpC gene. In some embodiments, the one or more primer pairs are configured to amplify a region of the mycobacteria ahpC nucleic acid that varies between species of mycobacteria. In some embodiments, the one or more primer pairs comprise SEQ ID NO.:73 and SEQ ID NO.:74 or have 70% or greater identity therewith (e.g., 75%, 80%, 85%, 90%, 95%).

In some embodiments, one or more detectably distinguishable probe sets are configured to hybridize to a region of mycobacteria nucleic acid comprising the katG gene. In some embodiments, the one or more primer pairs are configured to amplify a region of the mycobacteria katG nucleic acid that varies between species of mycobacteria. In some embodiments, the one or more detectably distinguishable probe sets comprise SEQ ID NO.:41 and SEQ ID NO.:42 or have 70% or greater identity therewith (e.g., 75%, 80%, 85%, 90%, 95%). In some embodiments, the one or more primer pairs comprise SEQ ID NO.:39 and SEQ ID NO.:40 or have 70% or greater identity therewith (e.g., 75%, 80%, 85%, 90%, 95%).

In some embodiments, one or more detectably distinguishable probe sets are configured to hybridize to a region of mycobacteria nucleic acid to differentiate between fluoroquinolone-resistant and fluoroquinolone-sensitive mycobacteria. In some embodiments, the one or more primer pairs are configured to amplify a region of mycobacteria nucleic acid that varies between fluoroquinolone-resistant and fluoroquinolone-sensitive mycobacteria. In some embodiments, the region of mycobacteria nucleic acid comprises the gyrA gene.

In some embodiments, identifying one or more *mycobacterium* in a sample comprises: (a) differentiating between NTM and MTBC; (b) differentiating between different species of MTBC; (c) differentiating between isoniazid-resistant and isoniazid-sensitive mycobacteria; (d) differentiating between fluoroquinolone-resistant and fluoroquinolone-sensitive mycobacteria; (e) differentiating between ethambutol-resistant and ethambutol-sensitive mycobacteria; and/or (f) differentiating between rifampin-resistant and rifampin-sensitive mycobacteria. In some embodiments, a multiplex reaction is conducted (e.g., in a single closed tube or other reaction vessel) using a plurality of primers and probes to achieve any one or more or all of (a) through (f). In some such embodiments, four or fewer (three, two, or one) optically distinguishable labels are employed in the multiplex reaction. For example, in some embodiments, each of (a) through (f) is achieved using four or fewer "colors," such that an instrument configured to detect up to four colors may be employed to collect and analyze the data.

In some embodiments, the desired target to be detected (e.g., a specific drug-resistant strain of *mycobacterium*) is present in a sample comprising a substantial amount of nucleic acid from non-target sources. Such non-target sources include, but are not limited to, human genomic nucleic acid, nucleic acid from non-*mycobacterium* pathogenic organisms, other *mycobacterium*, and *mycobacterium* having a different drug-resistance profile. In some embodiments the target is present at less than 20% of the total nucleic acid in the sample (by copy number) (e.g., less than 10%, less than 5%, less than 1%, less than 0.5%, or less than 0.1%).

In some embodiments, provided herein are reagent kits for identifying one or more types of *mycobacterium* in a sample comprising: (a) at least one pair of primers, wherein said primers are configured bind to regions of mycobacteria nucleic acid conserved between two or more types of mycobacteria, and wherein primers are configured to amplify a variable region of mycobacteria nucleic acid; and (b) at least one detectably distinguishable probe set of two hybridization probes which hybridize to adjacent target nucleic acid sequences within the variable region of mycobacteria nucleic acid, comprising: (i) a quencher probe labeled with a non-fluorescent quencher, and (ii) a signaling probe labeled with a fluorescence-emitting dye and a non-fluorescent quencher, wherein the signal probe does not emit fluorescence above background when not hybridized to its target sequence, but emits a fluorescence signal above background upon hybridization to its target sequence in the absence of bound quencher probe, wherein, if both signaling and quencher probes are hybridized to their adjacent target nucleic acid sequences, the non-fluorescent quencher of the quencher probe quenches the signal from the signaling probe. In some embodiments, the melting temperature of the signaling probe in a probe set is higher than the melting temperature of the associated quencher probe. In some embodiments, the fluorescence-emitting dye and said non-fluorescent quenchers of each probe set are capable of interacting by FRET. In some embodiments, each probe set is detectably distinguishable from all other probe sets in said detection reagent kit by (1) melting temperature, (2) emission wavelength of said fluorescence-emitting dye, or (3) a combination thereof. In some embodiments, the detection reagents comprise 5 or more probe sets. In some embodiments, the detection reagents comprise 10 or more probe sets. In some embodiments, a probe set is used to differentiate between mycobacteria of different pathogenicity, species, or antibiotic resistance. In some embodiments, the primers are provided in the proper ration for amplification by LATE-PCR. In some embodiments, probes in at least one detectably distinguishable probe set have melting temperatures with their target nucleic acid sequences below the annealing temperature of at least one primer of the amplification reaction. In some embodiments, reagent kits comprise one or more detectably distinguishable probe sets are configured to hybridize to a region of mycobacteria nucleic acid to differentiate between NTM and MTBC. In some embodiments, reagent kits comprise one or more detectably distinguishable probe sets configured to hybridize to a region of mycobacteria nucleic acid to differentiate between different species of MTBC. In some embodiments, reagent kits comprise three or more detectably distinguishable probe sets configured to hybridize to a region of mycobacteria nucleic acid to differentiate between rifampin-resistant and rifampin-sensitive mycobacteria. In some embodiments, reagent kits comprise one or more detectably distinguishable probe sets configured to hybridize to a region of mycobacteria nucleic acid to differentiate between ethambutol-resistant and ethambutol-sensitive mycobacteria. In some embodiments, reagent kits comprise one or more detectably distinguishable probe sets configured to hybridize to a region of mycobacteria nucleic acid to differentiate between fluoroquinolone-resistant and fluoroquinolone-sensitive mycobacteria. In some embodiments, reagent kits comprise primers and probes configured for: differentiating between NTM and MTBC; (b) differentiating between different species of MTBC; (c) differentiating between isoniazid-resistant and isoniazid-sensitive mycobacteria; (d) differentiating between fluoroquinolone-resistant and fluoroquinolone-sensitive mycobacteria; (e) differentiating between ethambutol-resistant and ethambutol-sensitive mycobacteria; and/or (f) differentiating between rifampin-resistant and rifampin-sensitive mycobacteria. In some embodiments, reagent kits comprise one or more additional oligonucleotides. In some embodiments, additional oligonucleotides are configured to suppress mis-priming during amplification reactions. In some embodiments, additional oligonucleotides are configured to disrupt structural elements within target nucleic acid sequences during amplification reactions or during probing of amplified sequences.

In some embodiments, reagent kits may comprise probe sets, primers, amplification reagents (e.g., amplification buffer, DNA polymerase, control reagents (e.g., positive and negative controls) or any other components that are useful, necessary, or sufficient for practicing any of the methods described herein, as well as instructions, analysis software (e.g., that facilitates data collection, analysis, display, and reporting), computing devices, instruments, or other systems or components.

In some embodiments, provided herein is a homogeneous assay method for analyzing at least one single-stranded nucleic acid mycobacteria target sequence in a sample, comprising: (a) providing a sample comprising at least one mycobacteria nucleic acid target sequence in single-stranded form and for each nucleic acid target sequence at least one detectably distinguishable set of two interacting hybridization probes, each of which hybridizes to the at least one target, comprising: (i) a quencher probe labeled with a non-fluorescent quencher, and (ii) a signaling probe that upon hybridization to the at least one target sequence in the sample in the absence of the quencher probe emits a signal above background, wherein, if both probes are hybridized to the at least one target sequence, the non-fluorescent quencher of the quencher probe quenches the signal from the signaling probe; and (b) analyzing hybridization of the signaling and quenching probes to the at least one mycobacteria target sequence as a function of temperature, the analysis including an effect on each signaling probe due to its associated quencher probe, including but not limited to analyzing signal increase, signal decrease, or both, from each signaling probe.

In some embodiments, signaling probes comprise quenched fluorophores. In some embodiments, the melting temperature of the signaling probe in a probe set is higher than the melting temperature of an associated quenching probe.

In some embodiments, methods provided herein are performed in a single reaction vessel. In some embodiments, methods provided herein are performed in single-vessel (e.g., tube, well, etc.) screening assays to identify which mycobacteria nucleic acid target sequence or sequences from a group of multiple possible target sequences is or are present in a sample. In some embodiments, the group of multiple target sequences comprises a variable sequence flanked by conserved, or at least relatively conserved sequences. In some embodiments, a sample of target sequence in single-stranded form is generated by an amplification method that generates single-stranded amplicons, for example, a non-symmetric polymerase chain reaction (PCR) method, most preferably LATE-PCR. In some embodiments, only a few pairs of primers are used, generally not more than three pairs, preferably not more than two pairs and more preferably only a single pair of primers that hybridize to the flanking sequences. In some embodiments, the primers and at least one set of signaling and quencher probes (e.g., two sets, three sets, etc.) are included in the amplification reaction mixture.

In some embodiments, probe sets (e.g., signaling and quencher probes) are configured to hybridize to mycobacteria variable sequence and to differentiate between multiple mycobacteria target sequences (e.g., in a single sample or mixture). In some embodiments, probes hybridize with different Tm to the variable sequences of the different target sequences. In some embodiment, one or both probes of a probe set (e.g., signaling and/or quencher probes) comprise different degrees of complementarity to the variable regions of the different target sequences. In some embodiments, a signaling probe and/or quencher probe is configured to hybridize to the variable sequence (e.g., overlapping the actual sequence difference) of multiple target sequences (e.g., with different Tm to the different target sequences). In some embodiments, a signaling probe is configured to hybridize to the variable sequence of multiple target sequences (e.g., with different Tm to the different target sequences). In some embodiments, a quencher probe is configured to hybridize to the variable sequence of multiple target sequences (e.g., with different Tm to the different target sequences).

In some embodiments, primers and probes are provided for use in the methods provided herein. In some embodiments, primers provided herein include: SEQ ID NOs: 28, 29, 39, 40, 45, 46, 51, 52, 57, 58, 67, 68, 71, 72, 73, 74, portions thereof, and sequences complementary thereto. In some embodiments, primers provided herein include oligonucleotides with 70% or greater sequence identity with SEQ ID NOs: 28, 29, 39, 40, 45, 46, 51, 52, 57, 58, 67, 68, 71, 72, 73, or 74 (e.g., an oligonucleotide with 70% . . . 75% . . . 80% . . . 90% . . . 95% . . . 98% . . . 99% sequence identity), portions thereof, and sequences complementary thereto. In some embodiments, the present invention provides primers that function substantially similarly to primers provided herein. In some embodiments, probes provided herein include: SEQ ID NOs: 30, 31, 32, 33, 34, 35, 41, 42, 47, 48, 53, 54, 59, 60, 61, 62, 69, 70, portions thereof, and sequences complementary thereto. In some embodiments, probes provided herein include oligonucleotides with 70% or greater sequence identity with SEQ ID NOs: 30, 31, 32, 33, 34, 35, 41, 42, 47, 48, 53, 54, 59, 60, 61, 62, 69, 70, portions thereof, and sequences complementary thereto. In some embodiments, the present invention provides probes that function substantially similarly to probes provided herein. In some embodiments, target sequences for primers and probes provided herein comprise: SEQ ID NOs:36, 37, 38, 43, 44, 49, 50, 55, 56, 63, 64, 75, 76, 77, 78, 79, 80, 81, 82, 83, 84, portions thereof, and sequences complementary thereto. In some embodiments, target sequences comprise sequences 70% or greater sequence identity with SEQ ID NOs:36, 37, 38, 43, 44, 49, 50, 55, 56, 63, 64, 75, 76, 77, 78, 79, 80, 81, 82, 83, 84, portions thereof, and sequences complementary thereto. In some embodiments, target sequences comprise regions of mycobacteria nucleic acid comprising conserved regions flanking a variable region in the genes or promoters of: rpoB, embB, mabA, ahpC, katG, gyrA, 16s rRNA, and gyrB. In some embodiments, primers and probes hybridize to targets in mycobacteria including, but not limited to: *M. tuberculosis, M. africanum, M. intracellulare, M. microti, M. bovis, M. Chelonae, M. Asiaticum, M. Avium, M. fortuitum*. In some embodiments, compositions, methods, and kits provided herein find use in identification, and differentiation of species including: *M. tuberculosis, M. africanum, M. intracellulare, M. microti, M. bovis, M. Chelonae, M. Asiaticum, M. Avium, M. fortuitum*.

In some embodiments, probing and analysis methods provided herein apply to samples containing single-stranded mycobacteria nucleic acid target sequences. Methods include analysis of a single sequence, analysis of two or more sequences in the same strand, analysis of sequences in different strands, and to combinations of the foregoing. A single-stranded nucleic acid target sequence may be a control sequence added to a sample. A nucleic acid target sequence may be DNA, RNA or a mixture of DNA and RNA. It may come from any source. For example, it may occur naturally, or the target sequence may occur in double-stranded form, in which case the single-stranded target sequence is obtained by strand separation and purification. If the single-stranded nucleic acid target sequence is a cDNA sequence, it is obtained from an RNA source by reverse transcription.

In many instances a natural source will not contain a target sequence in sufficient copy number for probing and analysis. In such instances the single-stranded target sequence is obtained by amplification, generally an amplification method that includes exponential amplification. In some embodiments an amplification reaction generates the single-stranded nucleic acid target sequence directly. In some embodiments an amplification reaction generates the target sequence in double-stranded form, in which event the single-stranded target sequence is obtained by strand separation and purification. Useful amplification methods that may be employed include, the polymerase chain reaction (PCR), including symmetric PCR, asymmetric PCR and LATE-PCR, any of which can be combined with reverse transcription for amplifying RNA sequences, NASBA, SDA, TMA, and rolling circle amplification. If the single-stranded nucleic acid target sequence is a cDNA sequence, the amplification method will include reverse transcription, for example, RT-PCR. In some embodiments, when non-symmetric amplification is utilized (e.g., LATE-PCR), probe sets are included in the amplification reaction mixture prior to amplification to avoid contamination.

In some embodiments, probe sets useful in methods provided herein include a signaling probe and an associated quencher probe. The signaling probe is a hybridization probe that emits a detectable signal, preferably a fluorescent signal, when it hybridizes to a single-stranded nucleic acid target sequence in a sample, wherein the signal is quenchable by the associated quencher probe. The quencher probe does not emit visible light energy. Generally, a signaling probe has a covalently bound fluorescent moiety. Signaling probes include probes labeled with fluorophores or other fluorescent moieties, for example, quantum dots. In some embodiments, fluorophore-labeled probes are preferred. One type of signaling probe is a ResonSense® probe. A ResonSense® probe is a single-stranded oligonucleotide labeled with a fluorophore that accepts fluorescence from a DNA dye and reemits visible light at a longer wavelength. Use of a ResonSense® probe involves use of a double-stranded DNA dye, a molecule that becomes fluorescent when it associates with double-stranded DNA, which in this case is the hybrid formed when the probe hybridizes to the single-stranded nucleic acid target sequence. For use of a ResonSense® probe, a DNA dye, for example, SYBR Green or SYBR Gold, is included in the sample containing the single-stranded nucleic acid target sequence along with the probe set or sets. Analysis includes exciting the dye and detection emission from the ResonSense® probe or probes. Unbound signaling probes need not be removed, because they are not directly excited and remain single-stranded. In some embodiments, preferred signaling probes are quenched probes; that is, probes that emit little or no signal when in solution, even if stimulated, but are unquenched and so emit a signal when they hybridize to a single-stranded nucleic acid sequence in a sample being analyzed. Yin-yang probes are quenched signaling probes. A yin-yang probe is a double-stranded probe containing a fluorophore on one strand and an interacting non-fluorescent quencher on the other strand, which is a shorter strand. When a yin-yang probe is in solution at the detection temperature, the fluorophore is quenched. The single-stranded nucleic acid target sequence out-competes the quencher-labeled strand for binding to the fluorophore-labeled strand. Consequently, the fluorophore-labeled strand hybridizes to the single-stranded nucleic acid target sequence and signals. Signaling probes for some embodiments provided herein are molecular beacon probes, single-stranded hairpin-forming oligonucleotides bearing a fluorescer, typically a fluorophore, on one end, and a quencher, typically a non-fluorescent chromophore, on the other end. In some embodiments, provided herein are single stranded oligonucleotides with any suitable type of secondary structure, bearing a fluorescence-emitting dye on one end and a quencher on the other end (molecular-beacon-type probes). Various signaling probes for use in embodiments herein comprise varying degrees of secondary structure (e.g., different lengths of hairpin (e.g., 2 base pairs, 3, base pairs, 4 base pairs, 5 base pairs, etc.). When molecular beacon probes, and other similar types of probes, are in solution, they assume a conformation wherein the quencher interacts with the fluorescer, and the probe is dark (e.g., hairpin conformation, closed conformation). When the probe hybridizes to its target, however, it is forced into an open conformation in which the fluorescer is separated from the quencher, and the probe signals.

In quenched signaling probes, quenching may be achieved by any mechanism, typically by FRET (Fluorescence Resonance Energy Transfer) between a fluorophore and a non-fluorescent quenching moiety or by contact quenching. In some embodiments, preferred signaling probes are dark or very nearly dark in solution to minimize background fluorescence. Contact quenching more generally achieves this objective, although FRET quenching is adequate with some fluorophore-quencher combinations and probe constructions.

The quencher probe of a probe set comprises of consists of a nucleic acid strand comprising a non-fluorescent quencher. In some embodiments, the quencher is, for example, a non-fluorescent chromophore such a dabcyl or a Black Hole Quencher (Black Hole Quenchers, available from Biosearch Technologies, are a suite of quenchers, one or another of which is recommended by the manufacturer for use with a particular fluorophore). In some embodiments, preferred quenching probes include a non-fluorescent chromophore. In some embodiments, quenchers are Black Hole Quenchers. The quencher probe of a set hybridizes to the single-stranded nucleic acid target sequence adjacent to or near the signaling probe such that when both are hybridized, the quencher probe quenches, or renders dark, the signaling probe. Quenching may be by fluorescence resonance energy transfer (FRET) or by touching ("collisional quenching" or "contact quenching").

FIG. 1 depicts an embodiment that illustrates the functioning of probe sets in analytical methods provided herein. In this embodiment there are two probe sets, probes 2, 4 and probes 6, 8. Probe 2 is a signaling probe, a molecular-beacon-type probe bearing fluorophore 3. Probe 6 is also a signaling probe, a molecular-beacon-type probe bearing fluorophore 7. Fluorophores 3, 7 are the same. Probes 4, 8 are quencher probes labeled only with Black Hole Quenchers 5 and 9, respectively. The melting temperatures (Tm's) of the probe-target hybrids (probes hybridized to single-stranded nucleic acid target sequence 1) are as follows: Tm probe 2>Tm probe 4>Tm probe 6>Tm probe 8. As the temperature of the sample is lowered from a high temperature at which no probes are bound, probes 2, 4, 6 and 8 bind to single-stranded nucleic acid target sequence 1 according to their hybridization characteristics. Probe 2, a signaling probe, binds first. FIG. 1, Panel A depicts probe 2 hybridized to sequence 1. As the temperature of the sample continues to be lowered, quencher probe 4 binds next, adjacent to probe 2 such that quencher 5 and fluorophore 3 are near to one another or touching. FIG. 1, Panel B depicts probe 4 hybridized to single-stranded nucleic acid sequence 1 adjacent to probe 2. At this point probe 2 is dark, or at least nearly dark. If, however, signaling probe 6 has begun to bind, it will emit fluorescence independently of probes 2, 4.

FIG. 1, Panel C depicts probe 6 hybridized to single-stranded target sequence 1 adjacent to probe 4. Finally as the temperature continues to be lowered, probe 8 will bind, and its quencher 9 will quench fluorescence emission from fluorophore 7 of probe 6. FIG. 1, Panel D depicts probe 8 hybridized adjacent to probe 6. Analysis by hybridization is shown in FIG. 1, Panel E, which depicts the increase and decrease of fluorescence from fluorophores 3, 7 as a function of temperature. Such curves can be obtained as annealing (hybridization) curves as the temperature is lowered, or can be obtained as melting curves as the temperature is increased. As the sample temperature is lowered from 70° C., fluorescence curve 10 in Panel E first rises as probe 2 hybridizes to single-stranded nucleic acid sequence 1, then decreases as probe 4 binds, then increases again as probe 6 hybridizes, and finally decreases to a very low level as probe 8 hybridizes. One can deduce from curve 10 that each signaling probe has a higher Tm than its associated quencher probe.

Signaling and quenching probes useful in methods provided herein are typically mismatch tolerant (capable of hybridizing to single-stranded nucleic acid target sequences containing one or more mismatched nucleotides, or deletions or additions). In some embodiments, mycobacteria are differentiated by the unique temperature-dependent fluorescence signatures generated by mismatches between probes and target sequences. In some embodiments, probes may be allele-specific (capable of hybridizing only to a perfectly complementary single-stranded nucleic acid target sequence in the method). In some embodiments, one probe of a set may be allele-specific; and the other probe, mismatch tolerant. Experiments conducted during development of embodiments provided herein demonstrated that secondary structure of a target strand outside the sequences to which probes hybridize can affect the results of annealing or melting analysis. Accordingly, in some embodiments, not every nucleotide in a nucleic acid target sequence needs to be hybridized to a probe. For example, if the target sequence contains a hairpin, the corresponding probe can be designed in some cases to hybridize across the base of the hairpin, excluding the hairpin sequence. In preferred embodiments, both the signaling and quencher probes of a probe set are mismatch tolerant. In some embodiments, a probe set may include an allele-specific signaling probe and an allele-specific quencher probe, a mismatch-tolerant signaling probe and a mismatch-tolerant quencher probe, an allele-specific signaling probe and a mismatch-tolerant quencher probe, or a mismatch-tolerant signaling probe and an allele-specific quencher probe. A mismatch-tolerant probe may be perfectly complementary to one variant of a variable target sequence, or it may be a consensus probe that is not perfectly complementary to any variant. Multiple probe sets may include combinations of sets of any of the foregoing types. Additionally, analytical methods provided herein may utilize one or more signaling/quenching probe sets in combination with one or more conventional probes that signal upon hybridization to their target, for example, molecular beacon probes.

In some embodiments, unlabeled oligonucleotides configured to bind to regions at or near the target sequences for primers, signaling probes, or quencher probes. In some embodiments, these silent probes disrupt secondary structure within or near the target sequences and assist other probes in binding to target sequences at suitable Tm for subsequent analysis. In some embodiments, unlabeled oligonucleotides which serve as "openers" of structural elements (e.g., secondary structural elements) are provided.

Probes useful in the methods provided herein may be DNA, RNA, or a combination of DNA and RNA. They may include non-natural nucleotides, for example, PNA, LNA, or 2' o-methyl ribonucleotides. They may include non-natural internucleotide linkages, for example, phosphorothioate linkages. The length of a particular probe depends upon its desired melting temperature (Tm), whether it is to be allele-specific or mismatch tolerant, and its composition, for example, the GC content of a DNA probe.

In some embodiments, each signaling probe has a separate quenching probe associated with it. In some embodiments, however one probe may be a part of two probe sets. For example, a quencher probe may be labeled with a quencher at each end, whereby the ends interact with different signaling probes, in which case three probes comprise two probe sets. Also, some embodiments may utilize both ends of a quenched signaling probe, for example, a molecular beacon signaling probe having a fluorophore on one end and a quencher on the other end. The fluorophore interacts with a quencher probe, comprising one set, and the quencher interacts with a signaling probe, comprising another set.

For analysis of a sample containing one or more types of mycobacteria or suspected of containing one or more types of mycobacteria, the probe sets that are used are detectably distinguishable, for example by emission wavelength (color) or melting temperature (Tm). Making a probe set distinguishable by Tm from other probe sets is accomplished in any suitable way. For example, in some embodiments, all signaling probes in an assay have different Tm's. Alternatively, in some embodiments, all signaling probes have the same Tm, but the quencher probes have different Tm's. In some embodiments, probe sets are distinguishable by a combination of the signaling probe Tm and quenching probe Tm. Fluorescence detectors can commonly resolve 1-10 differently colored fluorophores. Therefore assays utilizing method provided herein can make use of up to 10 fluorophores (e.g., 1, 2, 3, 4, 5, 6, 7, 8, 9, 10, or more if fluorescence detectors allow). The same fluorescence emitter, for example, the same fluorophore, can be used on more than one signaling probe for a sample, if the signaling probe's can be differentiated for detection by their melting temperatures. In assays provided herein, Tm's should be separated by at least 2° C., preferably by at least 5° C. and, in certain embodiments by at least 10° C. Available temperature space constrains the use of multiple signaling probes having the same fluorophore. If an assay is designed for annealing and/or melt analysis over a range of 80° C. to 20° C., for example, one can utilize more probe sets sharing a color than one can use in an assay designed for such analysis over a range of 70° C. to 40° C., for which one may be able to use only 3-5 probe sets sharing a color. Using four colors and only two probe sets sharing each color, a four-color detector becomes equivalent to an eight-color detector used with eight probes distinguishable by color only. Use of three probe sets sharing each of four colors, twelve different probes sets become distinguishable.

In some embodiments, it is preferred that quencher probes have lower Tm's than their associated signaling probes. With that relationship, the signaling probe emits a temperature-dependent signal through the annealing temperature range of both probes of the set as the temperature of the solution is lowered for an annealing curve analysis, and through the melting temperature range of both probes of the set as the temperature of the solution is raised for a melting curve analysis. If, on the other hand, the quencher probe of a probe set has a higher Tm than its associated signaling probe, the signaling probe's emission is quenched through the annealing temperature range and melting temperature range of both probes of the set, and no fluorescent signal is emitted for detection. This can be ascertained by examination of the annealing curve or the melting curve. The lack of signal provides less information about the single-stranded nucleic acid target sequence than does a curve of the probe's fluorescence as a function of temperature. In some embodiments, when mismatch-tolerant probes are used for analysis of a variable sequence, quencher probes with lower Tm's than their associated signaling probes are used with respect to all or all but one of the target sequence variants. If a quencher probe has a higher Tm against only one variant, signal failure will reveal that variant, as long as failure of the sample to include the single-stranded nucleic acid target sequence (particularly failure of an amplification reaction) is otherwise accounted for by a control or by another probe set for the single-stranded nucleic acid target sequence. Similarly, if not all variants are known, such signal failure will reveal the presence of an unknown variant. In some embodiments, it is preferred that in an assay utilizing multiple probe sets for at least one nucleic acid target sequence, the quencher probe of at least one probe set has a lower Tm than its associated signaling probe.

Melting temperature, Tm, means the temperature at which a nucleic acid hybrid, for example, a probe-target hybrid or primer-target hybrid, is 50% double-stranded and 50% single-stranded. For a particular assay the relevant Tm's may be measured. Tm's may also be calculated utilizing known techniques. In some embodiments, preferred techniques are based on the "nearest neighbor" method (Santa Lucia, J. (1998), PNAS (USA) 95: 1460-1465; and Allawi, H. T. and Santa Lucia, J. (1997), Biochem. 36: 10581-10594; herein incorporated by reference in their entireties). Computer programs utilizing the "nearest neighbor" formula are available for use in calculating probe and primer Tm's against perfectly complementary target sequences and against mismatched target sequences. In this application the Tm of a primer or probe is sometimes given with respect to an identified sequence to which it hybridizes. However, if such a sequence is not given, for mismatch-tolerant probes that are perfectly complementary to one variant of a single-stranded nucleic acid target sequence, the Tm is the Tm against the perfectly complementary variant. In many embodiments there will be a target sequence that is perfectly complementary to the probe. However, methods may utilize one or more mismatch-tolerant primer or probes that are "consensus primers" or "consensus probes." A consensus primer or probe is a primer or probe that is not complementary to any variant target sequence or, if not all possible target sequences are, to any expected or known sequence. A consensus primer is useful to prime multiple variants of a target sequence at a chosen amplification annealing temperature. A consensus probe is useful to shrink the temperature space needed for analysis of multiple variants. For a consensus primer or probe, if no corresponding target sequence is given, the Tm refers to the highest Tm against known variants, which allows for the possibility that an unknown variant may be more complementary to the primer or probe and, thus, have higher primer-target Tm or probe-target Tm.

Assays provided herein may utilize probe concentrations that are greater than or less than target nucleic acid concentration. The probe concentrations are known on the basis of information provided by the probe manufacturer. In the case of target sequences that are not amplified, target concentrations are known on the basis of direct or indirect counting of the number of cells, nuclei, chromosomes, or molecules are known to be present in the sample, as well as by knowing the expected number of targets sequences usually present per cell, nucleus, chromosome, or molecule. In the case of target sequences that are amplified, there are a number of ways to establish how many copies of a target sequence have been generated over the course of an amplification reaction. For example, in the case of a LATE-PCR amplification reaction the number of single-stranded amplicons can be calculated as follows: using a signaling probe without a quencher (in the case of quenched signaling probe that means the probe minus the quencher) in a limiting concentration such as 50 nM and its corresponding quencher probe in excess amount such as 150 nM, the number of cycles it takes to decrease the fluorescence to zero (or, in practical terms, to its minimal background level) is proportional to the rate of amplification of single-stranded amplicons. When fluorescence reaches zero (minimal background level), all of the signaling probes have found their target, and the concentration of the amplicons exceeds that of the signaling probe. In certain embodiments an amplification reaction may be continued until the amplicon being produced reaches a "terminal concentration." Experiments conducted during development of embodiments provided herein demonstrated that a LATE-PCR amplification begun with differing amounts of target tends to produce eventually the same maximum concentration of amplicon (the "terminal concentration"), even though amplification begun with a high starting amount of target reaches that maximum in fewer cycles than does the amplification begun with a low starting amount of target. To achieve the terminal concentration beginning with a low amount of target may require extending the amplification through 70 or even 80 cycles.

Some embodiments utilize probe sets in which the concentration of the signaling probe is lower than the concentration of its associated quencher probe. This ensures that, when both probes are hybridized to their at least one nuclei acid target sequence, the signaling probe is quenched to the greatest possible degree, thereby minimizing background fluorescence. It will be appreciated that background fluorescence in an assay is the cumulated background of each signaling probe of a given color and that probes of a different color may contribute further to background signal.

Methods provided herein include analyzing the hybridization of probe sets to single-stranded mycobacteria nucleic acid target sequences. In methods provided herein, hybridization of signaling probes and quencher probes as a function of temperature are analyzed for the purpose of identifying, characterizing or otherwise analyzing at least one mycobacteria nucleic acid target sequence in a sample. In some embodiments analysis includes obtaining a curve or, if multiple colors are used, curves of signals from signaling probes as the temperature of a sample is lowered (see FIG. 1, Panel E) or obtaining a curve or curves of signals as the sample temperature is raised, or both. It is known that the shapes of the two types of curves are not necessarily identical due to secondary structures. Either or both of those curves can be compared to a previously established curve for a known single-stranded nucleic acid target sequence as part of the analysis, for example, identifying the single-stranded nucleic acid target sequence being probed. Derivative curves can also be utilized to obtain, for example, the Tm of a signaling probe against a nucleic acid target sequence. It is not always necessary, and it may not be desirable, to utilize entire fluorescence curves or their derivatives. In certain embodiments analysis of the hybridization of signaling probes and quencher probes includes obtaining fluorescence readings at one or several temperatures as the sample temperature is lowered or raised, where those readings reflect an effect on each signaling probe due to its associated quencher probe. For example, if it is desired to distinguish among known variants of a target sequence, and one learns from hybridization curves of variants that fluorescence at two temperatures distinguishes the variants, one need acquire fluorescence at only those two temperatures for either direct comparison or for calculation of ratios that can be compared. In most embodiments the analysis will include signal increase, signal decrease, or both, from each signaling probe.

In some embodiments, fluorescence readings using a particular probe set over a range of temperatures generates a temperature-dependent fluorescence signature. A temperature-dependent fluorescence signature may comprise curves, data points, peaks, or other means of displaying and/or analyzing an assay or sample. In some embodiments, analysis of temperature-dependent fluorescence signatures identifies and/or differentiates mycobacteria. In some embodiments, analysis is performed by a user. In some embodiments, analysis is performed by analysis software on a computer or other device.

In some embodiments, methods provided herein include nucleic acid amplification. Some preferred methods are those which generate the target sequence or sequences in single-stranded form. LATE-PCR amplification of DNA sequences or RNA sequences (RT-LATE-PCR) is especially preferred in some embodiments. LATE-PCR amplifications and amplification assays are described in, for example, European patent EP 1,468,114 and corresponding U.S. Pat. No. 7,198,897; published European patent application EP 1805199 A2; Sanchez et al. (2004) Proc. Nat. Acad. Sci. (USA) 101: 1933-1938; and Pierce et al. (2005) Proc. Natl. Acad. Sci. (USA) 102: 8609-8614. All of these references are hereby incorporated by reference in their entireties. LATE-PCR is a non-symmetric DNA amplification method employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce fluorescently detectable double-stranded amplicon. After the Limiting Primer is exhausted, amplification continues for a desired number of cycles to produce single-stranded product using only the Excess Primer, referred to herein as the Excess Primer strand. LATE-PCR takes into account the concentration-adjusted melting temperature of the Limiting Primer at the start of amplification, $Tm_{[0]}^L$, the concentration-adjusted melting temperature of the Excess Primer at the start of amplification, $Tm_{[0]}^X$, and the melting temperature of the single-stranded amplification product ("amplicon"), $Tm_A$. For LATE-PCR primers, $Tm_{[0]}$ can be determined empirically, as is necessary when non-natural nucleotides are used, or calculated according to the "nearest neighbor" method (Santa Lucia, J. (1998), PNAS (USA) 95: 1460-1465; and Allawi, H. T. and Santa Lucia, J. (1997), Biochem. 36: 10581-10594) using a salt concentration adjustment, which in our amplifications is generally 0.07 M monovalent cation concentration. For LATE-PCR the melting temperature of the amplicon is calculated utilizing the formula: Tm=81.5+0.41 (% G+% C)−500/L+16.6 log [M]/(1+0.7 [M]), where L is the length in nucleotides and [M] is the molar concentration of monovalent cations. Melting temperatures of linear, or random-coil, probes can be calculated as for primers. Melting temperatures of structured probes, for example molecular beacon probes, can be determined empirically or can be approximated as the Tm of the portion (the loop or the loop plus a portion of the stem) that hybridizes to the amplicon. In a LATE-PCR amplification reaction $Tm_{[0]}^L$ is preferably not more than 5° C. below $Tm_{[0]}^X$, more preferably at least as high and even more preferably 3-10° C. higher, and $Tm_A$ is preferably not more than 25° C. higher than $Tm_{[0]}^X$, and for some preferred embodiments preferably not more than about 18° C. higher.

LATE-PCR is a non-symmetric PCR amplification that, among other advantages, provides a large "temperature space" in which actions may be taken. See WO 03/054233 and Sanchez et al. (2004), cited above. Certain embodiments of LATE-PCR amplifications include the use of hybridization probes, in this case sets of signaling and quencher probes, whose Tm's are below, more preferably at least 5° C. below, the mean primer annealing temperature during exponential amplification after the first few cycles. Sets of signaling and quencher probes are included in LATE-PCR amplification mixtures prior to the start of amplification. A DNA dye, if used, can also be incorporated into the reaction mixture prior to the start of amplification.

In some embodiments, samples which find use in the present invention include clinical samples, diagnostic samples, research samples, environmental samples, etc. are provided. In some embodiments, samples require processing by one or more techniques understood in the art prior to use in methods described herein.

BRIEF DESCRIPTION OF THE DRAWINGS

FIG. 1, Panel E, shows the fluorescence versus temperature of the sample.

FIG. 9 discloses Probe 1 as SEQ ID NO: 6, Probe 2 as SEQ ID NO: 7, Probe 3 as SEQ ID NO: 8, Probe 4 as SEQ ID NO: 9, Probe 5 as SEQ ID NO: 10, Probe 6 as SEQ ID NO: 11, the underlined portion of the full-length sequence SEQ ID NO: 38 as SEQ ID NO: 2 and the sequence aligned with the last portion of the full-length sequence SEQ ID NO: 38 as SEQ ID NO: 28.

FIG. 12 discloses Probe 1 as SEQ ID NO: 16, Probe 2 as SEQ ID NO: 17, Probe 3 as SEQ ID NO: 18, Probe 4 as SEQ ID NO: 19, the underlined portion of the full-length sequence SEQ ID NO: 14 as SEQ ID NO: 13 and the sequence aligned with the last portion of the full-length sequence SEQ ID NO: 14 as SEQ ID NO: 12.

FIG. 13 discloses Probe 1 as SEQ ID NO: 25, Probe 2 as SEQ ID NO: 26, the underlined portion of the full-length sequence SEQ ID NO: 22 as SEQ ID NO: 95 and the sequence aligned with the last portion of the full-length sequence SEQ ID NO: 22 as SEQ ID NO: 20.

FIG. 15 discloses the 16s MTC sequence as SEQ ID NO: 55, 16s M. intra sequence as SEQ ID NO: 56, rpoB Mtb sequence as SEQ ID NO: 90, rpoB Mavium sequence as SEQ ID NO: 91, katG Mtb sequence as SEQ ID NO: 92, katG Mavium sequence as SEQ ID NO: 93, gyrB Mtb sequence as SEQ ID NO: 63 and gyrB Mintra sequence as SEQ ID NO: 94.

DETAILED DESCRIPTION

Figure 1:
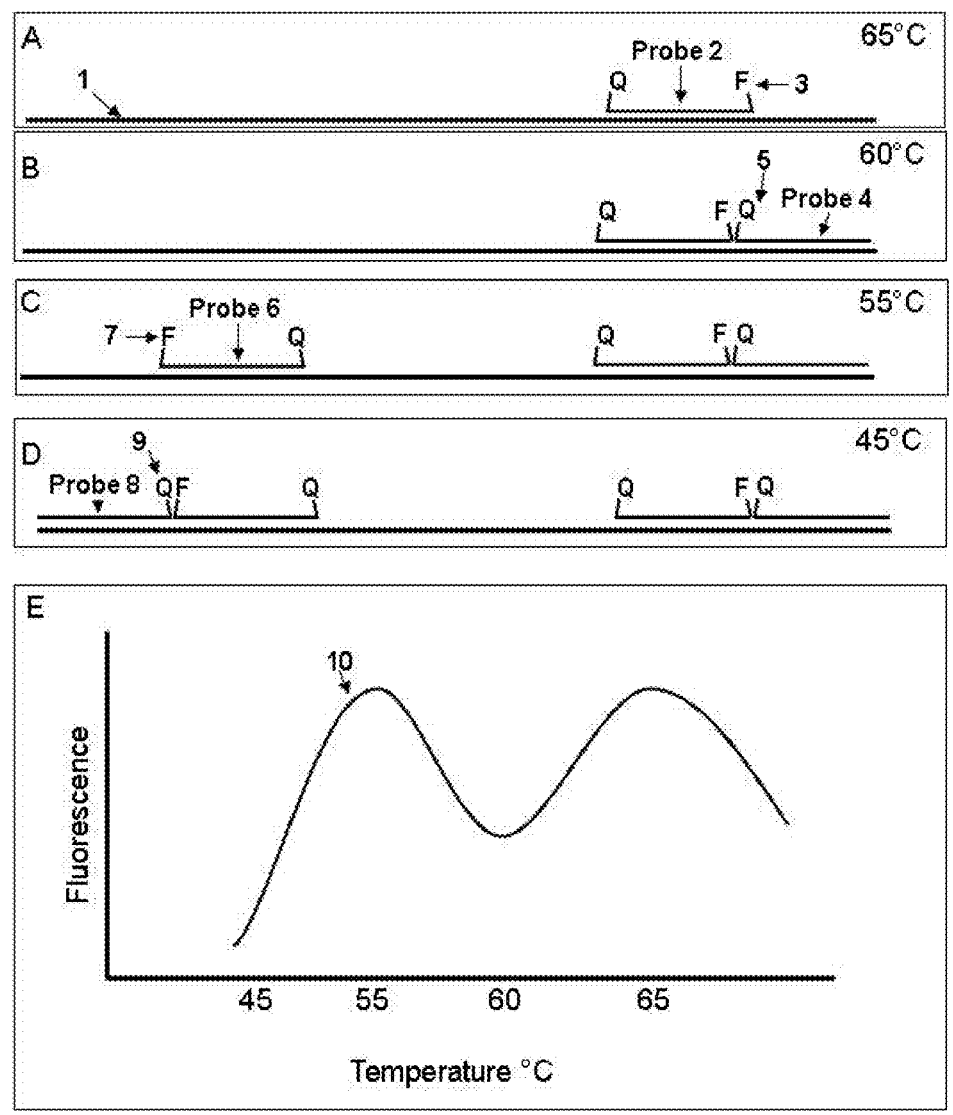
FIG. 1, Panels A-D are schematics showing hybridization of two sets of signaling and quencher probes to a single-stranded nucleic acid target sequence in a sample as a function of temperature.

Provided herein are compositions (e.g., reagents, reactions mixtures, etc.), methods (e.g., research, screening, diagnostic), and systems (e.g., kits, data collection and analysis) for analysis of mycobacteria. In particular, provided herein are compositions, methods, and systems that permit sensitive and specific detection of one or more desired *mycobacterium* nucleic acid molecules in simple and complex samples, including samples containing multiple different species of *mycobacterium* of mixed drug resistance profiles. In some embodiments, multiplex, single-tube reactions are provided that can simultaneously identify and distinguish multiple different *mycobacterium* species and drug resistance profiles in complex samples using fast and efficient assays and detection equipment.

For example, provided herein is a set of single-tube homogeneous multiplexed assays for detection and analysis of various species of mycobacteria, including various strains of *M. tuberculosis*, as well as whether such species and strains are sensitive or resistant to a variety of antibiotics. In some embodiments, assays provided herein utilize LATE-PCR (U.S. Pat. No. 7,198,897; incorporated herein by reference in its entirety), PRIMESAFE II (PRIMESAFE is a trademark of Smiths Detection Inc.)(U.S. Patent Application No. 20080193934; incorporated herein by reference in its entirety), and Lights-On/Lights-Off probe sets (International Publication No. WO/2011/050173; incorporated herein by reference in its entirety).

The methods, compositions, and kits provided herein provide diagnostically relevant information as well as a basis for treatment of patients who exhibit pulmonary infections that may due to mycobacterial infections. In some embodiments, assays provided herein determine whether a sample contains *mycobacterium*. In some embodiments, assays provided herein determine whether a pulmonary infection contains *mycobacterium*. In some embodiments, assays provided herein determine whether a *mycobacterium* in a sample or infection is a member of the *Mycobacterium Tuberculosis* Complex (MTBC) or is a non-Tuberculosis Mycobacterium (NTM). In some embodiments, assays provided herein determine if an NTM is *M. intracellulare, M. avium, M. kansasii,* or *M. leprae* or some other species. In some embodiments, assays provided herein determine if an MTBC is *M. africanum, M. bovis, M. canettii, M. microti,* or *M. tuberculosis*. In some embodiments, assays provided herein determine if a sample contains, or an infection is due to, a mixture of NTMs and MTBCs. In some embodiments, assays provided herein determine if a sample contains antibiotic-sensitive *M. tuberculosis*, antibiotic-resistant *M. tuberculosis*, or both. In some embodiments, assays provided herein determine which antibiotics *M. tuberculosis* in a sample resistant to, and at what dose.

Compositions, kits, and methods provided herein provide sensitive and robust amplification starting with low initial numbers of target sequences (e.g., either absolute numbers or relative to non-target sequences). In some embodiments, amplified target sequences which are substantially longer than individual fluorescent hybridization probes are analyzed using sets of probes which use the same colored fluorophore. In some embodiments, neutral mutations which do not cause drug resistance are distinguished from mutations which do cause drug resistance. In some embodiments, each of the different possible mutations that cause drug resistance is distinguished from the others. In some embodiments, drug resistance mutants are detected in genomic DNA mixtures comprised wild type drug sensitive genomes and mutant drug resistant mutants.

In some embodiments, signaling probes and quenching probes for use with mycobacteria-identification assays are provided. Signaling probes and quenching probes are typically mismatch tolerant. A mismatch-tolerant probe hybridizes in the assay, not only to a target sequence that is perfectly complementary to the probe, but also to variations of the target sequence that contain one or more mismatches due to substitutions, additions or deletions. For mismatch-tolerant probes, the greater the variation of the target from perfect complementarity, the lower the Tm of the probe-target hybrid. In some embodiments, sequence-specific probes are employed. A sequence-specific probe hybridizes in the assay only to a target sequence that is perfectly complementary to the probe (e.g., at a given temperature). In some embodiments, combinations of sequence-specific and mismatch-tolerant probes are employed in an assay. If a probe is sequence-specific, its lack of hybridization will be apparent in the melt curve and the derivative curve. For example, if a signaling probe hybridizes, causing an increase in fluorescence, but its associated quencher probe does not hybridize, fluorescence will not decrease as the temperature is lowered through the Tm of the quencher probe, revealing that the quencher probe did not hybridize and indicating a target mutation in the sequence complementary to the quencher probe. While this result indicates a mutation in the target sequence for the quencher probe, it does not allow for determination of which one of several possible mutations of that sequence is present. In some embodiments, it is preferable that the associated quencher probe be mismatch tolerant, if the assay is to provide differentiation of different mutations, distinguished by their different effects on the melting curve (and derivative curve) due to differing Tm effects of different mutations.

In some embodiments, a signaling probe of a set has a higher Tm with respect to the single-stranded nucleic acid target sequence than does its associated quencher probe. With that relationship, as a sample is subjected to melt analysis, for example, as temperature is increased signal first increases as the quencher probe melts off and then decreases as the signaling probe melts off. With the opposite relationship, signal remains quenched as the lower Tm signaling probe melts off and does not then increase as the higher Tm quencher probe melts off. The preferred relationship thus provides more information. In some embodiments, it is preferred that the quencher probe of a set reduces the signal from its associated signaling probe to a very large extent. In such embodiments, it is preferred that the concentration of the quencher probe equal or exceed the concentration of the signaling probe. In order to maximize signal amplitude, certain embodiments utilize probe concentrations that are in excess with respect to the single-stranded nucleic acid target sequence, thereby ensuring that all or nearly all copies of the target sequence will have hybridized probes.

Methods provided herein include the use of a single set of interacting signaling and quencher probes. Methods also include the use multiple sets of interacting signaling and quencher probes, wherein each signaling probe is detectably distinguishable from the others. Distinction of fluorescent probes may be by color (emission wavelength), by Tm, or by a combination of color and Tm. Multiple sets of interacting probes may be used to interrogate a single target sequence or multiple target sequences in a sample, including multiple target sequences on the same target strand or multiple target sequences on different strands. Multiplex detection of multiple target sequences may utilize, for example, one or more sets of signaling/quencher probes specific to each target sequence. In some embodiments, multiplex methods utilize a different fluorescent color for each target sequence. Certain embodiments utilize the same color for two different target sequences, available temperature space permitting.

In some embodiments, methods comprise analyzing hybridization of signaling/quencher probe sets to one or more single-stranded mycobacteria nucleic acid target sequences as a function of temperature. Signal, preferably fluorescent signal, from the signaling probe or probes may be acquired as the temperature of a sample is decreased (annealing) or increased (melting). Analysis may include acquisition of a complete annealing or melting curve, including both increasing and decreasing signals from each signaling probe, as is illustrated in FIG. 1, Panel E. Alternatively, analysis can be based only on signal increase or signal decrease. Analysis may utilize only signals at select temperatures rather than at all temperatures pertinent to annealing or melting. Analysis may include comparison of the hybridization of an unknown single-stranded nucleic acid target sequence to hybridization of known target sequences that have been previously established, for example, a compilation of melting curves for known species or a table of digitized data for known species.

In methods provided herein, one or more single-stranded mycobacteria nucleic acid target sequences to be analyzed may be provided by nucleic acid amplification, generally exponential amplification. Any suitable nucleic amplification method may be used. Preferred amplification methods are those that generate amplified product (amplicon) in single-stranded form so that removal of complementary strands from the single-stranded target sequences to be analyzed is not required. Probe sets may be included in such amplification reaction mixtures prior to the start of amplification so that reaction vessels containing amplified product need not be opened. When amplification proceeds in the presence of probe sets, it is preferred that the system be designed such that the probes do not interfere with amplification. In some embodiments a non-symmetric PCR method such as asymmetric PCR or, LATE-PCR is utilized to generate single-stranded copies. PCR amplification may be combined with reverse transcription to generate amplicons from RNA targets. For example, reverse transcription may be combined with LATE-PCR to generate DNA amplicons corresponding to RNA targets or the complements of RNA targets. In some embodiments, amplification methods that generate only double-stranded amplicons are not preferred, because isolation of target sequences in single-stranded form is required, and melt-curve analysis is more difficult with double-stranded amplicons due to the tendency of the two amplicons to collapse and eject hybridization probes. In some embodiments, methods provided herein do not utilize generation of detectable signal by digestion of signaling probes, such as occurs in 5' nuclease amplification assays. In a PCR amplification reaction, for example, avoidance of probe digestion may be accomplished either by using probes whose Tm's are below the primer-extension temperature, by using probes such as those comprising 2' O-methyl ribonucleotides that resist degradation by DNA polymerases, or by using DNA polymerases that lack 5' exonuclease activity. Avoidance of probe interference with amplification reactions is accomplished by utilizing probes whose Tm's are below the primer-extension temperature such that the probes are melted off their complementary sequences during primer extension and, most preferably, during primer annealing, at least primer annealing after the first few cycles of amplification. For example, in the amplification assay method of Example 1, the LATE-PCR amplification method utilized two-step PCR with a primer-annealing/primer-extension temperature of 75° C. in the presence of a set of mismatch-tolerant molecular beacon probes having Tm's against the wild-type target sequence (to which the probes were perfectly complementary) ranging from 75° C. to 50° C., which ensured that none of the probes interfered significantly with amplification of the target sequence.

In LATE-PCR amplification, for example, the Excess Primer strand is the single-stranded amplicon to which probe sets hybridize. It therefore is or contains the single-stranded nucleic acid sequence that is analyzed. Its 5' end is the Excess Primer, and its 3' end is the complement of the Limiting Primer. If the sequence to be analyzed lies between the Excess Primer and the Limiting Primer, the starting sequence that is amplified and the Excess Primer strand both contain that sequence. If in the starting sequence to be amplified the sequence desired to be analyzed includes a portion of either priming region, it is required that the primer be perfectly complementary to that portion so that the Excess Primer strand contain the desired sequence. Primers need not be perfectly complementary to other portions of the priming regions. Certain embodiments of methods provide single-stranded nucleic acid target sequence to be analyzed by amplification reactions that utilize "consensus primers' that are not perfectly complementary to the starting sequence to be amplified, and care is taken to ensure that the Excess Primer strand, which is or contains the single-stranded target sequence that is actually analyzed, contains the desired sequence.

In some embodiments, assays provided herein utilize PRIMESAFE II (described in U.S. Patent Application No. 20080193934; herein incorporated by reference in its entirety). PRIMESAFE II is a class of reagents added to PCR reactions to suppress mis-priming. PRIMESAFE II reagents are comprised of linear oligonucleotides that are chemically modified at their 5' and or 3' ends. In some embodiments, primesafe reagents used herein include SEQ ID NO: 65 and SEQ ID NO.:66. In some embodiments, the assays described here make use of a formulation of PRIMESAFE II that has two strands, the first strand of which is modified at both the 5'end and the 3'end by covalent linkage of dabcyl moieties, the second strand of which is complementary to said first strand and is chemically modified by addition of dabcyl moieties at both the 5' end and the 3'end.

Figure 2:
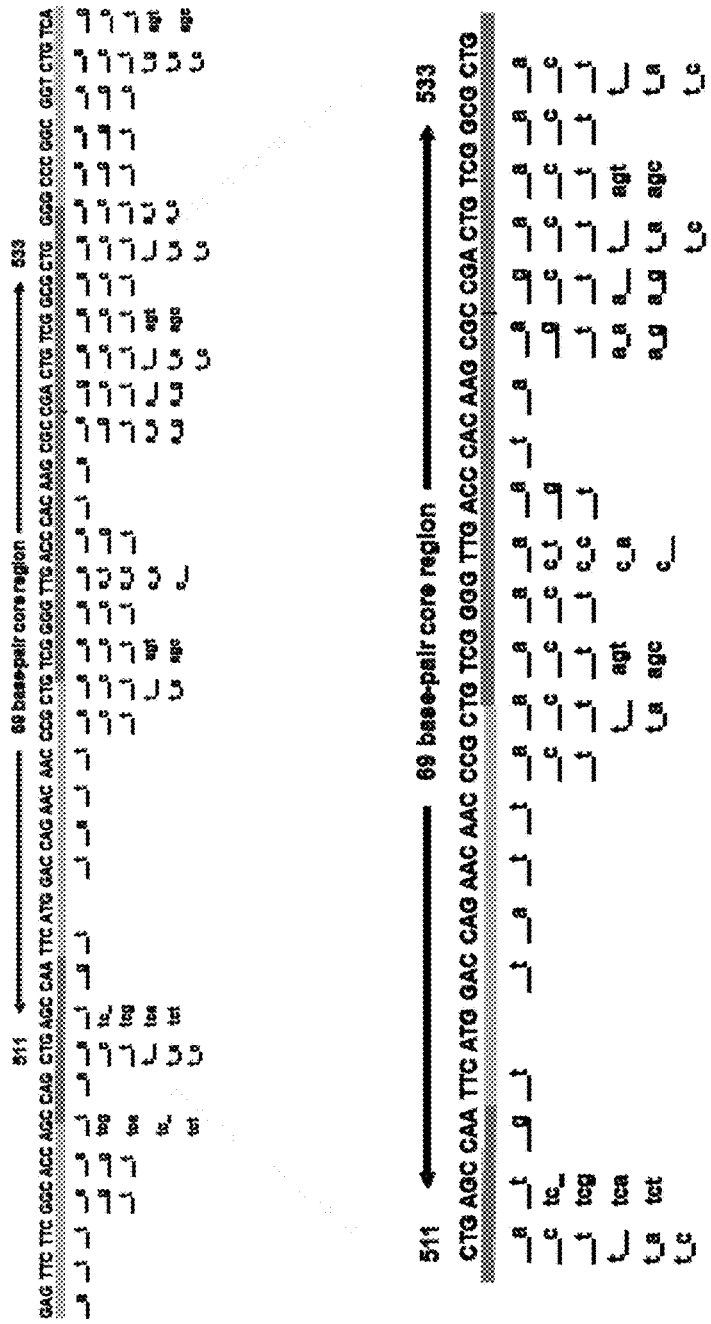
FIG. 2 illustrates possible neutral mutations which may exist in the rpoB gene target. Figure discloses SEQ ID NOS 96 and 85 and bases 22-90 of SEQ ID NOS 96 and 85, respectively, in order of appearance.
Figure 3:
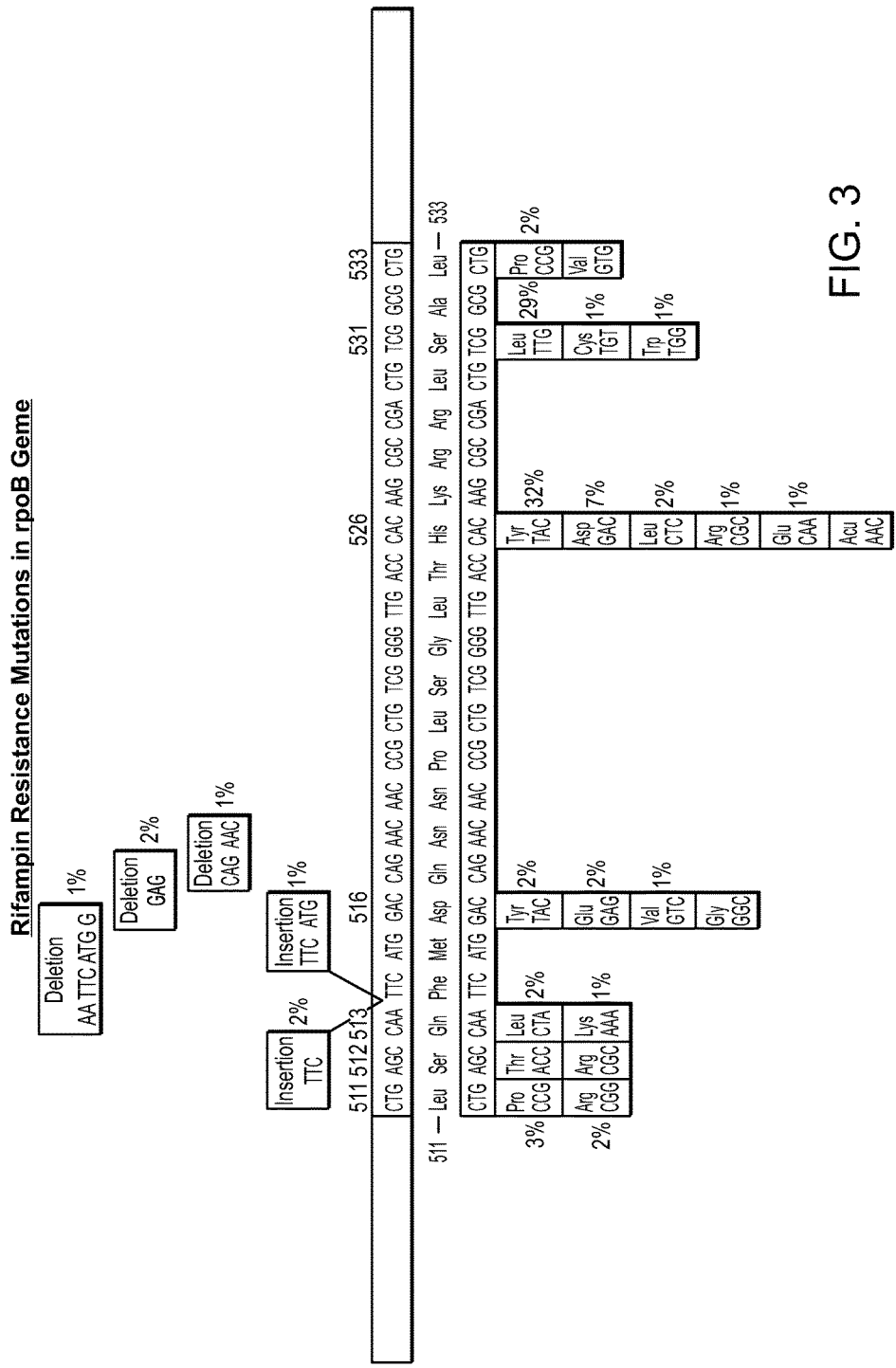
FIG. 3 illustrates drug resistance mutations in the rpoB gene target FIG. 3 discloses the first full-length oligonucleotide as SEQ ID NO: 86, the corresponding coded protein described beneath as SEQ ID NO: 87, the second full-length oligonucleotide as SEQ ID NO: 88 and the corresponding coded protein described beneath as SEQ ID NO: 89.

An aspect of embodiments provided herein is the capability to identify drug resistant strains of *mycobacterium*, differentiating from drug-sensitive strains which may contain neutral mutations. FIG. 2 illustrates the possible neutral mutations which may exist in the rpoB gene target *M. tuberculosis*, but does not cause drug resistance. FIG. 3 illustrates some of the mutations in the rpoB gene target which are known to cause drug resistance. Information about additional genes and their mutations that cause drug resistance in *M. tuberculosis* can be found at Sandgren A, Strong M, Muthukrishnan P, Weiner B K, Chruch, G M, Murray M B. (2009) Tuberculosis Drug Resistance Mutation Database. PLoS Med 6(2); herein incorporated by reference in its entirety.

Figure 4:
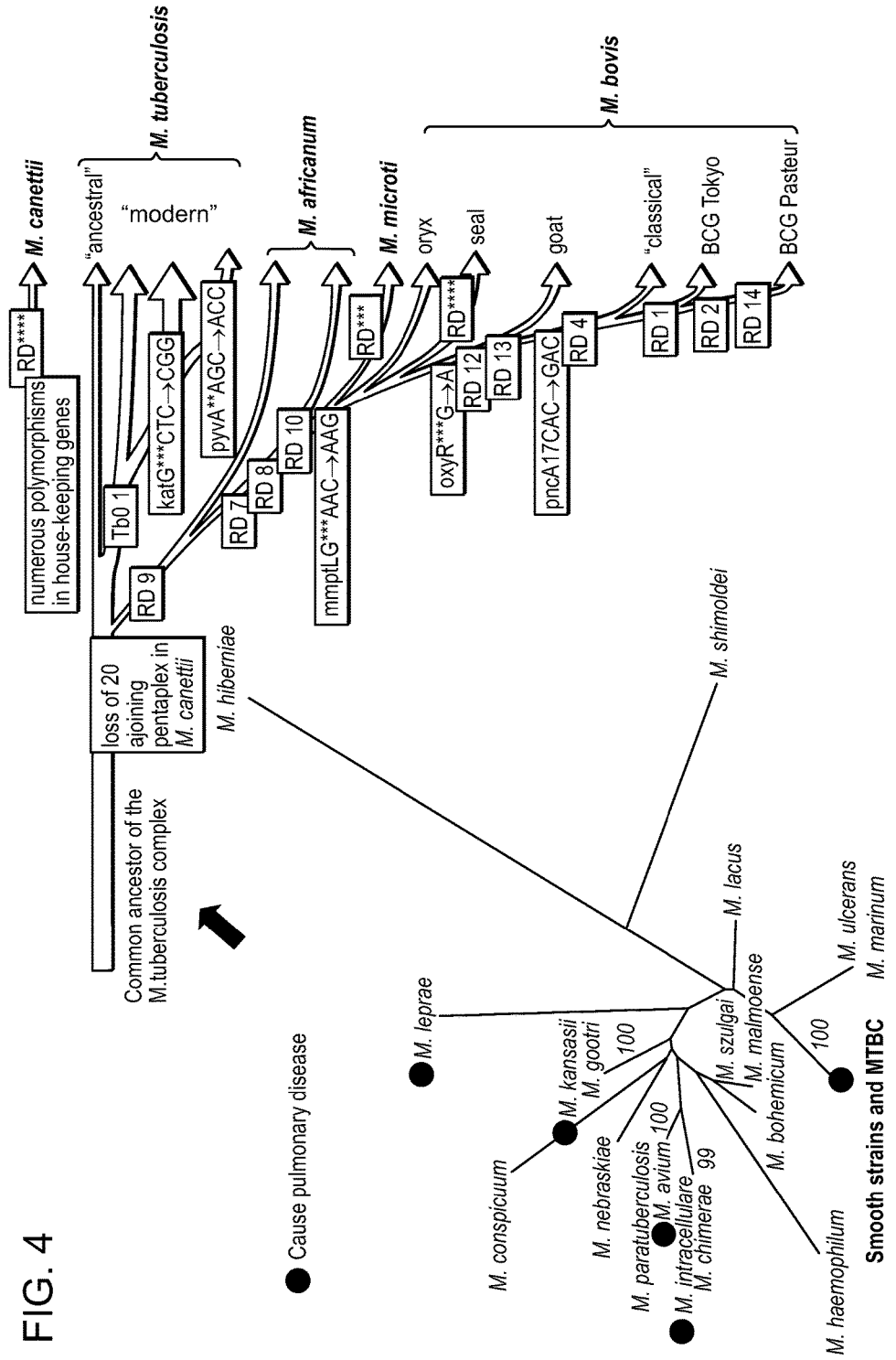
FIG. 4 illustrates the phylogenetic relationship of some NTM species and the MTBC species.

The phylogenetic relationship of some NTM species and the MTBC species is illustrated in FIG. 4. In some embodiments, the LATE-PCR limiting primers and excess primers employed in the assays described here were constructed to be complementary to DNA targets from the *M. tuberculosis* genome. Given the evolutionary divergence observed in among mycobacterial species said limiting and excess primers are imperfectly complementary to related target sequences in some other species of NTMs. Said primers are most likely to be fully complementary to the gene targets among other MTBC species whose members are most closely related to *M. tuberculosis*. The MTBC includes *M. africanum, M. bovis, M. canettii, M. microti*, and *M. tuberculosis*.

Table 1 summarizes the targets and probes employed in a nine-plex assay in terms of the purpose of each amplicon, the specific gene targets, the lengths of the target regions probed, and the number of probes utilized.

TABLE 1

| Antibiotics | Gene Target | Target Length | Number of Probes |
| --- | --- | --- | --- |
| Rifampin | rpoB | 101 | 3 On/3 Off |
| Ethambutol | embB | 29 | 1 On/1 Off + 1 unlabeled oligo. |
| Isoniazid | inhA | 36 | 1 On/1 Off |
| Isoniazid | ahpC | 93 | 2 On/2 Off |
| Isoniazid | katG | 40 | 1 On/1 Off |
| Fluoroquinolone | gyrA | 45 | 1 On/1 Off + 1 unlabeled oligo. |
| NTM vs MTBC | 16s rRNA | 63 | 2 On/2 Off |
| MTBC Species | gyrB | 31 | 2 On/1 Off + 1 unlabeled oligo. |
| Systems Control | ?? | ~30 | 1 On/1 Off |

The amplicons of gyrA, gyrB, and embB have significant hairpins which tend to prevent probe-target interactions. In these cases an unlabeled oligonucleotide of high Tm (e.g., silent probe) is added to inhibit hairpin formation and thus binding of the signaling and/or quencher probes. The 16s rRNA target used to distinguish MTBC from NTMs. In the embodiments described in Table 1, one probe set is employed to distinguish all MTBC from all NTMs, as well as to distinguish many of the NTMs from each other.

Figure 5:
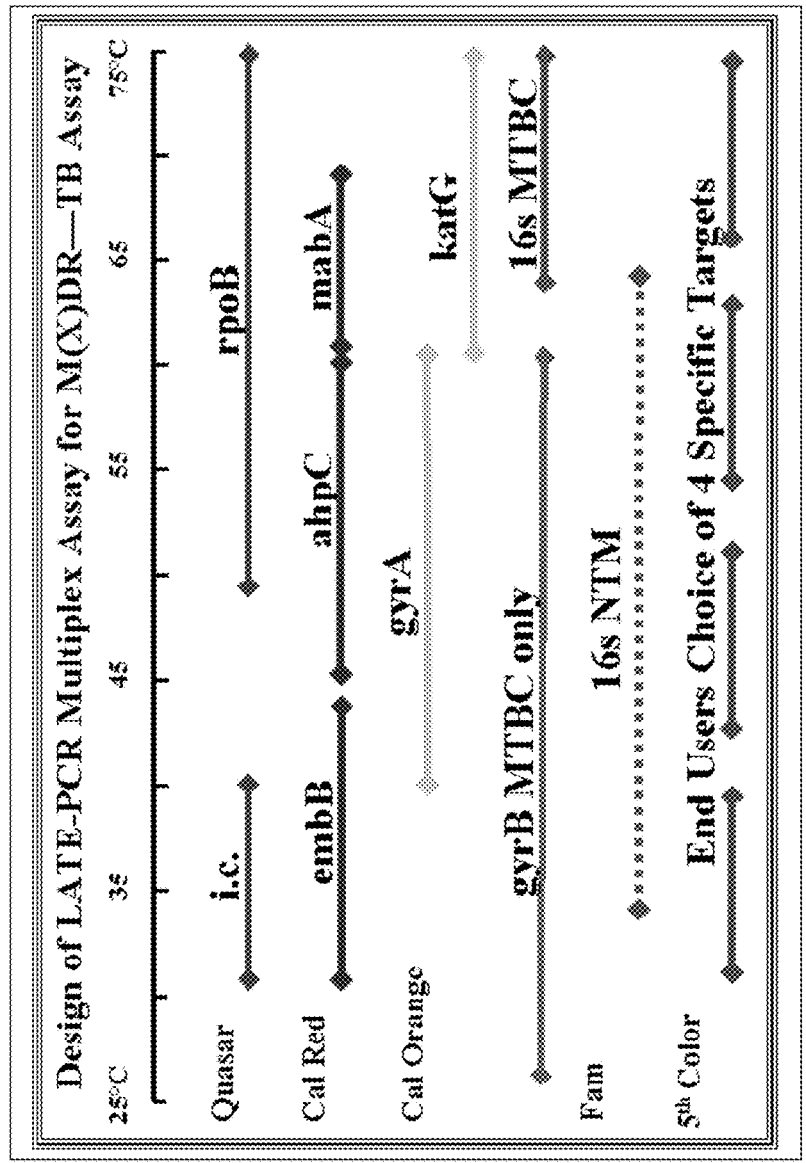
FIG. 5 illustrates endpoint target detection using four, or optionally five, dyes at a range of temperatures.

FIG. 5 illustrates how the targets of Table 1 are end-point detected using four colors (e.g., Quasar 670, Cal Red 610, Cal Orange 570, and FAM) over a range of temperatures between 25° C. and 75° C. As one versed in the art will appreciate, some fluorescent thermocyclers have capacities for more than four fluorescent colors. It is contemplated that one or more additional colors could be utilized for amplification and detection of one or more additional amplicons that are detected with one or more additional probes or sets of probes. Such additional amplicons could be built into assays at the request of an end-user who wishes to detect a particular target sequence which has a particular clinical significance. In some embodiments, amplicons detected or analyzed by other methods are multiplexed with the assays described herein. In some embodiments, such amplicons are analyzed by sequencing use a procedure such as "Dilute-N-Go" sequencing which is convenient for sequencing on or more strands of DNA generated in a multiplex LATE-PCR assay (Jia, Y., Osborne, A., Rice, J. E., and Wangh, L. J. (2010) Dilute-'N'-Go Dideoxy Sequencing of All DNA Strands Generated in Multiplex LATE-PCR Assays, Nucleic Acids Research; herein incorporated by reference in its entirety).

FIG. 5 demonstrates an embodiments in which a single target (rpoB) is analyzed with multiple probe sets that together generate a composite fluorescent signals over a wide temperature range, hereafter referred to as a temperature-dependent fluorescence signature.

FIG. 5 further illustrates an embodiments, in which more than one target is visualized using probe sets of the same color by designing the signals for one set of probes in a temperature range that is different from the temperature range for a separate target (e.g., gyrB and 16s). The signals from the two targets fuse into one composite temperature-dependent fluorescence signature which is informative as to the presence/absence or characteristics of more than one target.

Figure 6:
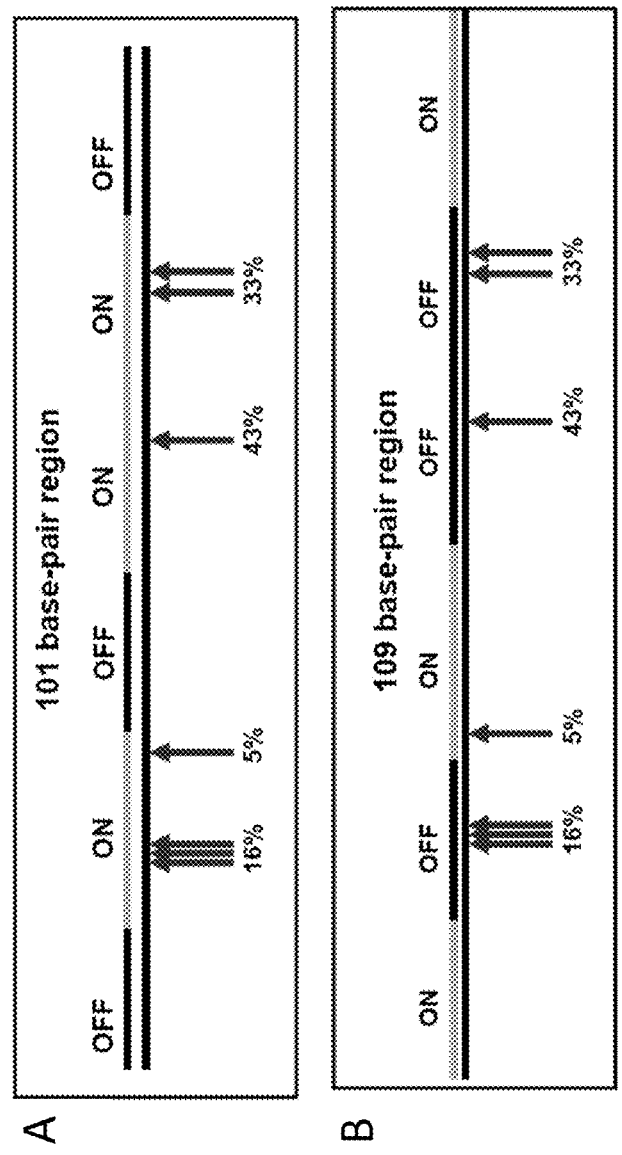
FIG. 6 has two panels. Panel A illustrates the location of the probe sets utilized for the rpoB gene target described in Table 1. Panel B illustrates the location of an alternate group of probe sets in which most mutations within the rpoB gene target fall beneath the quencher probes.
Figure 7:
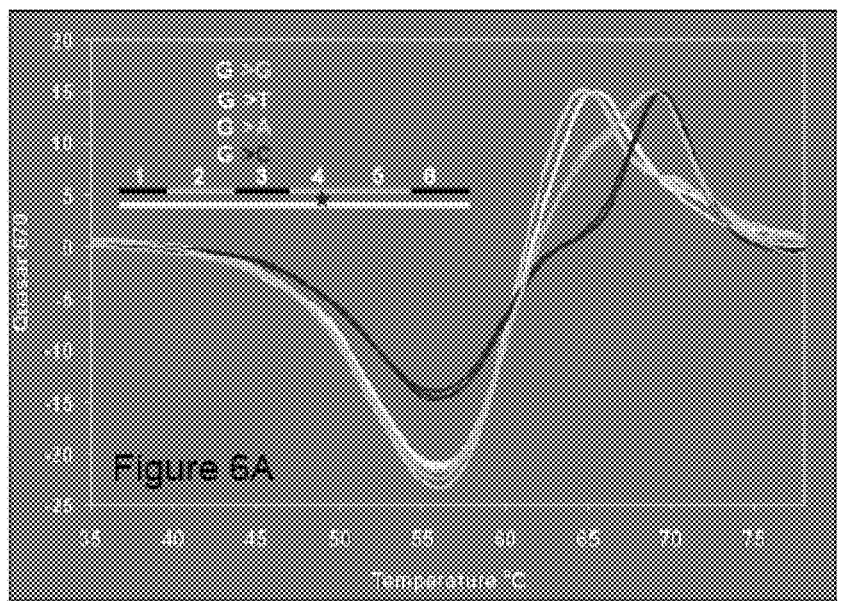
FIG. 7, Panels A and B illustrate the fluorescent signatures of the rpoB gene target for probe sets 5A and 5B, respectively.
Figure 7:
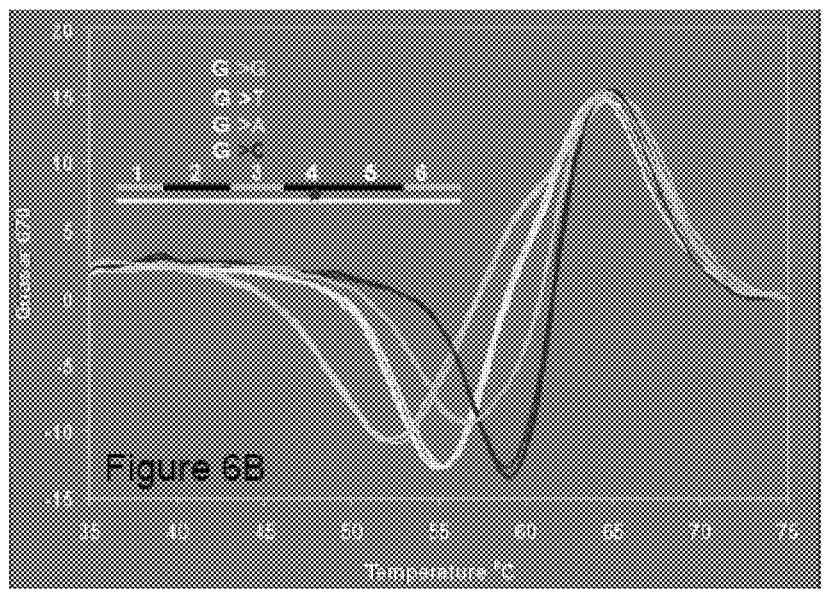

In some embodiments, probe sets for each target in a multiplex assay are employed to achieve maximum coverage of all possible sequence differences among related sequences, as well as maximum resolution among such sequence variants. FIG. 6A illustrates the location of the probe sets utilized for the rpoB gene target described in Table 1 and FIG. 5. Most mutations within the rpoB gene target fall within signaling probes and thereby decrease the corresponding Tm of the signaling probe to the target. As a consequence the fluorescent signal from signaling probe is observed at lower temperature. FIG. 6B illustrates the location of an alternate probe set in which most mutations within the rpoB gene target fall beneath quencher probes. As a consequence, the fluorescent signal from adjacent on probe is only quenched by its paired off-probe at lower temperature. FIGS. 7A and 7B illustrate the fluorescent signatures of the rpoB gene target for probe sets in FIGS. 6A and 6B, respectively. In this example, the probe set in FIG. 6B exhibited higher resolving power than probe set in 6A.

Figure 8:
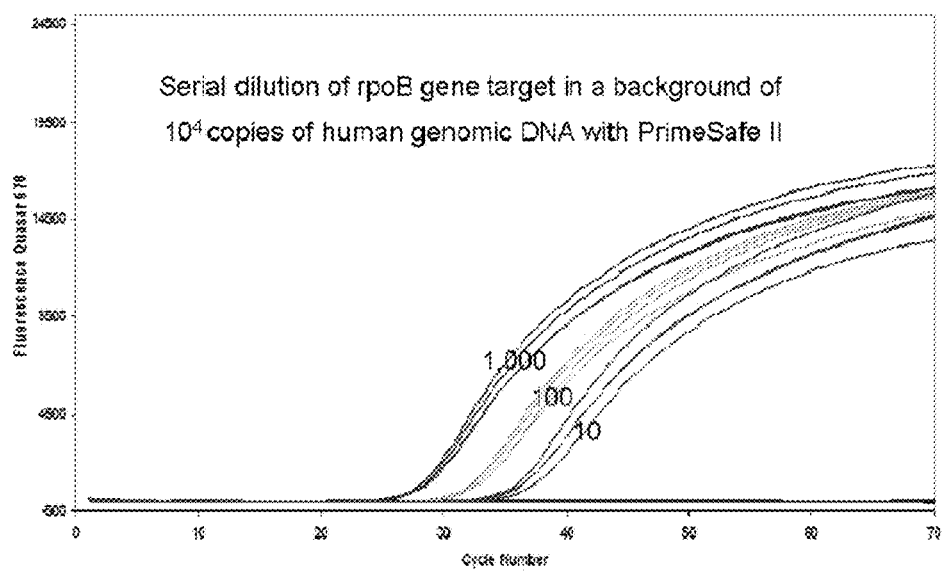
FIG. 8 illustrates that detection of amplification of 1000, 100, or 10 molecules of the rpoB target in the presence of 10,000 human genomes.

Sputum samples are the most commonly used source of samples for TB analysis because human sputum has a high concentration of human genomic DNA. The LATE-PCR assays, used to illustrate exemplary embodiments herein, are highly specific for their intended targets, despite the presence of high concentrations of human DNA for the following reasons: 1) LATE-PCR chemistry is inherently more specific that standard PCR chemistry; 2) Mycobacterial genomes have a very high GC content which means that high Tm primers can be employed for amplification together with high temperatures for annealing and extension; 3) PRIMESAFE II with four dabcyls and a high Tm can be employed to suppress mis-priming at all temperatures below the annealing-extension temperature. In some embodiments, primers are used which exhibit a bias for amplification of the desired sequences (e.g., a tuberculosis bias). FIG. 8 illustrates that 1000, 100, or 10 molecules of the rpoB target are all efficiently amplified in the presence of 10,000 human genomes. Table 2 illustrates the design of a multiplex reaction in which 10,000 human genomes and PRIMESAFE II were added to all reactions.

TABLE 2

| | M. intracellulare | M. tuberculosis |
|---|---|---|
| rpoB | Wild Type | Mutant |
| mabA | Wild Type | Wild Type |
| katG | Wild Type | Mutant |
| 16s | NTM | MTBC |
| gyrB | — | TB |
| 100.0 | 0.00 | 20,000 | 0 |
| 99.9 | 0.10 | 19,980 | 20 |
| 99.5 | 0.50 | 19,900 | 100 |
| 99.0 | 1.00 | 19,800 | 200 |
| 95.0 | 5.00 | 19,000 | 1000 |
| 90.0 | 10.00 | 18,000 | 2000 |
| 0.00 | 100.0 | 0 | 20,000 |
| H. Genome | 10,000 copies in all reactions | |
| PrimeSafe | Yes | |

TB infections and clinical samples are commonly comprised of more than one strain of a mycobacteria as well as other organisms, for instance a drug-resistant strain mixed with a drug-sensitive strain, or two different species of mycobacteria. In either case, the separate components of such a mixture may be present over a wide range of proportions, for instance from as little as 0.1% to 99.9%, up to 50% to 50%. In some embodiments, the assay described in Table 2 provides a penta-plex reaction capable of detecting low levels of M. tuberculosis in the presence of excess levels of an NTM, M. intracellulare. The results summarized in Table 3 demonstrate that as little as 0.1-0.5% M. tuberculosis can be detected in the presence of 99.9-99.5% of M. intracellular. In some embodiments, similar results are obtained in assays configured to detect other sub-groups of mycobacteria (e.g., rifampin-resistant M. tuberculosis among excess rifampin-sensitive M. tuberculosis). The sensitivity of this assay extends to any MTBC in the presence of an excess of any NTM because the primers utilized for each of the amplified targets are fully complementary to the MTBC genotypes but only partially complementary to the NTM genotypes.

TABLE 3

| | Relative Amplification Efficiency MTBC vs NTM | LOD for M. tb | Relative Amplification Efficiency Mutant vs W. Type | LOD for Mutant or Species* |
|---|---|---|---|---|
| rpoB | to be determined | to be determined | rpoB | 1 | 10% |
| mabA | 100,000X | 0.1-0.5% | inhA | 1 | 10% |
| katG | 10,000X | 0.1-0.5% | katG | 1 | 10% |
| gyrB | >40X | 0.1-0.5% | gyrB* | 1 | 10% |
| 16s | 1 | 10 mol | 16s* | 1 | 10% |

Table 3 also summarizes findings for the sensitivity of such an assay to detect a drug resistant strain of an MTBC in the presence of an excess of a wild type drug sensitive strain of said MTBC in this case the primers are equally complementary to both target genomes and the discrimination of drug resistance in the presence of drug sensitivity entirely depends on the probes used to visualize the fluorescent signatures of the drug resistant and drug sensitive strains. The estimate of 10% drug resistance in the presence of 90% drug sensitivity in Table 3 is based on empirical observation employing the probes shown in FIG. 6A for the rifampicin target. Based on the results illustrated in FIG. 7, it is likely that the lower limit of detection will be 1% drug resistance in 99% drug sensitive using the probe set shown in FIG. 6B.

EXPERIMENTAL

Features and embodiments of methods provided herein are illustrated in the Examples set forth below in conjunction with the accompanying Figures. The Examples should be viewed as exemplary and not limiting in scope.

Example 1

Detection of Drug Resistance in the rpoB Gene for Strains of M. tuberculosis

A LATE-PCR amplification was performed using a single pair of primers to amplify a 150 base pair region of the rpoB gene for each of several strains of Mycobacterium tuberculosis. The amplification provided a 101 base-pair region of the gene, which is known to contain mutations responsible for drug resistance for rifampicin, as a single-stranded nucleic acid target sequence (the Excess Primer strand of each LATE-PCR amplification). Following amplification, each single-stranded nucleic acid target sequence was probed using six separate probes that were included in the original amplification reaction mixture.

The probes in combination spanned the 101 base pairs of the single-stranded nucleic acid target sequence. Three of the probes were signaling probes. The signaling probes were quenched molecular beacon probes with two-nucleotide-long stems. Each included covalently bound labels: the fluorophore Quasar 670 on one end and a Black Hole Quencher 2, BHQ2, (Biosearch Technologies, Novato Calif.), on the other end. The other three probes were quencher probes terminally labeled with BHQ2 only, with no fluorophore. In this example the Tm's of the signaling probes with respect to the drug-sensitive strain differed from one another, and the Tm's of the quencher probes with respect to the drug-sensitive strain differed from one another. The three probe sets were detectably distinguishable.

At the end of amplification, probe-target hybridizations were analyzed as a function of temperature. In this example, hybridizations were characterized by the use of melt profile analysis. Reaction components and conditions were as follows:

```
                                          (SEQ ID No. 1)
Limiting Primer: 5' CTCCAGCCAGGCACGCTCACGTGACAGACCG (SEQ ID No. 2)
Excess Primer: 5'CCGGTGGTCGCCGCGATCAAGGAG Target: Strain 13545
                                          (SEQ ID No. 3)
5'CCGGTGGTCGCCGCGATCAAGGAGTTCTTCGGCACCAGCCAGCTGAGCC

AATTCATGGACCAGAACAACCCGCTGTCGGGGTTGACCCACAAGCGCCGA

CTGTCGGCGCTGGGGCCCGGCGGTCTGTCACGTGAGCGTGCCGGGCTGGA

G

Target: Strain 18460
                                          (SEQ ID No. 4)
5'CCGGTGGTCGCCGCGATCAAGGAGTTCTTCGGCACCAGCCAGCTGAGCC

AATTCATGGTCCAGAACAACCCGCTGTCGGGGTTGACCCACAAGCGCCGA

CTGTCGGCGCTGGGGCCCGGCGGTCTGTCACGTGAGCGTGCCGGGCTGGA

G

Target: Strain 9249
                                          (SEQ ID No. 5)
5'CCGGTGGTCGCCGCGATCAAGGAGTTCTTCGGCACCAGCCAGCTGAGCC

AATTCATGGACCAGAACAACCCGCTGTCGGGGTTGACCCACAAGCGCCGA

CTGTTGGCGCTGGGGCCCGGCGGTCTGTCACGTGAGCGTGCCGGGCTGGAG

The underline in the sequence of each of strains
18460 and 9249 denotes the location of the nucle-
otide change from the drug-sensitive strain 13545.

Probe 1:
                                          (SEQ ID No. 6)
5'-BHQ2-CTGGTTGGTGCAGAAG-C3

Probe 2:
                                          (SEQ ID No. 7)
5'-BHQ2-TCAGGTCCATGAATTGGCTCAGA-Quasar 670

Probe 3:
                                          (SEQ ID No. 8)
5'-BHQ2-CAGCGGGTTGTT-C3

Probe 4:
                                          (SEQ ID No. 9)
5'-BHQ2-ATGCGCTTGTGGATCAACCCCGAT-Quasar 670

Probe 5:
                                          (SEQ ID No. 10)
5'-Quasar 670-AAGCCCCAGCGCCGACAGTCGTT BHQ2

Probe 6:
                                          (SEQ ID No. 11)
5'-ACAGACCGCCGG BHQ2

A three carbon linker is denoted with C3 while a
Black Hole Quencher 2 is denoted with BHQ2
(Biosearch Technologies, Novato CA).
```

LATE PCR amplifications were carried out in a 25 µl volume consisting of 1×PCR buffer (Invitrogen, Carlsbad, Calif.), 2 mM MgC12, 200 nM dNTPs, 50 nM Limiting Primer, 1000 nM Excess Primer, 1.25 units of Platinum Taq DNA Polymerase (Invitrogen, Carlsbad, Calif.), 500 nM of probes 1, 3 and 6, and 200 nM of probes 2, 4 and 5. For each strain tested approximately 1000 genomes equivalents were used. Amplification reactions for each strain were run in triplicate.

The thermal profile for the amplification reaction was as follows: 98° C./3 min for 1 cycle, followed by 98° C./10 s-75° C./40 s for 50 cycles, followed by fluorescent acquisition at each degree starting with an anneal at 75° C. with 1° C. decrements at 30 s intervals to 34° C. followed by 10 min at 34° C. This was followed by a melt starting at 34° C. with 1° C. increments at 30 s intervals to 81° C.

The melting temperatures of the probes was performed utilizing the computer program Visual OMP 7.0 with the concentrations of target, signaling probes, and quencher probes at 100 nM, 200 nM and 500 nM respectively. The Tm's were as follows: Probe 1, 50° C.; Probe 2, 63° C.; Probe 3, 56° C.; Probe 4, 67° C.; Probe 5, 75° C.; and Probe 6, 63° C. Analysis of the probe target hybridizations following amplification was by melt curve analysis using the first derivative for Quasar 670 fluorescence for temperatures between 35° C. to 78° C. From this data set the highest fluorescent value was used to normalize the data to one. If the value used was negative, it was multiplied by (−15); if it was a positive number, it was multiplied by fifteen.

Figure 9:
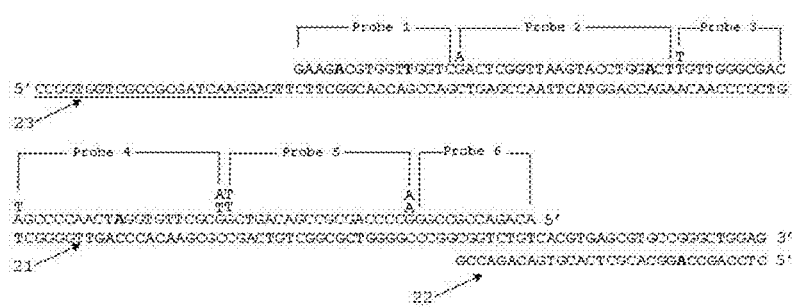
FIG. 9 is a schematic representation of a single-stranded nucleic acid sequence (SEQ ID NO: 38) from Example 1 showing probe binding locations and primer binding locations.

FIG. 9 illustrates binding of the three prose sets (Probes 1/Probe 2, Probe 3/Probe 4, and Probe 5/Probe 6) to the single-stranded nucleic acid target sequence utilizing drug-susceptible strain 13545 as the target. In FIG. 9, strand 21 is the target strand, strand 23 is the Excess Primer, and strand 22 is the Limiting Primer. For the purpose of illustration probes 1-6 are shown hybridized to strand 21 in a 3' to 5' orientation with their mismatched ends above. Mismatches between the probes and strand 21 and between the Limiting Primer and strand 21 are bolded. Fluorophore and quencher labels are omitted from FIG. 9 but are given above in the sequence descriptions. Some of the nucleotides in the probe sequences were deliberately mismatched to the sensitive strain 13545 such as Probe 1, which contains mismatches in positions 31 (A to G) and 38 (T to G) relative to the 5' end of strand 21. Other mismatches are in Probe 2, position 62 (A to A), Probe 4, position 86 (A to C). Within the Limiting Primer at position 142(A to G) is a mismatch which was included to reduce a hairpin that occurred in the original target strand. In addition to these mismatches in the sensitive strain 13545, strains 18460 has a nucleotide mismatch at position 59 (T to T) while strain 9249 has a mismatch at position 104 (G to T).

It will be appreciated that LATE-PCR amplification provides a sample containing the Excess Primer strand, which comprises the single-stranded nucleic acid target sequence that is actually probed. The Excess Primer strand includes the Excess Primer sequence at one end and the complement of the Limiting Primer sequence at the other end. In this case, due to the mismatch between the Limiting Primer and strand 21, the Excess Primer strand will differ from strand 21 at position 142, which will be a T rather than a G. As to the region of strand 21 complementary to probes 1-6, the Excess Primer strand is identical to strand 21.

Figure 10:
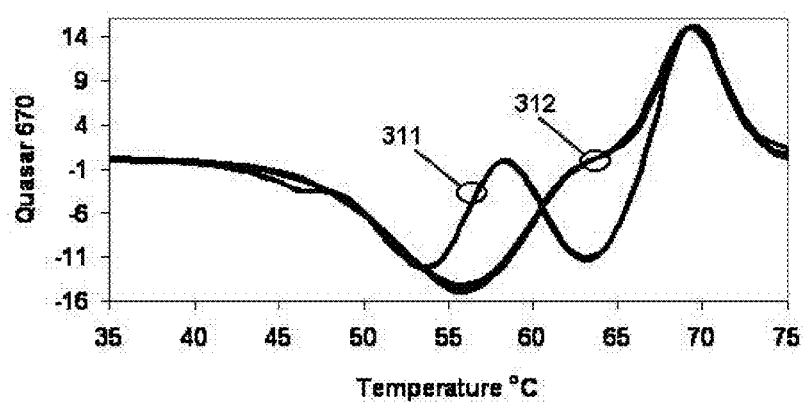
FIG. 10, Panels A and B present melt-curve analyses from amplifications described in Example 1 for several strains.
Figure 10:
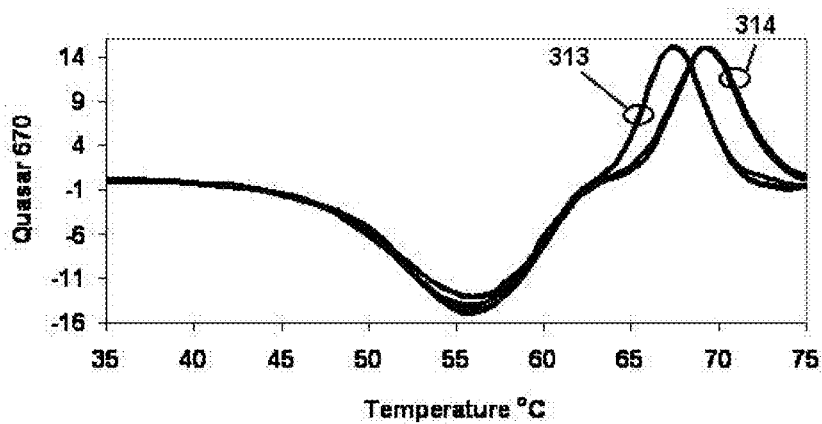

FIG. 10A presents the results of the analysis for two different strains of M. tuberculosis, strain 13545 and strain 18460. Data from analysis of the triplicate samples of the separate amplifications of the two strains are superimposed for the purpose of illustration. Circle 311 represents the drug-resistant strain 18460 (D516V, an aspartic acid located at amino acid position 516 changed to a valine), while, circle 312 shows the replicates from the drug-sensitive strain 13545 (V146F, a valine located at amino acid position 146 changed to a phenylalanine). FIG. 10B presents the results for drug-resistant strain 9249 and drug-sensitive strain 13545, where circle 313 shows the replicates for drug-resistant strain 9249 (S531L, a serine located at amino acid position 513 changed to a leucine) and circle 314 shows the replicates from the drug-sensitive strain 13545 (V146F).

Example 2

The Detection of a Drug Resistance Strain of *M. Tuberculosis* in a Mixed Sample LATE PCR amplifications were performed to provide single-stranded nucleic acid target sequences using resistant *M. tuberculosis* strain 18640 (D516V, an aspartic acid located at amino acid 516 changed to a valine) and the sensitive strain 13545 in different ratios to determine the level of sensitivity within a mixed sample. Reaction components and conditions are described in Example 1, except for the starting target sequences included in the reaction mixtures. Amplicons generated from strain 18640 and strain 13545 using the primers from Example 1 comprise a single nucleotide variation within the hybridization sequence of probe 2. In this embodiment, probe 2 is a signaling probe. Alternatively, in some embodiments, a quencher probe that hybridizes to the region of the amplicon containing the variable nucleotide may be employed, and a corresponding signaling probe is design to hybridize adjacently. One reaction mixture contained only strain 18460, and another reaction mixture contained only strain 13545. Each of these 100% controls contained approximately 100,000 genomic DNA copies of the pertinent strain. Reaction mixtures for a first mixed sample contained 20% (approximately 20,000 genomes) of resistant strain 18460 with 80% (approximately 80,000 genomes) of sensitive strain 13545. The reaction mixture for a second mixed sample contained 10% of strain 18460 (10,000 genomes) with 90% of strain 13545 (90,000 genomes). The reaction mixture for a third mixed sample contained 5% of strain 18460 (5,000 genomes) with 95% of strain 13545 (95,000 genomes). The reaction mixture for a fourth mixed sample contained 1% of strain 18460 (1,000 genomes) with 99% of strain 13545 (99,000 genomes). Amplification reactions were run in triplicate.

The thermal profile for the amplification reaction was as follows: 98° C./3 min for 1 cycle, followed by 98° C./10 s-75° C./40 s for 50 cycles, followed by fluorescent acquisition at each degree starting with an anneal at 75° C. with 1° C. decrements at 30 s intervals to 34° C. then a hold for 10 min at 34° C. This is followed by a melt starting at 34° C. with 1° C. increments at 30 s intervals to 81° C. followed by an anneal starting at 75° C. with 1° C. decrements at 30 s intervals to 34° C. This melt/anneal profile was repeated three more times.

The data used for graphical analysis of the hybridization of the six probes was the average of each replicate from the last three melt profiles. From these average values the fluorescence at 35° C. was subtracted, and the resulting values were normalized by division of all values with the fluorescence at 78° C. The first derivative of the resulting data were then generated and normalized by dividing all values using the largest positive value.

In order to remove the contribution of the sensitive strain DNA from mixtures containing both sensitive and resistant strain DNA's, replicates of the pure sensitive strain DNA samples (100% controls) were used to generate average-derived-values at every temperature, as described above. These values were then subtracted from the derived-average-values of each mixture to arrive at the contribution of the resistant strain. In addition, the scatter among separate samples of pure sensitive DNA was established by subtracting the derived-average-values of pure sensitive DNA from each of the individual samples of pure sensitive DNA.

Figure 11:
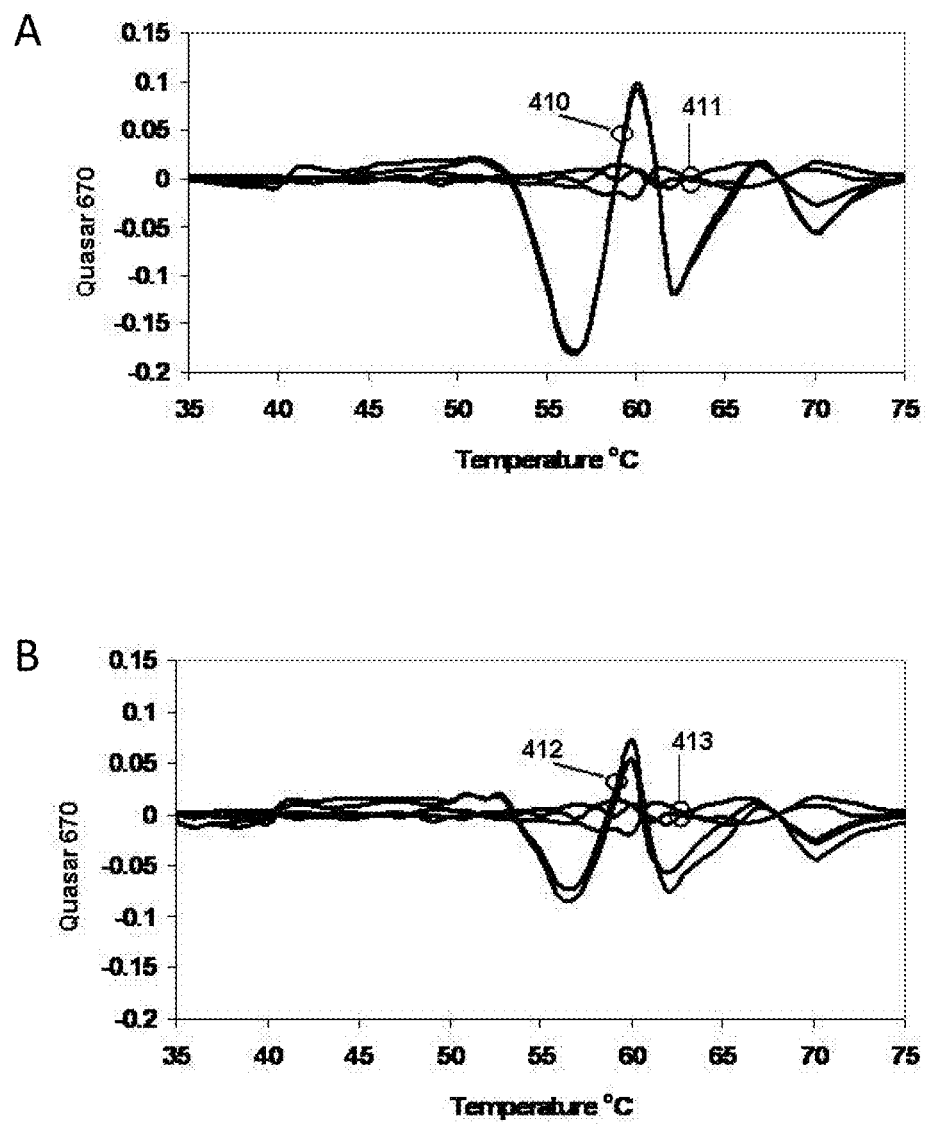
FIG. 11, Panels A-D present derivative melting curves for mixtures of TB strains in various proportions as described in Example 2.
Figure 11:
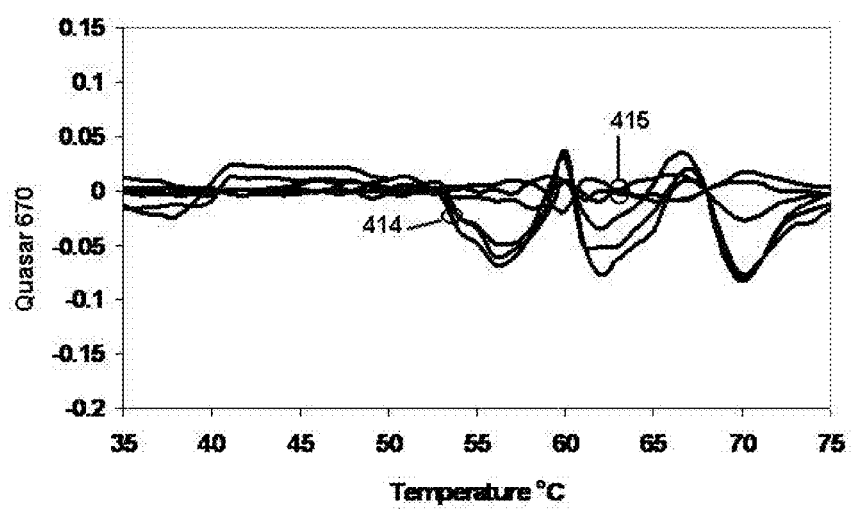
Figure 11:
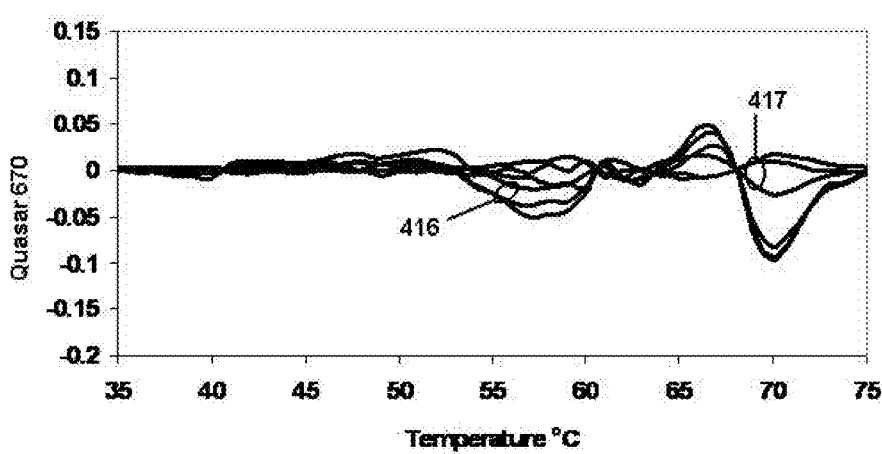

FIGS. 11A-11D show the resulting analysis. They display the signal from various percentages of the resistant strain 18460 in an increasing background of sensitive strain 13545. FIG. 11A shows this signal with a mixed sample of 20% resistant strain 18460 in a background of 80% sensitive strain 13545, where circle 410 identifies the contribution of the resistant strain in replicates of the mixture, and circle 411 identifies the scatter among replicates for the pure sensitive strain. FIG. 11B shows this signal with the 10% mixture, with circle 412 representing the contribution of the resistant strain in replicates of the mixture, and circle 413 representing scatter among replicates for the pure sensitive strain. FIG. 11C shows the signal from the mixture of 5% resistant strain replicates (circle 414 identifying the contribution of the resistant strain in replicates of the mixture, and circle 415 identifying scatter among replicates for the pure sensitive strain). FIG. 11D shows the signal from the mixture of 1% resistant strain. Circle 416 identifies the contribution of the resistant strain in replicates of the mixture, and circle 417 identifies the scatter among replicates of the pure sensitive strain.

Example 3

Multi-drug Resistance Detection in Strains of *M. tuberculosis*

A multiplex LATE-PCR assay was used to provide multiple single-stranded target nucleic acids to detect drug resistance in the three genes, gyrA (fluoroquinolones), katG (isoniazid), and rpoB (rifampicin), of each of three strains, 13545, 202626 and 15552. For the gyrA gene the strains 13545 and 202626 were drug-sensitive while strain 15552 (A90V, an aspartic acid located at amino acid position 90 changed to a valine) was drug-resistant. For the katG gene the strain 202626 was drug-sensitive, while strain 13545 (S315T, a serine located at amino acid position 315 changed to a tyrosine) and strain 15552 (S315N, a serine located at amino acid position 315 changed to an asparagine) were resistant. For the rpoB gene strain 13545 was a sensitive strain while strain 15552 (S531L, a serine located at amino acid position 513 changed to a leucine) and strain 202626 (H526D, a histidine located at amino acid position 513 changed to an aspartic acid) were resistant.

Reaction components and conditions were as follows:

```
For the gyrA gene
                                              (SEQ ID No. 12)
Limiting Primer: 5' ACCAGGGCTGGGCCATGCGCACCA (SEQ ID No. 13)
Excess Primer: 5' GGACCGCAGCCACGCCAAGTC Target: Strain 13545
                                              (SEQ ID No. 14)
5'GGACCGCAGCCACGCCAAGTCGGCCCGGTCGGTTGCCGAGACCATGGG

CAACTACCACCCGCACGGCGACGCGTCGATCTACGACAGCCTGGTGCGCA

TGGCCCAGCCCTGGT

Target: Strain 202626
Identical to strain 13545

Target: Strain 15552
                                              (SEQ ID No. 15)
5'GGACCGCAGCCACGCCAAGTCGGCCCGGTCGGTTGCCGAGACCATGGG

CAACTACCACCCGCACGGCGACGTGTCGATCTACGACAGCCTGGTGCGCA

TGGCCCAGCCCTGGT
```

-continued

Probe 1:
(SEQ ID No. 16)
5' CGACCGGGCC-BHQ2

Probe 2:
(SEQ ID No. 17)
5' Cal Red 610-AACCCATGGTCTCGGCAACTT-BHQ2

Probe 3:
(SEQ ID No. 18)
5' Cal Red 610-AATCGCCGTGCGGGTGGTAGTT-BHQ2

Probe 4:
(SEQ ID No. 19)
5'GCTGTCGTAGATCGACGCG-BHQ2

For the katG gene
Limiting Primer:
(SEQ ID No. 20)
5' AGCGCCCACTCGTAGCCGTACAGGATCTCGAGGAAAC Excess Primer:
(SEQ ID No. 21)
5' TCTTGGGCTGGAAGAGCTCGTATGGCAC Target: Strain 202626
(SEQ ID No. 22)
GCTTGGGCTGGAAGAGCTCGTATGGCACCGGAACCGGTAAGGACGCGATC

ACCAGCGGCATCGAGGTCGTATGGACGAACACCCCGACGAAATGGGACA

ACAGTTTCCTCGAGATCCTGTACGGCTACGAGTGGGAGCT

Target: Strain 13545
(SEQ ID No. 23)
GCTTGGGCTGGAAGAGCTCGTATGGCACCGGAACCGGTAAGGACGCGATC

ACCACCGGCATCGAGGTCGTATGGACGAACACCCCGACGAAATGGGACA

ACAGTTTCCTCGAGATCCTGTACGGCTACGAGTGGGAGCT

Target: Strain 15552
(SEQ ID No. 24)
GCTTGGGCTGGAAGAGCTCGTATGGCACCGGAACCGGTAAGGACGCGATC

ACCAACGGCATCGAGGTCGTATGGACGAACACCCCGACGAAATGGGACA

ACAGTTTCCTCGAGATCCTGTACGGCTACGAGTGGGAGCT

Probe 1:
(SEQ ID No. 25)
5' Cal Orange 560-AAGTGATCGCGTCCTTACCTT-BHQ2

Probe 2:
(SEQ ID No. 26)
5' GACCTCGATGCAGCTG-BHQ2

For the rpoB gene
Limiting Primer: same as in Example 1

Excess Primer: same as in Example 1

Target: Strain 202626
(SEQ ID No. 27)
5'CCGGTGGTCGCCGCGATCAAGGAGTTCTTCGGCACCAGCCAGCTGAGCC

AATTCATGGACCAGAACAACCCGCTGTCGGGGTTGACCGACAAGCGCCGA

CTGTCGGCGCTGGGGCCCGGCGGTCTGTCACGTGAGCGTGCCGGGCTGGA

G

Target: Strain 15552
Same as strain 9249 set forth in Example 1

Target: Strain 13545
Set forth in Example 1

-continued

Probes used for rpoB gene:
Probes 1-6 set forth in Example 1

The underline in a target sequence denotes the location of the nucleotide change from the drug sensitive strain.

LATE-PCR amplifications were performed in triplicate carried out in a 25 ul volume consisting of 1×PCR buffer (Invitrogen, Carlsbad, Calif.), 2 mM MgC12, 200 nM dNTPs, 50 nM Limiting Primer and 1000 nM Excess Primer for each primer set, 1.25 units of Platinum Taq DNA Polymerase (Invitrogen, Carlsbad, Calif.), for the gyrA probes 500 nM of probes 1 and 3 with 200 nM of probes 2 and 4, for the katG probes 200 nM of probe 1 and 500 nM of probe 2, and for the rpoB probes the concentrations set forth in Example 1. For all strains tested approximately 1000 genomes equivalents of pre-amplification target were used, and amplification reactions for each strain were run in triplicate.

The thermal profile for the amplification reaction was as follows: 98° C./3 min for 1 cycle, followed by 98° C./10 s-75° C./40 s for 50 cycles, followed by an anneal starting at 75° C. with 1° C. decrements at 30 s intervals to 34° C., followed by 10 min at 34° C. This was followed by a melt starting at 34° C. with 1° C. increments at 30 s intervals to 81° C.

Probe-target hybridizations were analyzed by the melt curve analysis using the first derivative for each fluor separately for the temperatures between 35° C. to 78° C. From each data set the highest fluorescent value was used to normalize the data to one. If the value used is negative then it is multiplied by −15 (minus fifteen), if it was a positive number then it is multiplied by +15 (plus fifteen). Each of the strains tested differs in respect to drug resistance. See Table 1 below. For example, strain 13545 is resistant to isoniazid drugs while sensitive to both fluorquinolones and rifampicin while strain 15552 is resistant to all three drugs.

TABLE 1

| Drug | Gene | Strain 13545 | Strain 202626 | Strain 15552 |
|---|---|---|---|---|
| Fluorquinolones | gyrA | Sensitive | Sensitive | Resistant |
| Isoniazid | katG | Resistant | Sensitive | Resistant |
| Rifampicin | rpoB | Sensitive | Resistant | Resistant |

Figure 12:
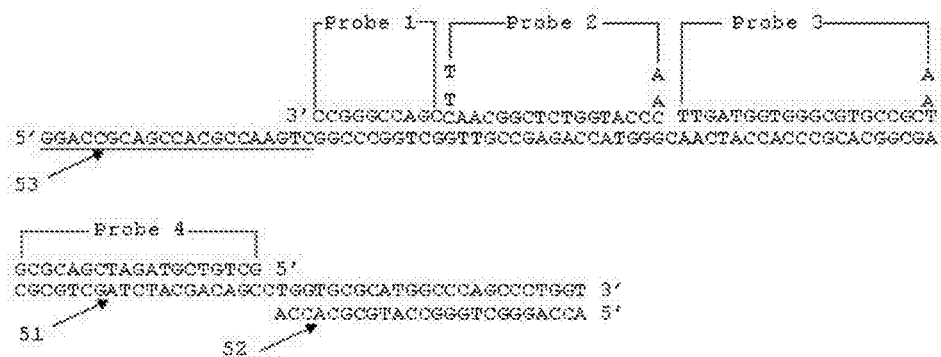
FIG. 12 is a schematic representation of a single-stranded nucleic acid sequence (SEQ ID NO: 14) from Example 3 showing probe binding locations and primer binding locations.

FIG. 12 illustrates probe binding of primers and probes to strand 51, the gyrA target of strain 13545, which, because the primers were perfectly complementary to the original target strand, is identical to the Excess Primer strand. In FIG. 12 the underlined portion 53 of sequence 51 are the nucleotides of the Excess Primer and sequence 52 is the Limiting Primer. Probes 1-4 are shown hybridized to strand 51 in a 3' to 5' orientation with their unmatched ends above. The probes are labeled with their respective quenchers or fluorophores (not shown) as described above. Strain 15552 differs relative to the 5' end at position 72, a T nucleotide from that of both strains 13545 and 202626 which has a C nucleotide in that position.

Figure 13:
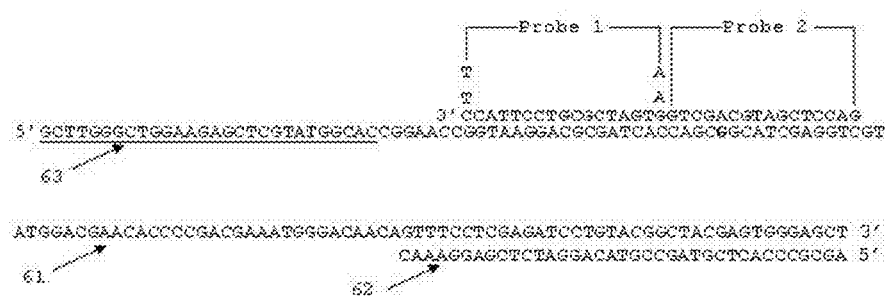
FIG. 13 is a schematic representation of another single-stranded nucleic acid sequence (SEQ ID NO: 22) from Example 3 showing probe binding locations and primer binding locations.

FIG. 13 illustrates probe binding of primers and probes to strand 61, the katG target of strain 202626, which, because the primers were perfectly complementary to the original target strand, is identical to the Excess Primer strand; that is, one of the three single-stranded products of the LATE-PCR amplification reaction. In FIG. 13, underlined sequence 63 is the nucleotides of the Excess Primer, and underlined sequence 62 is the Limiting Primer. Probes 1, 2 are shown hybridized to strand 61 in the 3' to 5' orientation with their mismatched ends above. Relative to the 5' end of strand 61, all three strains differ at position 56 (G, in bold) to Probe 2. At position 54 is a "G" as shown for strain 202626, but it is a "C" in strain 13545 and an "A" in strain 15552. The Excess Primer contains a deliberate mismatch at the 5' end (a "T" rather than the "G" in each of the targets) to reduce potential mispriming during the linear phase of LATE-PCR amplification.

The thermal profile for the amplification reaction was as follows: 98° C./3 min for 1 cycle, followed by 98° C./10 s-75° C./40 s for 50 cycles, followed by an anneal starting at 75° C. with 1° C. decrements at 30 s intervals to 34° C. followed by 10 min at 34° C. This is followed by a melt starting at 34° C. with 1° C. increments at 30 s intervals to 81° C.

Figure 14:
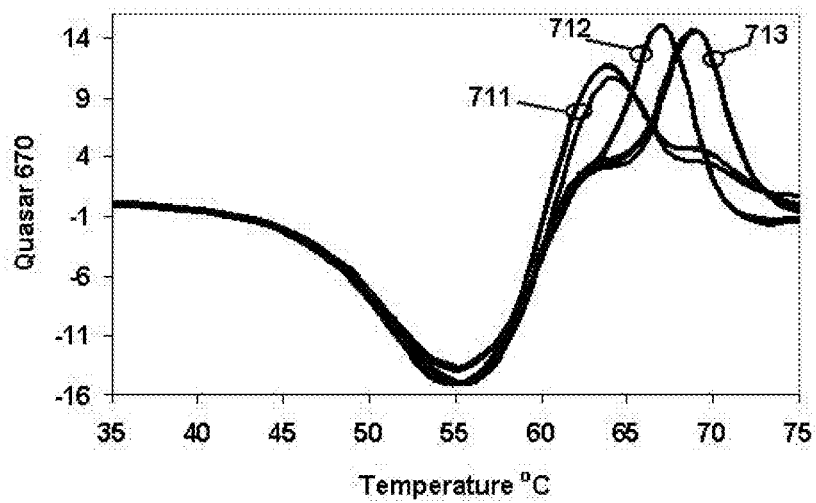
FIG. 14, Panels A-C are graphs of fluorescence versus temperature for each of the fluorophores in the sample of Example 3.
Figure 14:
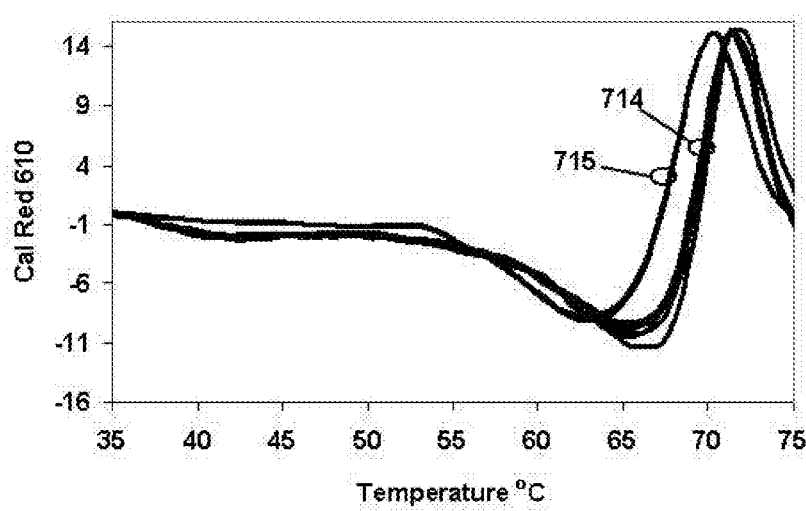
Figure 14:
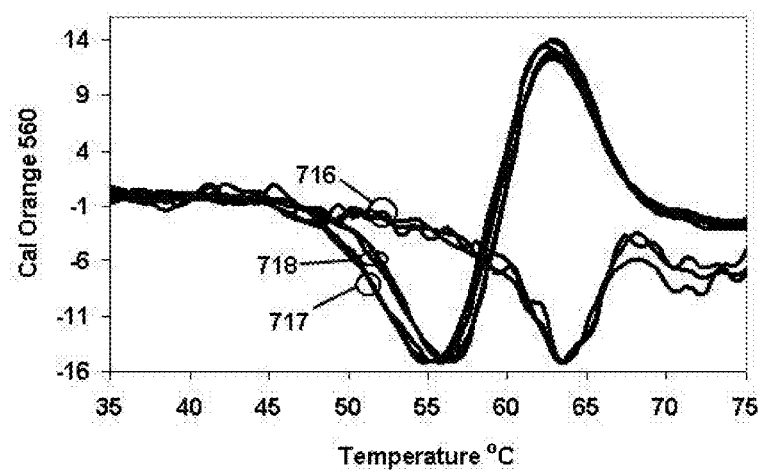
Figure 15:
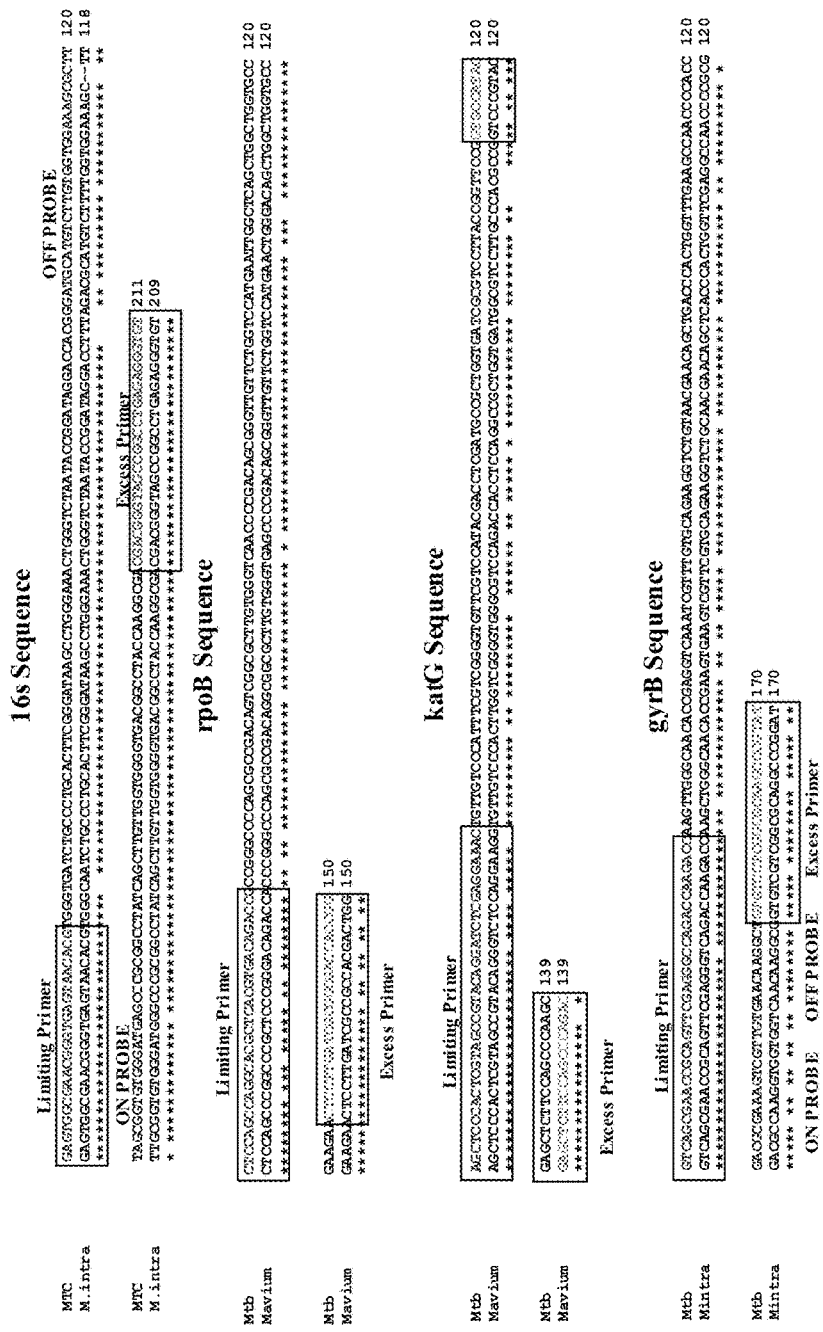
FIG. 15 shows exemplary sequence alignments used in primer, probe, and target sequence design.
Figure 16:
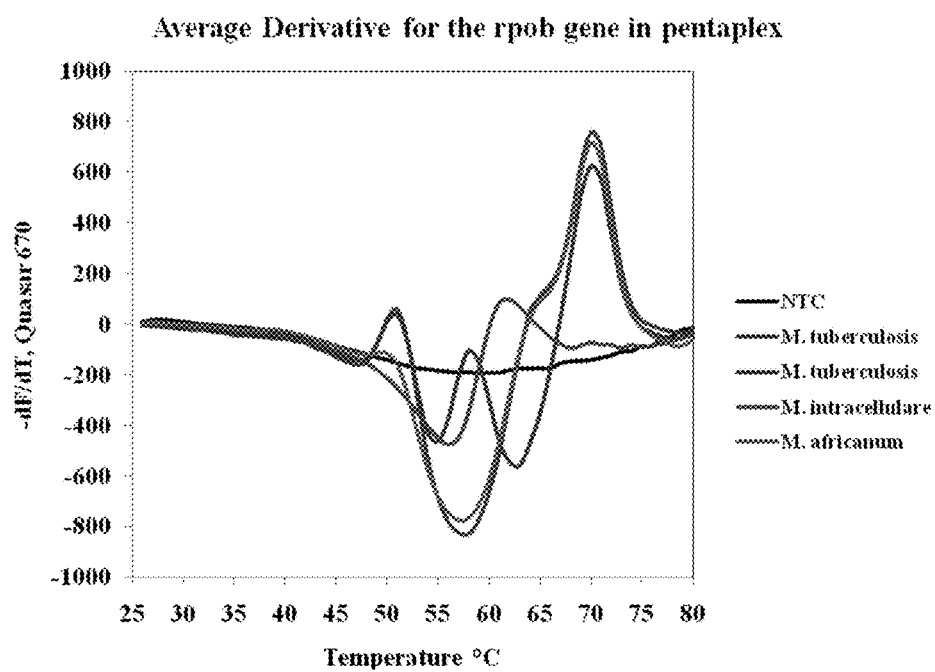
FIG. 16, Panels A-D show graphs demonstrating species differentiation and detection of drug resistance among members of the genus *Mycobacterium*.
Figure 16:
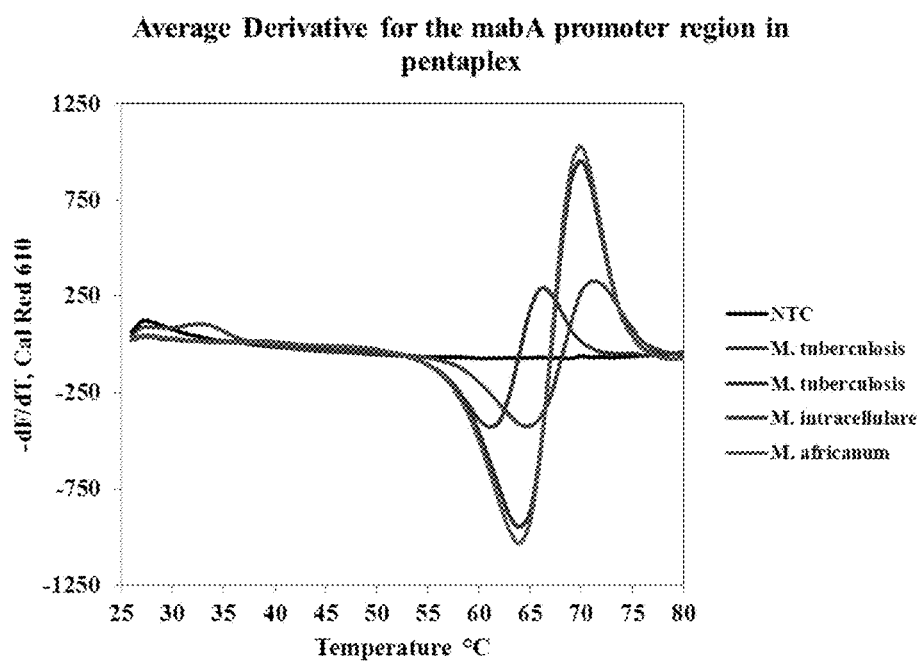
Figure 16:
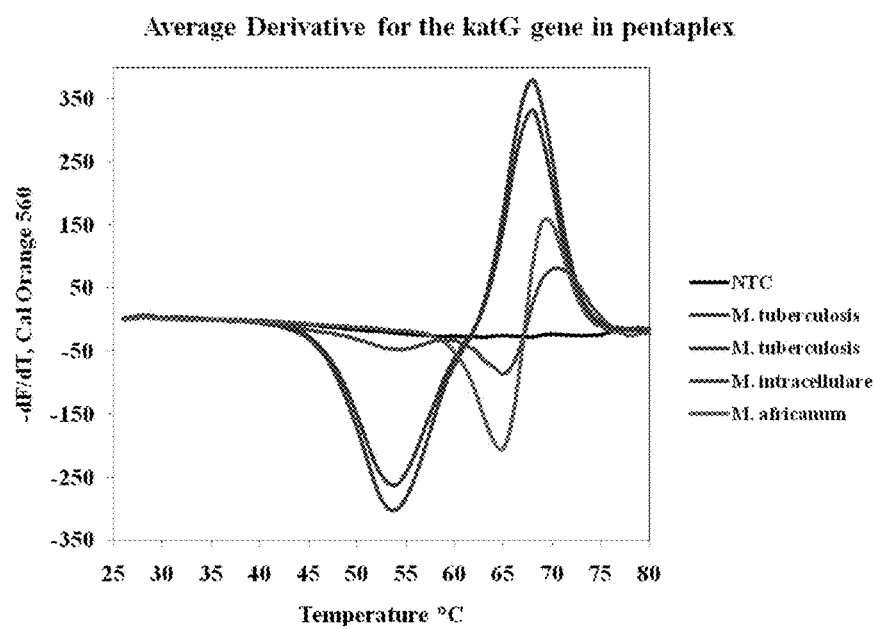
Figure 16:
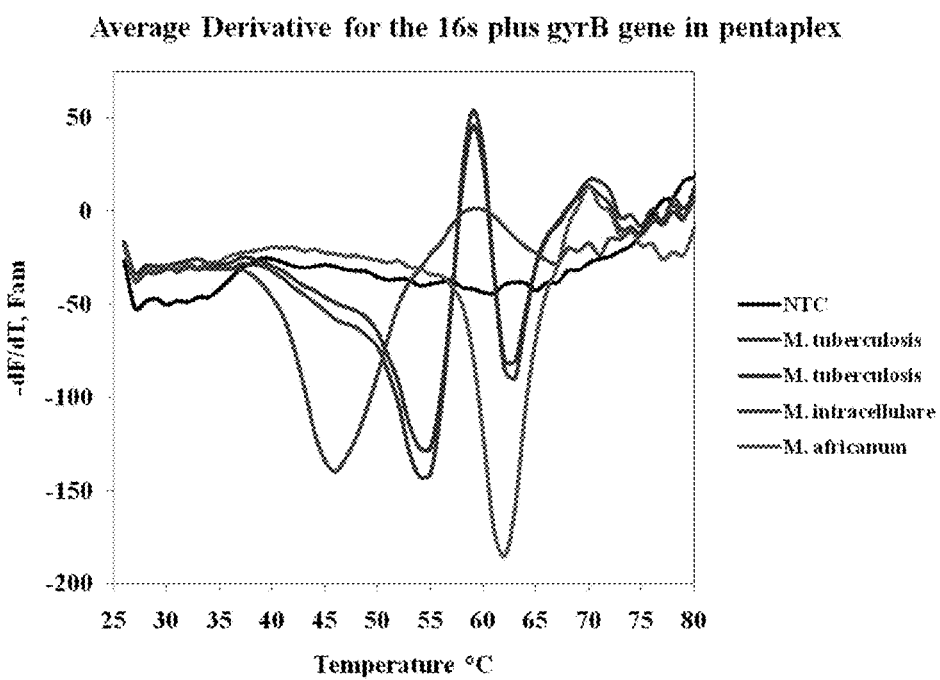

FIG. 14A presents the normalized fluorescence readings of all six probes for the rpoB gene in three different strains of M. tuberculosis as a function of the temperature. Circle 711 represents the replicates for strain 202626, while circle 712 shows the replicates for strain 15552 and circle 713 are the replicates for strain 13545. FIG. 14B shows the results for the gyrA probes, which distinguish the sensitive strains 202626 and 13545 (circle 714) from the drug resistant strain 15552 (circle 715). The results for the katG gene probes are shown in FIG. 14C, in which all three melt derivatives are different, circle 716 are replicates of the sensitive strain 202626, while the resistant strains 13545 and 15552 are represented by circle 717 and circle 718, respectively.

Example 4

Species Differentiation and Detection of Drug Resistance Among Members of the Genus *Mycobacterium*

A multiplex LATE-PCR assay was used to provide multiple single-stranded target nucleic acids to detect drug resistance for isoniazid using katG plus the promoter region of the mabA gene and resistance for rifampin determined with the rpoB gene. Also the assay uniquely identifies *M. tuberculosis* from other members of the genus *Mycobacterium* by using a combination of two genes, the 16s ribosomal and the gyrase B genes.

Primers, probes, and target sequences were the result of extensive analysis of sequence alignments (SEE FIG. 15) and empirical testing to yield sequences that, when used in assays provide information-rich results. Reaction components and conditions were as follows:

The primer sequences for the rpoB gene;

rpoB Limiting Primer:
(SEQ ID No. 28)
5' CTCCAGCCAGGCACGCTCACGTGACAGACCG rpoB Excess Primer:
(SEQ ID No. 29)
5'CCGGTGGTCGCCGCGATCAAGGAG The probe sequences for the rpoB gene:
rpoB Off Probe 1
(SEQ ID No. 30)
5'-BHQ2-CTGGTTGGTGCAGAAG-$C_3$ -continued rpoB On Probe 1
(SEQ ID No. 31)
5'-Quasar 670-TCAGGTCCATGAATTGGCTCAGA BHQ2 rpoB Off Probe 2
(SEQ ID No. 32)
5'-BHQ2-CAGCGGGTTGTT-$C_3$ rpoB On Probe 2
(SEQ ID No. 33)
5'-Quasar 670-ATGCGCTTGTGGATCAACCCCGAT BHQ2 rpoB On Probe 3
(SEQ ID No. 34)
5'-Quasar 670-AAGCCCCAGCGCCGACAGTCGTT BHQ2 rpoB Off Probe 3
(SEQ ID No. 35)
5'-ACAGACCGCCGG BHQ2 rpoB target sequences:
*M. tuberculosis* strain 8094;
(SEQ ID No. 36)
5'CCGGTGGTCGCCGCGATCAAGGAGTTCTTCGGCACCAGCCAGCTG
AGCCAATTCATGGGCCAGAACAACCCGCTGTCGGGGTTGACCCAC
AAGCGCCGACTGTCGGCGCTGGGGCCCGGCGGTCTGTCACGTGAG
CGTGCCTGGCTGGAG

*M. tuberculosis* strain 8545;
(SEQ ID No. 37)
5'CCGGTGGTCGCCGCGATCAAGGAGTTCTTCGGCACCAGCCAGCTG
AGCCCATTCATGGACCAGAACAACCCGCTGTCGGGGTTGACCCACA
AGCGCCGACTGTCGGCGCTGGGGCCCGGCGGTCTGTCACGTGAGC
GTGCCTGGCTGGAG

*M. africanum*;
(SEQ ID No. 38)
5'CCGGTGGTCGCCGCGATCAAGGAGTTCTTCGGCACCAGCCAGCTG
AGCCAATTCATGGACCAGAACAACCCGCTGTCGGGGTTGACCCAC
AAGCGCCGACTGTCGGCGCTGGGGCCCGGCGGTCTGTCACGTGAG
CGTGCCGGGCTGGAG

*M. intracellulare*;
Not available

The primer sequences for the katG gene:
katG Limiting Primer:
(SEQ ID No. 39)
5' AGCGCCCACTCGTAGCCGTACAGGATCTCGAGGAAAC katG Excess Primer:
(SEQ ID No. 40)
5' TCTTGGGCTGGAAGAGCTCGTATGGCAC The probe sequences for the katG gene:
katG On Probe
(SEQ ID No. 41)
5' Cal Orange 560-GTATCGCGTCCTTACCGGTTCCAC-BHQ2 katG Off Probe
(SEQ ID No. 42)
5' CTCGATGCTGCTGGTG-BHQ2 katG target sequences:
*M. tuberculosis* strains 8545 and 8094;
(SEQ ID No. 43)
5'GCTTGGGCTGGAAGAGCTCGTATGGCACCGGAACCGGTAAGGAC
GCGATCACCACCGGCATCGAGGTCGTATGGACGAACACCCCGACG -continued

AAATGGGACAACAGTTTCCTCGAGATCCTGTACGGCTACGAGTGGG

AGCT

*M. intracellulare*;

(SEQ ID No. 44)

5'GGCTGGGCTGGAAGAGCTCGTACGGCACCGGTTCGGGCAAGGAT

GCGATCACCAGCGGCCTCGAGGTGGTCTGGACGCCCACCCCGACG

AAGTGGGACAACAGCTTCCTGGAGACGCTGTACGGCTACGAATGG

GAGCT

*M. africanum*;
Not available

The primer sequences for the mabA promoter region:
mabA Limiting Primer:
(SEQ ID No. 45)
5' TTCCGGTAACCAGGACTGAACGGGATACGAATGGGGGTTTGG mabA Excess Primer:
(SEQ ID No. 46)

5' TCGCAGCCACGTTACGCTCGTGGACATAC

The probe sequences for the mabA promoter region:
mabA On Probe (SEQ ID No. 47)

5'Cal Red 610-TTACAACCTATCGTCTCGCCGCAA-BHQ2 mabA Off Probe (SEQ ID No. 48)

5' GCAGTCACCCCG-BHQ2 mabA promoter target sequences:
*M. tuberculosis* strain 8094;
(SEQ ID No. 49)

5'TCGCAGCCACGTTACGCTCGTGGACATACCGATTTCGGCCCGGCC

GCGGCGAGACGATAGGTTGTCGGGGTGACTGCCACAGCCACTGAA

GGGGCCAAACCCCCATTCGTATCCCGTTCAGTCCTGGTTACCGGAG

GAAACCGGGGGATCGGGCTGGCGATCGCACAGCGGCTGGCTGCCGA

*M. tuberculosis* strain 8545;

(SEQ ID No. 50)

5'TCGCAGCCACGTTACGCTCGTGGACATACCGATTTCGGCCCGGCC

GCGGCGAGATGATAGGTTGTCGGGGTGACTGCCACAGCCACTGAA

GGGGCCAAACCCCCATTCGTATCCCGTTCAGTCCTGGTTACCGGAG

GAAACCGGGGGATCGGGCTGGCGATCGCACAGCGGCTGGCTGCCGA

*M. intracellulare*;
Not available

*M. africanum*;
Not available

The primer sequences for 16s:
16s Limiting Primer:

(SEQ ID No. 51)

5'-ACACCCTCTCAGGCCGGCTACCCGTCG

16s Excess Primer:

(SEQ ID No. 52)

5'-GAGTGGCGAACGGGTGAGTAACACG

The probe sequences for 16s:
16s On Probe:

(SEQ ID No. 53)

5'-BHQ1 TTGGCTCATCCCACACCGCTAAAGTGCTTTAA-FAM

16s Off Probe:

(SEQ ID No. 54)

5'-BHQ1 CCACCACAAGATATGCGTCTCGTGTTCCTAT-C3

-continued 16s target sequences:
*M. tuberculosis* strains 8545, 8094 and *M. africanum*;

(SEQ ID No. 55)

5'GAGTGGCGAACGGGTGAGTAACACGTGGGTGATCTGCCCTGCAC

TTCGGGATAAGCCTGGGAAACTGGGTCTAATACCGGATAGGACCA

CGGGATGCATGTCTTGTGGTGGAAAGCGCTTTAGCGGTGTGGGATG

AGCCCGCGGCCTATCAGCTTGTTGGTGGGGTGACGGCCTACCAAGG

CGACGACGGGTAGCCGGCCTGAGAGGGTGT

*M. intracellulare*

(SEQ ID No. 56)

5'GAGTGGCGAACGGGTGAGTAACACGTGGGCAATCTGCCCTGCAC

TTCGGGATAAGCCTGGGAAACTGGGTCTAATACCGGATAGGACCTT

TAGACGCATGTCTTTTGGTGGAAAGCTTTTGCGGTGTGGGATGGGC

CCGCGGCCTATCAGCTTGTTGGTGGGGTGACGGCCTACCAAGGCGA

CGACGGGTAGCCGGCCTGAGAGGGTGT

The primer sequences for the gyrase B gene:
gyrase B Excess Primer:

(SEQ ID No. 57)

5' ATACGGGCTTGCGCCGAGGACAC gyrase B Limiting Primer:

(SEQ ID No. 58)

5' GTCAGCGAACCGCAGTTCGAGGGCCAGACCAAGACC

The unlabeled oligo for the gyrase B gene:
Oligo-gyrB:

(SEQ ID No. 59)

5'-CCACTGGTTTGAAGCCAACCCCA-C3

The probe sequences for the gyrase B gene:
gyrase B On Probe:

(SEQ ID No. 61)

5' BHQ1 AGGACGCGAAAGTCGTTGCT-C3-FAM gyrase B Off Probe:

(SEQ ID No. 62)

5' BHQ1 TGAACAAGGCT-C3 gyrase B target sequences:
*M. tuberculosis* strains 8545 and 8094;

(SEQ ID No. 63)

5'GTCAGCGAACCGCAGTTCGAGGGCCAGACCAAGACCAAGTTGGG

CAACACCGAGGTCAAATCGTTTGTGCAGAAGGTCTGTAACGAACA

GCTGACCCACTGGTTTGAAGCCAACCCCACCGACGCGAAAGTCGTT

GTGAACAAGGCTGTGTCCTCGGCGCAAGCCCGTAT

*M. africanum*;

(SEQ ID No. 64)

5'GTCAGCGAACCGCAGTTCGAGGGCCAGACCAAGACCAAGTTGGG

CAACACCGAGGTCAAATCGTTTGTGCAGAAGGTCTGTAACGAACA

GCTGACCCACTGGTTTGAAGCCAACCCCACCGACTCGAAAGTCGTT

GTGAACAAGGCTGTGTCCTCGGCGCAAGCCCGTAT

*M. intracellulare*
Not available.

The sequence for PRIMESAFE 046:

(SEQ ID No. 65)

5'Dabcyl-GGAGCAGACTAGCACTGAGGTA-Dabcyl

```
                                        (SEQ ID No. 66)
5'Dabcyl-TACCTCAGTGCTAGTCTGCTCC-Dabcyl A three carbon linker is denoted with C3 while
black hole quenchers 1 or 2 are denoted with BHQ1
or BHQ2 respectively. (Biosearch Technologies,
Novato CA)
```

LATE-PCR amplifications were performed in triplicate, and carried out in a 25 μl volume consisting of 1×PCR buffer (Invitrogen, Carlsbad, Calif.), 2 mM MgC12, 300 nM dNTPs, 50 nM limiting primer, 1000 nM excess primer, 1.5 units of Platinum Taq DNA Polymerase (Invitrogen, Carlsbad, Calif.), 500 nM of each off probe, 200 nM of each on probe, and 100 nM of PRIMESAFE 046.

The thermal profile for the amplification reaction was as follows: 98° C./3 min for 1 cycle, followed by 98° C./10 s-75° C./45 s for 60 cycles, followed by 10 min at 75° C., followed by 10 min at 25° C. with a melt starting at 25° C. with 1° C. increments at 45 s intervals to 81° C. with fluorescent acquisition at each degree. Probe-target hybridizations were analyzed by the melt curve analysis using the first derivative for each fluorophore separately for the temperatures between 25° C. to 80° C.

The above assay provides means for differentiation of mycobacteria, as evidenced by derivative graphs of temperature-dependent fluorescence signatures in FIG. 16A-D.

Example 5

Detection of a Multi-drug Resistance and Species Identification of M. tuberculosis in a Mixed Sample with Non-Mycobacterium LATE PCR amplifications were performed to provide single-stranded nucleic acid target sequences using multi-drug resistant M. tuberculosis strain 8094 (rpoB gene has D516G, an aspartic acid located at amino acid 516 changed to a glycine, katG gene has S315T, an serine located at amino acid 315 changed to a threonine, the mabA promoter has no mutation thus a wild type sequence) and the M. intracellulare (which had not been characterized for these genes) in different ratios to determine the level of sensitivity within a mixed sample. One reaction mixture contained only strain 8094, and another reaction mixture contained only M. intracellulare. Each of these 100% controls contained approximately 20,000 genomic DNA copies of the pertinent strain. Reaction mixtures for a first mixed sample contained 10% (approximately 2,000 genomes) of resistant strain 8094 with 80% (approximately 18,000 genomes) of M. intracellulare. The reaction mixture for a second mixed sample contained 5% of strain 8094 (1,000 genomes) with 95% of M. intracellulare (19,000 genomes). The reaction mixture for a third mixed sample contained 1% of strain 8094 (200 genomes) with 99% of M. intracellulare (19,800 genomes). The reaction mixture for a fourth mixed sample contained 0.5% of strain 8094 (100 genomes) with 99.5% of M. intracellulare (19,900 genomes). The reaction mixture for a fifth mixed sample contained 0.1% of strain 8094 (20 genomes) with 99.9% of M. intracellulare (19,980 genomes). Reaction components and PCR conditions are described in Example 1 and amplification reactions were run in triplicate.

The data used for graphical analysis of the hybridization for all five genes and their respective probe sets was the average first derivative of the three replicates from the melt profile.

Figure 17:
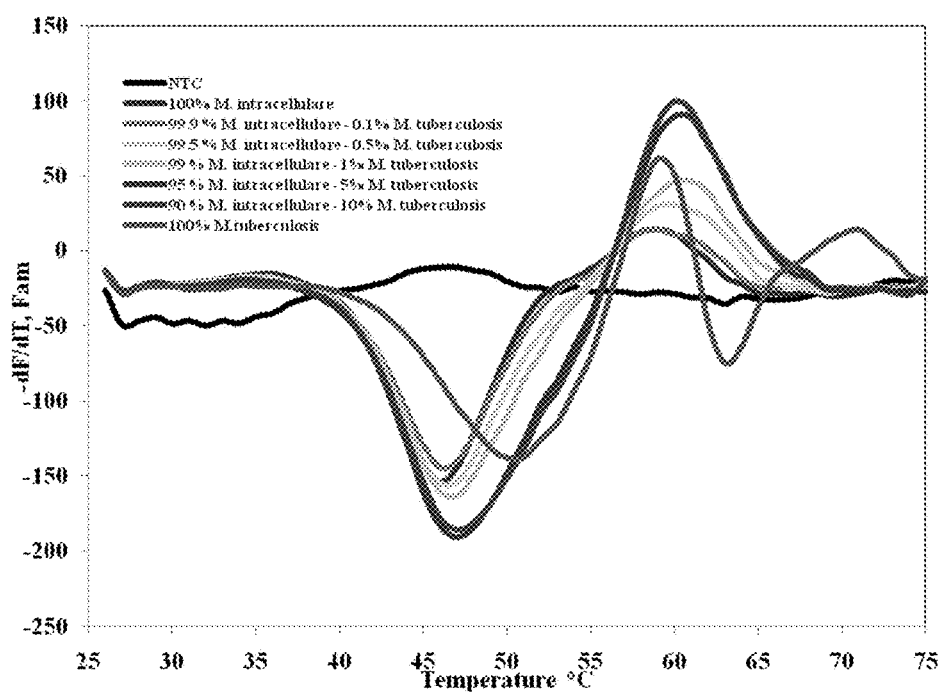
FIG. 17, Panels A to D show graphs demonstrating multi-drug resistance and species identification of *M. tuberculosis* in a mixed sample with non-*Mycobacterium*.
Figure 17:
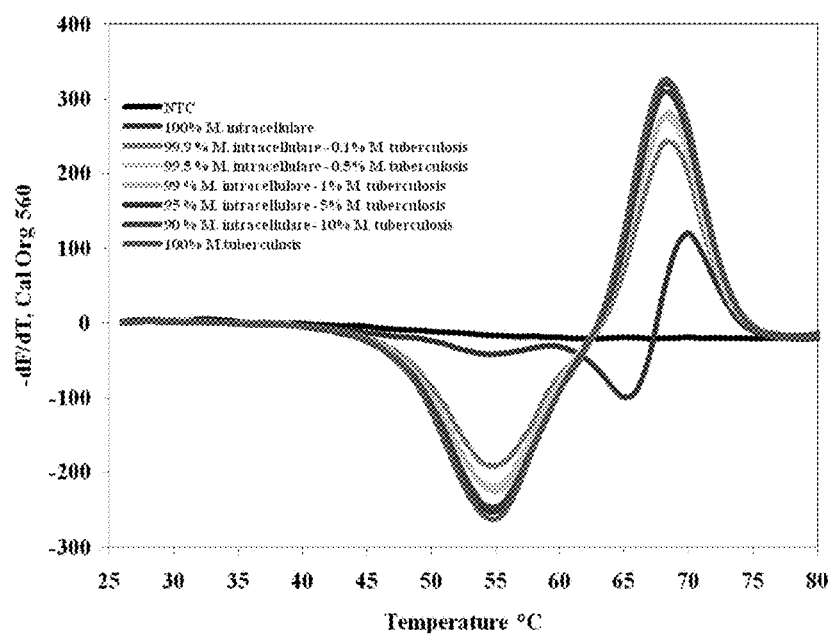
Figure 17:
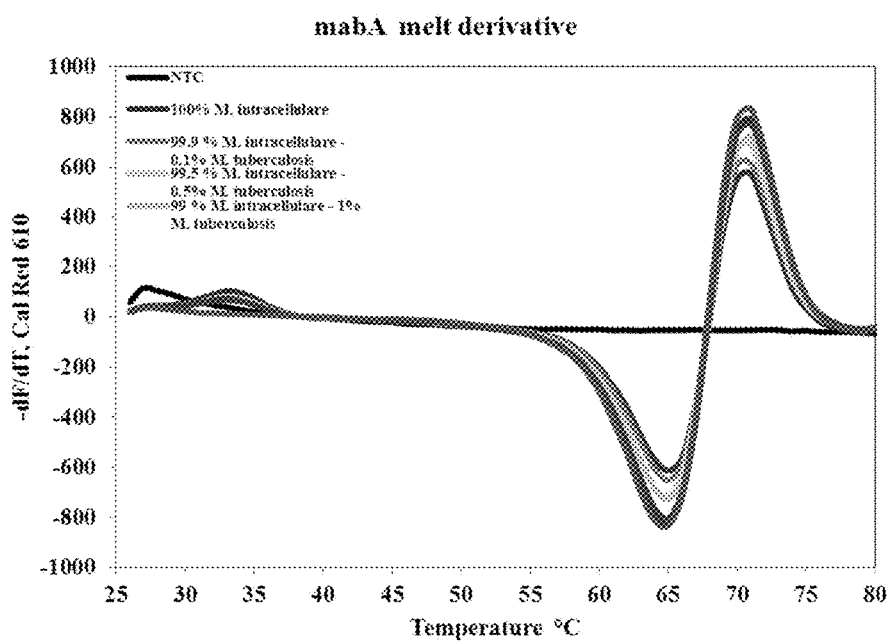
Figure 17:
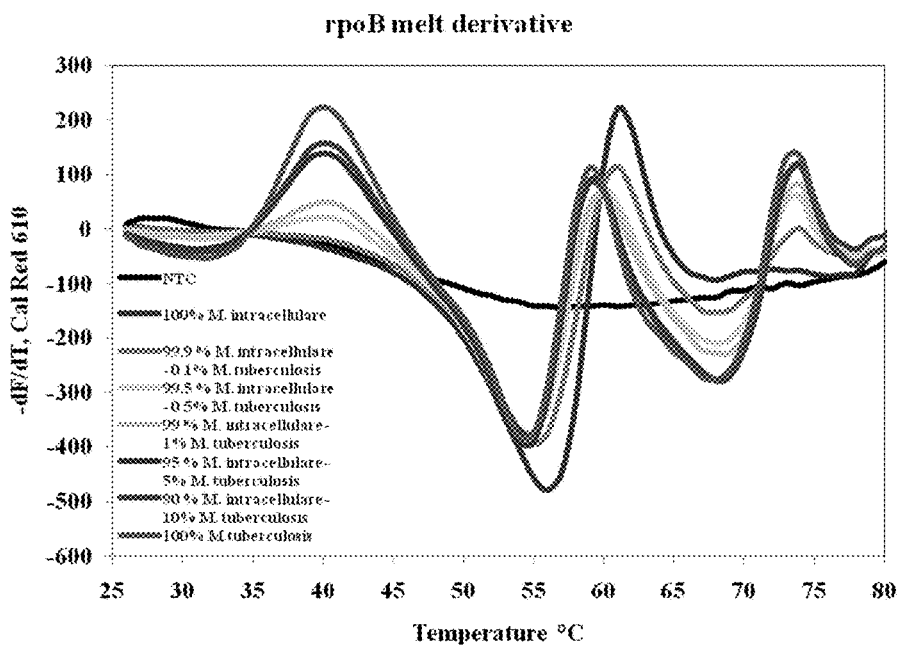

FIGS. 17A-17D shows the resulting analysis. They display the signal from each of the various percentages of the resistant strain 8094 in an increasing background of M. intracellulare as well as the no template controls. FIG. 17A shows the combined fluorescent derivatives of 16s and gyrase B genes in which 100% M. intracellulare and 100% of resistant strain 8094 are distinctly different. As the mixture of strain 8094 decreases from 10%, 5%, 1%, 0.5% these fluorescent signatures becomes more similar to the 100% M. intracellulare however, even at 0.1% of strain 8094 the difference is discernable. FIG. 17B shows the melt derivatives for katG gene where the 100% M. intracellulare is divergent from 100% of resistant strain 8094. For katG this distinctive pattern difference provides an unambiguous detection for all percentages of resistant strain 8094. FIG. 17C shows the mabA promoter region derivatives and is the case in which both the M. intracellulare and 100% of resistant strain 8094 have the same signature shape. The decreasing percentages of strain 8094 show a similar decrease in signal towards the 100% M. intracellulare. FIG. 17D shows the rpoB gene derivatives with distinct fluorescent signatures for M. intracellulare and 100% of resistant strain 8094. As is the case of 16s and gyrase B the different percentages of strain 8094 from 10%, 5%, 1%, 0.5%, and 0.1% these fluorescent signatures becomes more similar to the 100% M. intracellulare but are still distinct and remain unique.

Example 6

Species Identification of M. tuberculosis from other Mycobacterium

The primer and probe sequences for gyrase B are the same as Example 4 with addition of:

```
                                        (SEQ ID No. 60)
gyrase B On Probe: 5' FAM CGTGTAATGAATAGCTGCG-BHQ1 gyrB target sequences:
M. tuberculosis
                                        (SEQ ID No. 63)
5'GTCAGCGAACCGCAGTTCGAGGGCCAGACCAAGACCAAGTTGGG

CAACACCGAGGTCAAATCGTTTGTGCAGAAGGTCTGTAACGAACA

GCTGACCCACTGGTTTGAAGCCAACCCCACCGACGCGAAAGTCGTT

GTGAACAAGGCTGTGTCCTCGGCGCAAGCCCGTAT

M. microti
                                        (SEQ ID No. 75)
5'GTCAGCGAACCGCAGTTCGAGGGCCAGACCAAGACCAAGTTGGG

CAACACCGAGGTCAAATCGTTTGTGCAGAAGGTCTGTAACGAACA

GCTGACCCACTGGTTTGAAGCCAACCCCACCGACTCGAAAGTCGTT

GTGAACAAGGCTGTGTCCTCGGCGCAAGCCCGTAT

M. bovis
                                        (SEQ ID No. 76)
5'GTCAGCGAACCGCAGTTCGAGGGCCAGACCAAGACCAAGTTGGG

CAACACCGAGGTCAAATCGTTTGTGCAGAAGGTCTGTAATGAACAG

CTGACCCACTGGTTTGAAGCCAACCCCACCGACTCGAAAGTCGTTG

TGAACAAGGCTGTGTCCTCGGCGCAAGCCCGTAT
```

M. chelonae

(SEQ ID No. 77)
5'GTCGGCGAACCTCAGTTCGAGGGTCAAACCAAGACCAAGCTGGG

CAACACCGAGGTCAAGTCGTTTGTGCAGAAGGTGTGCAACGAGCA

GCTGCAGCACTGGTTCGACTCGAACCCCGCCGA

M. intracellulare

(SEQ ID No. 78)
5'GTCAGCGAACCGCAGTTCGAGGGTCAGACCAAGACCAAGCTGGG

CAACACCGAAGTGAAGTCGTTCGTGCAGAAGGTCTGCAACGAACA

GCTCACCCACTGGTTCGAGGCCAACCCCGCGGA

M. asiaticum

(SEQ ID No. 79)
5'GTCGCCGAACCCCAGTTCGAGGGCCAGACAAAGACCAAGCTGGG

CAACACCGAGGTCAAGTCGTTCGTGCAGAAGGTGTGCAACGAACA

GCTCACCCACTGGTTCGAGGCCAATCCGTCGGA

M. avium

(SEQ ID No. 80)
5'GTGAGCGAACCGCAGTTCGAGGGCCAGACCAAGACCAAACTGGG

CAACACCGAGGTGAAGTCGTTCGTGCAGAAGGTGTGCAACGAACA

GCTCACCCACTGGTTCGAAGCCAACCCCGCAG

The primer and probe sequences for 16s are the same as Example 4.

16s target sequences:
M. chelonae

(SEQ ID No. 81)
5'GAGTGGCGAACGGGTGAGTAACACGTGGGTGATCTGCCCTGCAC

TCTGGGATAAGCCTGGGAAACTGGGTCTAATACCGGATAGGACCA

CACACTTCATGGTGAGTGGTGCAAAGCTTTTGCGGTGTGGGATGAG

CCCGCGGCCTATCAGCTTGTTGGTGGGGTAATGGCCCACCAAGGCG

ACGACGGGTAGCCGGCCTGAGAGGGTGA

M. asiaticum

(SEQ ID No. 82)
5'GAGTGGCGAACGGGTGAGTAACACGTGGGTGATCTGCCCTGCAC

TTCGGGATAAGCCTGGGAAACTGGGTCTAATACCGGATAGGACCA

CGGGATGCATGTCCTGTGGTGGAAAGCTTTTGCGGTGTGGGATGGG

CCCGCGGCCTATCAGCTTGTTGGTGGGGTGACGGCCTACCAAGGCG

ACGACGGGTAGCCGGCCTGAGAGGGTGT

M. avium

(SEQ ID No. 83)
5'GAGTGGCGAACGGGTGAGTAACACGTGGGCAATCTGCCCTGCAC

TTCGGGATAAGCCTGGGAAACTGGGTCTAATACCGGATAGGACCTC

AAGACGCATGTCTTCTGGTGGAAAGCTTTTGCGGTGTGGGATGGGC

CCGCGGCCTATCAGCTTGTTGGTGGGGTGACGGCCTACCAAGGCGA

CGACGGGTAGCCGGCCTGAGAGGGTGT

M. intracellulare
Same as Example 4

M. fortuitum

(SEQ ID No. 84)
5'GAGTGGCGAACGGGTGAGTAACACGTGGGTGATCTGCCCTGCAC

TCTGGGATAAGCCTGGGAAACTGGGTCTAATACCGAATAGGACCG

CGCTCTTCATGTGGGGTGGTGGAAAGCTTTTGCGGTGTGGGATGGG

CCCGCGGCCTATCAGCTTGTTGGTGGGGTAATGGCCTACCAAGGCG

ACGACGGGTAGCCGGCCTGAGAGGGTGT

Members of *Mycobacterium tuberculosis* complex (*M. tuberculosis*, *M. microti*, *M. bovis*)
Same as Example 4

LATE-PCR amplifications were performed in triplicate carried out in a 25 µl volume consisting of 1×PCR buffer (Invitrogen, Carlsbad, Calif.), 2 mM MgCl2, 200 nM dNTPs, 50 nM limiting primers, 1000 nM excess primers and 1.25 units of Platinum Taq DNA Polymerase (Invitrogen, Carlsbad, Calif.). Three separate mixtures were made; the first had 200 nM of each gyrase B On probe, 500 nM of gyrase B Off probe and 1 uM of unlabeled gyrB oligo, the second mixture had 200 nM of the 16s On probe and 500 nM of 16s Off probe, while the third combined all probes and unlabeled oligos for both gyrase B and 16s.

The thermal profile for the amplification reaction was as follows: 98° C./3 min for 1 cycle, followed by 98° C./10 s-75° C./45 s for 60 cycles, followed by 10 min at 75° C., followed by 10 min at 25° C. with a melt starting at 25° C. with 1° C. increments at 45 s intervals to 81° C. with fluorescent acquisition at each degree. Probe-target hybridizations were analyzed by the melt curve analysis using the first derivative for each fluor separately for the temperatures between 25° C. to 80° C.

Figure 18:
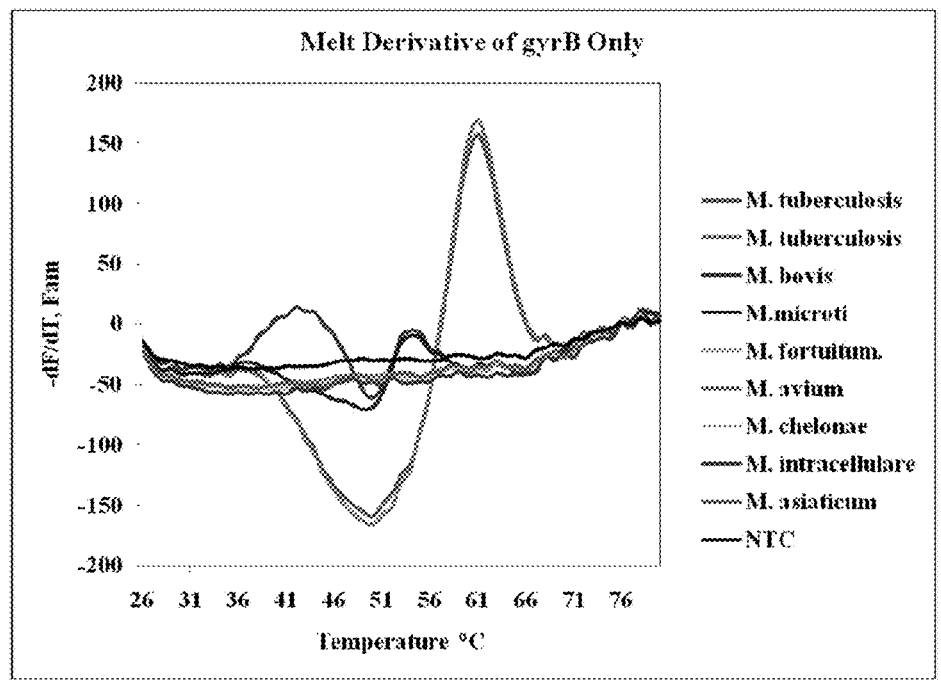
FIG. 18 has three panels showing average melt derivatives. Panel A shows gyrase B probes set with members of the *Mycobacterium tuberculosis* complex (MTBC), Panel B shows 16s probes in which MTBC and NTM species, Panel C shows gyrase B and 16s probes.
Figure 18:
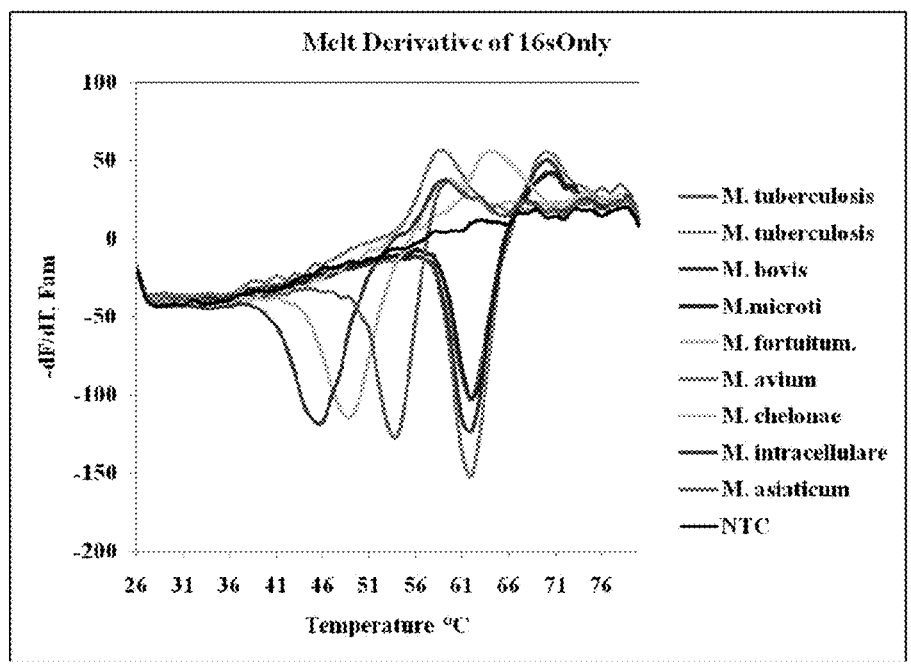
Figure 18:
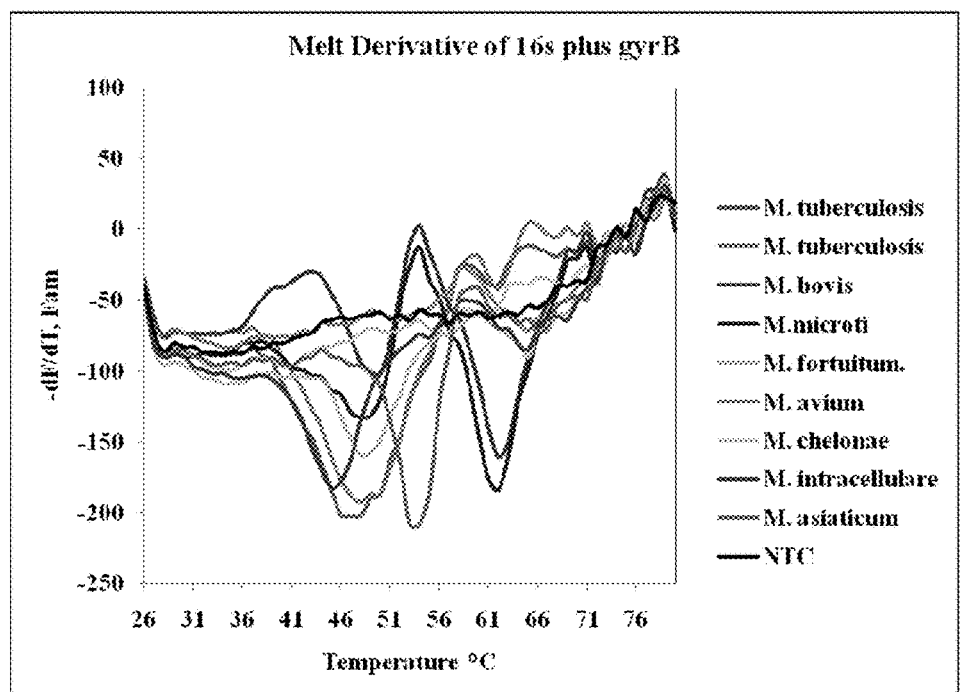

FIG. 18A-C shows the results of the average melt derivatives for each mixture set. FIG. 18A are fluorescent signatures of the gyrase B probes set with members of the *Mycobacterium tuberculosis* complex (MTBC); *M. tuberculosis* strain 10460, strain 15601, *M. bovis*, *M. mircoti*. The non-tuberculosis mycobacterium (NTM) species are *M. fortuitum*, *M. avium*, *M. chelonae*, *M. intracellulare*, *M. asiaticum*, and no template controls. The results of fluorescent signatures clearly separate the NTM's from members of the MTBC with all NTM's showing similar results as the NTC. For members within the MTBC the signatures are also distinct for each; *M. tuberculosis* has a sharp peak at 61C then a negative peak at 49° C., *M. microti* has a peak at 54° C. and minor peak at 49° C., and *M. bovis* positive peaks at 54° C. and 42° C. with a minor negative peak at 49° C. FIG. 18B shows the results from the 16s probes in which all MTBC members have identical fluorescent signatures while all NTM species have their own unique signatures. In FIG. 18C, both probe sets are combined and the results show that all species tested have their own unique fluorescent signatures.

All publications and patents mentioned in the present application are herein incorporated by reference in their entireties. Various modification, recombination, and variation of the described features and embodiments will be apparent to those skilled in the art without departing from the scope and spirit of the invention. Although specific embodiments have been described, it should be understood that the claims should not be unduly limited to such specific embodiments. Indeed, various modifications of the described modes and embodiments can be made without departing from the inventive concepts described herein.

We claim:

1. Reagents for amplification and detection of a type of *mycobacterium* in a sample comprising:
   a) at least one pair of primers, wherein said primers are configured to hybridize to regions of mycobacteria nucleic acid conserved between two or more types of mycobacteria, and wherein said primers are configured to amplify a region of mycobacteria nucleic acid that varies between the two or more types of mycobacteria; and
   b) at least two detectably distinguishable probe sets, wherein each set of the at least two detectably distinguishable probe sets comprises a signaling probe and an associated quencher probe which hybridize to adjacent nucleic acid sequences in an amplified region of mycobacteria nucleic acid amplified by the primers in a), wherein each set of the at least two detectably distinguishable probe sets contains at least one identical probe such that the at least one identical probe is shared between each set of the at least two detectably distinguishable probe sets, and the at least one identical probe is adjacent to two other probes in the at least two detectably distinguishable probe sets on the amplified region of the mycobacteria nucleic acid amplified by the primers in a) when the at least two detectably distinguishable probe sets hybridize to the mycobacteria nucleic acid amplified by the primers in a) such that there are no unhybridized nucleic acid bases between the at least one identical probe and the two other probes on the amplified region of mycobacteria nucleic acid amplified by the primers in a);
   the signaling probe comprising a fluorescence-emitting fluorophore with a quencher of the fluorescence-emitting fluorophore adjacent to the fluorescence-emitting fluorophore on the signaling probe such that said signaling probe does not emit a fluorescent signal above background fluorescence when not hybridized to its target sequence, the quencher probe comprising a non-fluorescent quencher such that when both the quencher probe and the signaling probe are hybridized to the adjacent nucleic acid sequences in the amplified region of the mycobacteria nucleic acid amplified by the primers in a), the non-fluorescent quencher of the quencher probe quenches the fluorescent signal emitted by the fluorescence-emitting fluorophore of the signaling probe,
   wherein said at least one identical probe is the quencher probe, wherein each end of the quencher probe is labeled with a non-fluorescent quencher, the non-fluorescent quencher on one end of the quencher probe interacts with the fluorescence-emitting fluorophore of said signaling probe from one set of the at least two detectably distinguishable probe sets and the non-fluorescent quencher on other end of the quencher probe interacts with said fluorescence-emitting fluorophore of the signaling probe from another set of the at least two detectably distinguishable probe sets when the at least two detectably distinguishable probe sets hybridize to the amplified mycobacteria nucleic acid amplified by the primers in a), or
   said at least one identical probe is either the signal probe or the quencher probe, said at least one identical probe has a fluorophore on its one end and a fluorophore quencher on its other end, the fluorophore of said at least one identical probe interacts with the non-fluorescent quencher of said quencher probe from one set of the at least two detectably distinguishable probe sets and the fluorophore quencher of said at least one identical probe interacts with the fluorescence-emitting fluorophore of said signaling probe from another set of the at least two detectably distinguishable probe sets when the at least two detectably distinguishable probe sets hybridize to the amplified region of mycobacteria nucleic acid amplified by the primers in a).

2. The reagents of claim 1, wherein, in each set of the at least two detectably distinguishable probe sets, the melting temperature of the signaling probe is higher than the melting temperature of the associated quencher probe.

3. The reagents of claim 1, wherein the at least two detectably distinguishable probe sets comprise 5 or more probe sets.

4. The reagents of claim 1, wherein said at least one pair of primers comprises a Limiting Primer and an Excess Primer, wherein the Limiting Primer and Excess Primer have initial concentrations and melting temperatures that allow amplification of a region of mycobacteria nucleic acid that varies between the two or more types of mycobacteria by Linear-After-The-Exponential-PCR.

5. The reagents of claim 1, wherein one or more of the two detectably distinguishable probe sets are configured to hybridize to a region sequence of mycobacteria nucleic acid to differentiate between non-tuberculosis mycobacteria (NTM) and *Mycobacterium tuberculosis* complex (MTBC).

6. The reagents of claim 5, wherein said at least one pair of primers is configured to amplify a mycobacterial nucleic acid sequence that codes for a ribosomal RNA.

7. The reagents of claim 6, wherein the ribosomal RNA is 16S ribosomal RNA.

8. The reagents of claim 7, wherein said reagents comprise one or more of SEQ ID NOS.:51-54.

9. The reagents of claim 1, wherein one or more sets of the at least two detectably distinguishable probe sets are configured to hybridize to a region of mycobacteria nucleic acid to differentiate between different species of MTBC.

10. The reagents of claim 9, wherein one or more primer pairs of the at least one pair of primers are configured to amplify a region of mycobacteria gyrB gene.

11. The reagents of claim 10, wherein said reagents comprise one or more of SEQ ID NOS.:58-62.

12. The reagents of claim 1, wherein three or more detectably distinguishable probe sets of the at least two detectably distinguishable probe sets are configured to hybridize to a region of mycobacteria nucleic acid to differentiate between rifampin-resistant mycobacteria and rifampin-sensitive mycobacteria.

13. The reagents of claim 12, wherein one or more primer pairs of the at least one pair of primers are configured to amplify a region of mycobacteria rpoB gene.

14. The reagents of claim 13, wherein said three or more detectably distinguishable probe sets comprise SEQ ID NO.:30-35.

15. The reagents of claim 14, wherein said at least one pair of primers comprise SEQ ID NO.:28 and SEQ ID NO.:29.

16. The reagents of claim 1, wherein one or more detectably distinguishable probe sets of the at least two detectably distinguishable probe sets are configured to amplify a region of mycobacteria nucleic embB gene to differentiate between ethambutol-resistant mycobacteria and ethambutol-sensitive mycobacteria.

17. The reagents of claim 1, wherein one or more detectably distinguishable probe sets of the at least two detectably distinguishable probe sets are configured to hybridize to a region of mycobacteria nucleic acid to differentiate between isoniazid-resistant mycobacteria and isoniazid-sensitive mycobacteria.

18. The reagents of claim 17, wherein one or more primer pairs of the at least one pair of primers are configured to amplify a region of mycobacteria mabA promoter region.

19. The reagents of claim 18, wherein said reagents comprise one or more of SEQ ID NOS.:45-48.

20. The reagents of claim 17, wherein one or more primer pairs of the at least one pair of primers are configured to amplify a region of mycobacteria ahpC gene.

21. The reagents of claim 17, wherein one or more primer pairs of the at least one pair of primers are configured to amplify a region of mycobacteria katG gene.

22. The reagents of claim 21, wherein said reagents comprise one or more of SEQ ID NOS.:39-42.

23. The reagents of claim 1, wherein one or more detectably distinguishable probe sets of the at least two detectably distinguishable probe sets are configured to hybridize to a region of mycobacteria nucleic acid to differentiate between fluoroquinolone-resistant mycobacteria and fluoroquinolone-sensitive mycobacteria.

24. The reagents of claim 23, wherein one or more primer pairs of the at least one pair of primers are configured to amplify a region of mycobacteria gyrA gene.

25. The reagents of claim 1, wherein said at least two detectably distinguishable probe sets comprise five or fewer optically distinguishable labels.

26. The reagents of claim 1, further comprising one or more control sequences comprising non-mycobacterial nucleic acid.

* * * * *